US006906205B2

(12) United States Patent
Vennerstrom et al.

(10) Patent No.: US 6,906,205 B2
(45) Date of Patent: *Jun. 14, 2005

(54) SPIRO AND DISPIRO 1,2,4-TRIOXOLANE ANTIMALARIALS

(75) Inventors: Jonathan L. Vennerstrom, Omaha, NE (US); Yuxiang Dong, Omaha, NE (US); Jacques Chollet, Basel (CH); Hugues Matile, Basel (CH); Maniyan Padmanilayam, Woburn, MA (US); Yuangqing Tang, Omaha, NE (US); William N. Charman, Parkville (AU)

(73) Assignee: Medicines for Malaria Venture MMV (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/742,010

(22) Filed: Dec. 19, 2003

(65) Prior Publication Data

US 2004/0186168 A1 Sep. 23, 2004

Related U.S. Application Data

(63) Continuation-in-part of application No. PCT/US02/19767, filed on Jun. 21, 2002.

(51) Int. Cl.[7] .................. C07D 323/02; A61K 31/335; A61K 31/357
(52) U.S. Cl. ...................................... 549/341; 514/462
(58) Field of Search .......................... 549/341; 514/462

(56) References Cited

U.S. PATENT DOCUMENTS

| | | |
|---|---|---|
| 3,621,062 A | 11/1971 | Archer et al. |
| 3,673,222 A | 6/1972 | Archer et al. |
| 3,682,991 A | 8/1972 | Tullar et al. |
| 4,816,478 A | 3/1989 | Thornfeldt |
| 4,978,676 A | 12/1990 | Thornfeldt |
| 5,053,342 A | 10/1991 | Lawrence |
| 5,171,676 A | 12/1992 | Ziffer et al. |
| 5,216,175 A | 6/1993 | Avery et al. |
| 5,219,880 A | 6/1993 | Thornfeldt |
| 5,264,879 A | 11/1993 | Shikama |
| 5,270,344 A | 12/1993 | Herman |
| 5,430,148 A | 7/1995 | Webber et al. |
| 5,510,356 A | 4/1996 | Vennerstrom |
| 5,559,145 A | 9/1996 | Jeffort |
| 5,578,637 A | 11/1996 | Lai et al. |
| 5,614,178 A | 3/1997 | Bloom et al. |
| 5,672,624 A | 9/1997 | Posner |
| 5,721,209 A | 2/1998 | Horwitz et al. |
| 5,780,675 A | 7/1998 | Royer et al. |
| 5,817,692 A | 10/1998 | Posner |
| 5,932,591 A | 8/1999 | Posner et al. |
| 6,486,199 B1 * | 11/2002 | Vennerstrom et al. ...... 514/462 |

OTHER PUBLICATIONS

Posner, "Antimalarial peroxides in the qinghaosu (artemisinin) and yingzhaosu families", *Exp. Opin. Ther. Patents* 8(11) 1487–1493 (1998) Ashley Publications Ltd. ISSN 1354–3776.
Jefford, "Peroxidic Antimalarials", *Advances in Drug Research*, vol. 29:271–323 (ISBN 0–12–013329–6) copyright 1997 Academic Press Ltd.
De Almeida Barbosa, Luiz–Claudio, "The design, synthesis and biological evaluation of stable ozonides with antimalarial activity", *J. Chem. Soc., Perkin Trans. 1*, 1101–1105 (1996).
De Almeida Barbosa, Luiz–Claudio, "Synthesis of some Stable Ozonides with Anti-malarial Activity", *J. Chem. Soc., Perkin Trans. 1*, 3251 (1992).
Vennerstrom, et al., "Dispiro–1,2,4,5–tetraoxanes: A New Class of Antimalarial Peroxides", *J. Med. Chem.* 35(16):3023–3027 (1992).
Kuel, Helmut: "Uber Konstitution und Entstehung der Ozonide von Bis–adamantyliden und Bis–Bicyclo '3.3.1lnon–9–yliden" *Chemische Berichte*, vol. 108, No. 4, 1975, pp. 1207–1217, XP002217805.
Tabuchi, T: "Ozonolysis of vinyl ethers in the presence of α–diketones and α–keto esters", *J. Org. Chem.*, vol. 56, 1991, pp. 6591–6595, XP001117555.
Dussault, P.J.: "Selectivity in Lewis acid–mediated fragmentations of peroxides and ozonides; application to the synthesis of alkenes, homoallylethers, and 1,2–dioxolanes", *Perkin Trans*, vol. 1, 2000, pp. 3006–3013, XP001117556.
Griesbaum, Karl, "Diozonides from Coozonolyses of Suitable O–Methyl Oximes and Ketones", *Tetrahedron, Elsevier Science Publishers, Amsterdam, NL*, vol. 53, No. 15, Apr. 14, 1997, pp. 5463–5470 XP004105588.
Meshnick, S:"Artemisinin and the Antimalarial Endoperoxides: From Herbal Remedy to Targeted Chemotherapy", *Microbiological Reviews*, American Society for Microbiology, Washington, DC, US, vol. 60, No. 2, Jun. 1, 1996, pp. 301–315, XP002052313.

* cited by examiner

*Primary Examiner*—Ba K. Trinh
(74) *Attorney, Agent, or Firm*—McKee, Voorhees & Sease, P.L.C.

(57) ABSTRACT

A means and method for treating malaria, schistosomiasis, and cancer using a spiro or dispiro 1,2,4-trioxolane is described. The preferred 1,2,4-trioxolanes include a spiroadamantane group on one side of the trioxolane group, and a spirocyclohexyl on the other side of the trioxolane group, whereby the spirocyclohexyl ring is preferably substituted at the 4-position. In comparison to artemisinin semisynthetic derivatives, the compounds of this invention are structurally simple, easy to synthesize, non-toxic, and potent against malarial parasites.

12 Claims, No Drawings

SPIRO AND DISPIRO 1,2,4-TRIOXOLANE ANTIMALARIALS

CROSS-REFERENCE TO RELATED APPLICATIONS

This application is a continuation-in-part of Application PCT/US02/19767 filed Jun. 21, 2002.

FIELD OF THE INVENTION

This invention relates to compositions and methods for treating malaria. Specifically, this invention relates to pharmaceutical compositions including spiro and dispiro trioxolanes, and methods of their use and manufacture.

BACKGROUND OF THE INVENTION

Malaria is an acute and often chronic infectious disease resulting from the presence of protozoan parasites within red blood cells. Caused by single-celled parasites of the genus *Plasmodium*, malaria is transmitted from person to person by the bite of female mosquitos.

Although once prevalent in North America and other temperate regions of the world, today malaria occurs mostly in tropical and subtropical countries. Each year, between 400 million and 600 million people contract the disease, and 1.5 million to 2.7 million die of the disease.

Four species of *Plasmodium* protozoan parasites are generally responsible for malaria, including *Plasmodium vivax, Plasmodium falciparum, Plasmodium malariae,* and *Plasmodium ovale*. Of the four, *Plasmodium falciparum* is the most dangerous, accounting for half of all clinical cases of malaria and 90% of deaths from the disease.

The transmission of malaria begins when a female mosquito bites a human already infected with the malaria parasite. When the infected mosquito bites another human, sporozoites in the mosquito's saliva are transferred into the blood, which then travel to the liver. In the liver, the sporozoites divide rapidly, then enter the bloodstream where they invade red blood cells. Inside these blood cells, the merozoites multiply rapidly until they cause the red blood cells to burst, releasing into the blood stream a new generation of merozoites that then infect other red blood cells.

The symptoms associated with malaria are generally associated with the bursting of the red blood cells. The destruction of the red blood cells spills wastes, toxin, and other debris into the blood. This in turn causes an intense fever that can leave the infected individual exhausted and bedridden. More severe symptoms associated with repeat infections and/or infection by *Plasmodium falciparum* include anemia, severe headaches, convulsions, delirium and, in some instances, death.

The treatment of malaria has been especially difficult due to the ability of malaria parasites to develop resistance to drugs. Quinine, an antimalarial compound that is extracted from the bark of the South American cinchona tree, is one of the oldest and most effective pharmaceuticals in existence. The downside to quinine is that it is short-acting, and fails to prevent disease relapses. Further, quinine is associated with side effects ranging from dizziness to deafness.

Chloroquine is a synthetic chemical similar to quinine. It became the drug of choice for malaria when it was developed in the 1940s due to its effectiveness, ease of manufacture, and general lack of side effects. However, in the last few decades, malaria parasites in many areas of the world have become resistant to chloroquine.

Mefloquine is another synthetic analog of quinine that has been used in the treatment of malaria. Malaria parasites have also developed resistance to mefloquine, however. Mefloquine is also associated with undesirable central nervous side effects in some patients, including hallucinations and vivid nightmares.

Antifolate drugs are effective against malaria parasites by inhibiting their reproduction. Although the parasites have also developed a resistance to antifolate drugs, the drugs can still be used effectively in combination with other types of antimalarials. The use of combination therapies in treating malaria has the drawbacks of being inconvenient and expensive, however.

More recent developments in the treatment of malaria have involved the use of the peroxide functional group, as exemplified by the drug artemisinin, which contains a unique 1,2,4-trioxane heterocyclic pharmacophore. The antimalarial action of artemisinin is due to its reaction with the iron in free heme molecules in the malaria parasite with the generation of free radicals leading to cellular destruction.

The discovery of artemisinin (qinghaosu), a naturally occurring endoperoxide sesquiterpene lactone (Meshnick et al., 1996; Vroman et al. 1999; Dhingra et al., 2000) initiated a substantial effort to elucidate its molecular mechanism of action (Jefford, 1997; Cumming et al., 1997) and to identify novel antimalarial peroxides (Dong and Vennerstrom, 2001). Many synthetic 1,2,4-trioxanes, 1,2,4,5-tetraoxanes, and other endoperoxides have been prepared.

Although the clinically useful semisynthetic artemisinin derivatives are rapid acting and potent antimalarial drugs, they have several disadvantages including recrudescence, neurotoxicity, (Wesche et al., 1994) and metabolic instability. (White, 1994). A fair number of these compounds are quite active in vitro, but most suffer from low oral activity. (White, 1994; van Agtmael et al., 1999). Although many synthetic antimalarial 1,2,4-trioxanes have since been prepared (Cumming et al., 1996; Jefford, 1997), there exists a need in the art to identify new peroxide antimalarial agents, especially those which are easily synthesized, are devoid of neurotoxicity, and which possess improved pharmacokinetic properties, e.g. improved stability, oral absorption, etc.

Accordingly, it is a primary objective of the present invention to provide compositions and methods for prophylaxis and treatment of malaria using spiro and dispiro 1,2,4-trioxolanes.

It is a further objective of the present invention to provide a composition and method for prophylaxis and treatment of malaria using spiro and dispiro 1,2,4-trioxolanes that is nontoxic.

It is a further objective of the present invention to provide a composition and method for prophylaxis and treatment of malaria using spiro and dispiro 1,2,4-trioxolanes that is metabolically stable and orally active.

It is yet a further objective of the present invention to provide a composition and method for prophylaxis and cost-effective treatment of malaria using spiro and dispiro 1,2,4-trioxolanes that do not involve a treatment regimen of more than three days.

It is a further objective of the present invention to provide compositions and methods for prophylaxis and treatment of malaria using spiro and dispiro 1,2,4-trioxolanes that can be used either as stand-alone medicaments or in combination with other agents.

It is still a further objective of the present invention to provide novel intermediates for synthesizing compositions for prophylaxis and treatment of malaria.

The method and means of accomplishing each of the above objectives as well as others will become apparent from the detailed description of the invention which follows hereafter.

SUMMARY OF THE INVENTION

The invention describes a method and composition for treating malaria with Spiro and dispiro 1,2,4-trioxolanes, their prodrugs and analogues. The trioxolanes of this invention are sterically hindered on one side of the trioxolane heterocycle in order to provide chemical and metabolic stability to the trioxolane ring for better in vivo activity. In one embodiment, the spiro and dispiro trioxolanes are sterically hindered with an unsubstituted, mono-, di-, or poly-substituted $C_5$–$C_{12}$ spiro cycloalkyl group, which may be spiroadamantane. In this embodiment, the spiro and dispiro trioxolanes may include a spirocyclohexyl that is functionalized or substituted at the 4-position or a spiropiperidyl ring that is functionalized or substituted at the nitrogen atom. In another embodiment, the trioxolanes of this invention include an alkyl bridge from the 4-position of the spirocyclohexyl ring connecting a substituent that is most preferably a weak base. The invention embraces achiral, achiral diastereomers, racemic mixtures, as well as enantiomeric forms of the compounds.

The trioxolanes of this invention possess excellent potency and efficacy against *Plasmodium* parasites, and a low degree of neurotoxicity. In addition, several of the trioxolanes are suitable for both oral and non-oral administration. Moreover, in comparison to artemisinin semisynthetic derivatives, the compounds of this invention are structurally simple, easy and inexpensive to synthesize, and can be used effectively alone or in conjunction with other antimalarials.

DETAILED DESCRIPTION OF THE PREFERRED EMBODIMENT

The present invention relates to the development of spiro and dispiro 1,2,4-trioxolanes for use in the prophylaxis and treatment of malaria. The present invention is predicated upon the unexpected discovery that trioxolanes that are relatively sterically hindered on at least one side of the trioxolane heterocycle provide metabolic and chemical stability to the trioxolane ring, thereby providing better in vivo activity, especially with respect to oral administration.

As used herein the term "prophylaxis-effective amount" refers to a concentration of compound of this invention that is effective in inhibiting or preventing infection and subsequent disease by malarial parasites. Likewise, the term "treatment-effective amount" refers to a concentration of compound that is effective in treating malaria in terms of preventing an increase in the concentration of malarial parasites, decreasing the concentration of malarial parasites, and/or "curing" a malaria infection, i.e. survival for 30 days post-infection.

Tetrasubstituted trioxolanes are relatively stable peroxidic compounds based on literature precedent (Griesbaum et al., 1997a; 1997b). This may be due, in part, to the lack of α-hydrogen atoms. The present inventors have synthesized new compounds in the trioxolane class having both superior antimalarial potency and oral efficacy. Furthermore, the compounds of this invention have low toxicity, and half-lives conducive to treatment of malaria which are believed will permit short-term treatment regimens comparing favorably to other artemisinin-like drugs. These compounds may also be used in malaria prophylaxis.

In previous application, the present inventors disclosed certain novel tetrasubstituted trioxolanes having the following structural formula:

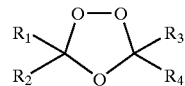

wherein $R_1$, $R_2$, $R_3$, and $R_4$ represent combinations of ring systems, acyclic systems, and functional groups that provide sufficient steric hindrance about the trioxolane ring in order to give the ring chemical and metabolic stability. $R_1$, $R_2$, $R_3$ and $R_4$ may be the same or different, and may be a linear or branched alkyl, aryl, or alkaryl group which is optionally substituted. In the alternative, $R_1$ and $R_2$ taken together and/or $R_3$ and $R_4$ taken together may form an alicyclic group which is optionally interrupted by one or more oxygen, sulfur or nitrogen atoms and which group is optionally substituted. In no event may any of $R_1$, $R_2$, $R_3$ or $R_4$ be hydrogen.

In one embodiment, the compounds include those whereby $R_1$ and $R_2$ taken together and/or $R_3$ and $R_4$ taken together is a mono- or di-substituted $C_5$-$C_{12}$ spirocycloalkyl group which is optionally interrupted by one or more oxygen, sulfur, or nitrogen atoms, and which group is optionally substituted. In another embodiment, $R_1$ and $R_2$ taken together or $R_3$ and $R_4$ is spiroadamantane.

The present invention discloses a new embodiment of trioxolane compounds having the following structure:

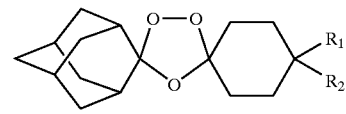

The spirocyclohexyl ring may be optionally interrupted by one or more oxygen, sulfur or nitrogen atoms. In this regard, $R_1$ and $R_2$ may be the same or different, and may be hydrogen, substituted or unsubstituted linear or branched alkyl, aryl, and alkaryl groups and substituted or unsubstituted alicyclic groups that may be interrupted by one or more oxygen, sulfur or nitrogen atoms, substituted or unsubstituted aromatic or heterocyclic groups that may be interrupted by one or more oxygen, sulfur or nitrogen atoms, a hydroxy group, or a halogen. In one embodiment, $R_1$ or $R_2$ is an amide. It has been unexpectedly found that amide-containing substituents at the 4-position provide antimalarial compounds with good oral absorption, good antimalarial activity, and good pharmacokinetics, i.e. rates of absorption, metabolism, and elimination that are suitable and advantageous for the prophylaxis and treatment of malaria.

In another embodiment, the compounds of this invention have the following structural formula:

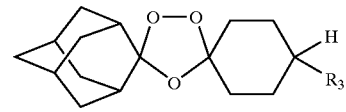

whereby $R_3$ is $(CH_2)_n$—Y. In this formula, Y represents a functional group that, in one embodiment, is non-acidic, and in another embodiment is a weak base. The Y functional group may be an alkyl, ketone, acid, alcohol, amine, amide, sulfonamide, guanidine, ether, ester, oxime, urea, oxime ether, sulfone, lactone, carbamate, semicarbazone, phenyl, or heterocycle. In one embodiment, n=1. The alkyl "bridge" group has been found to improve the metabolically stability (i.e. oral activity and pharmacokinetics) of the antimalarial compounds of this invention.

In another embodiment of the invention, the trioxolanes are weak bases, which provide an ideal combination of high intrinsic potency and good oral activity. Two promising trioxolane structural subtypes are weak base amides of trioxolane amine OZ209 and trioxolane acid OZ78. These compounds have one of the following two structural formulas:

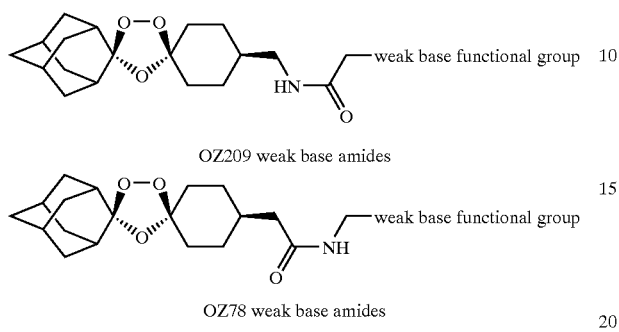

OZ209 weak base amides

OZ78 weak base amides

Other substituents at the 4-position of the spirocyclohexyl ring are also possible that fall within the scope of this invention. The spirocyclohexyl ring may also be substituted at other positions besides the 4-position. For instance, the inventors have synthesized several compounds substituted at the 2-position of the spirocyclohexyl ring that provide excellent antimalarial potency.

In another embodiment of this invention, the compounds include an alkyl group connecting the substituent at the 4-position to the spirocyclohexyl ring. In one embodiment, the alkyl group is methyl or ethyl. In another embodiment, the alkyl group is methyl. The substituent may also be directly attached to the 4-position of the spirocyclohexyl ring.

The present inventors have identified two orally active lead dispiro-1,2,4-trioxolanes, OZ03 and OZ05:

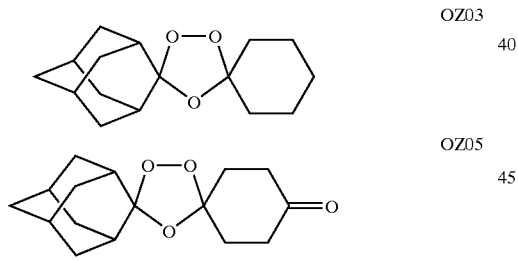

OZ03

OZ05

These trioxolanes have $IC_{50}s$ between 1 and 5 ng/ml against P. falciparum in vitro, and presumably possess good therapeutic indices as no toxicity is evidence for either compound in a neuroblastoma cell line or at single 640 mg/kg doses in mice in the Rane test. These results contrast with published data (de Almeida Barbosa et al., 1992; 1996) disclosing the weak in vitro antimalarial potency of several tricyclic trioxolanes, the best of which has an $IC_{50}$ of 2000 ng/ml against P. falciparum in vitro.

A notable feature of these trioxolanes in comparison to the artemisinin semisynthetic derivatives is their structural simplicity. A potential advantage of trioxolanes over both trioxanes (Jefford, 1997; Cumming et al., 1997) and tetraoxanes (Vennerstrom et al., 2000) is a more convenient access to structurally diverse, non-symmetrical, and in many cases, achiral compounds.

Below are several dispiro 1,2,4-trioxolanes synthesized in accordance with the teachings of this invention. "OZ" is an internal designation for these compounds that will be used throughout the remainder of the application for convenience.

OZ Series 1 (OZ01–OZ09)

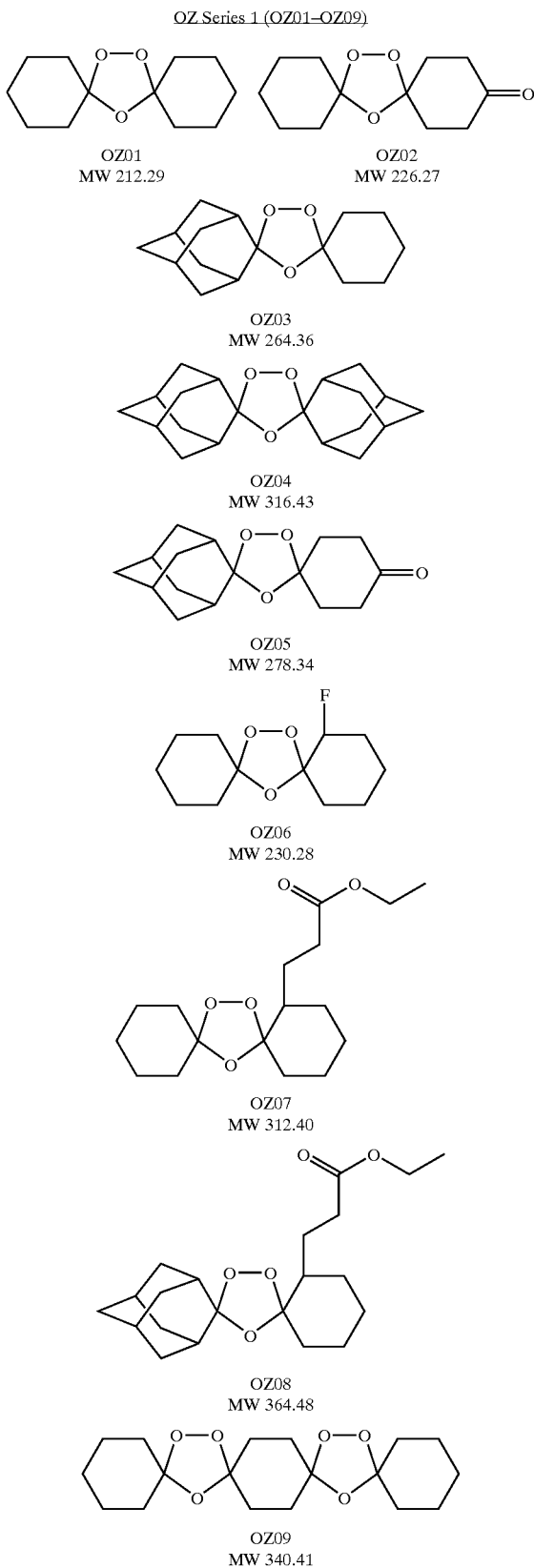

OZ Series 2 (OZ10–OZ18)
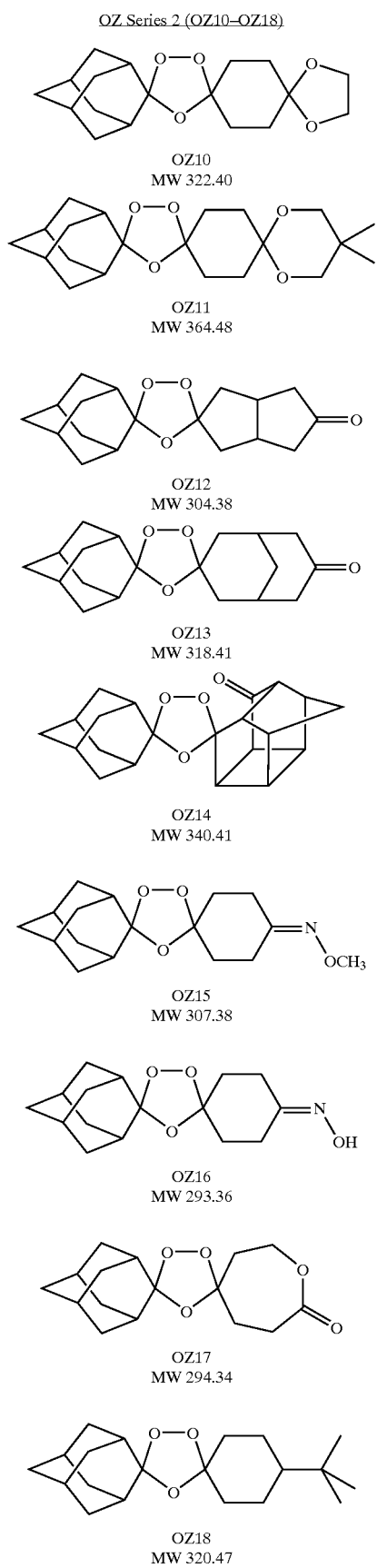
OZ10
MW 322.40
OZ11
MW 364.48
OZ12
MW 304.38
OZ13
MW 318.41
OZ14
MW 340.41
OZ15
MW 307.38
OZ16
MW 293.36
OZ17
MW 294.34
OZ18
MW 320.47
OZ Series 3 (OZ19–OZ27)
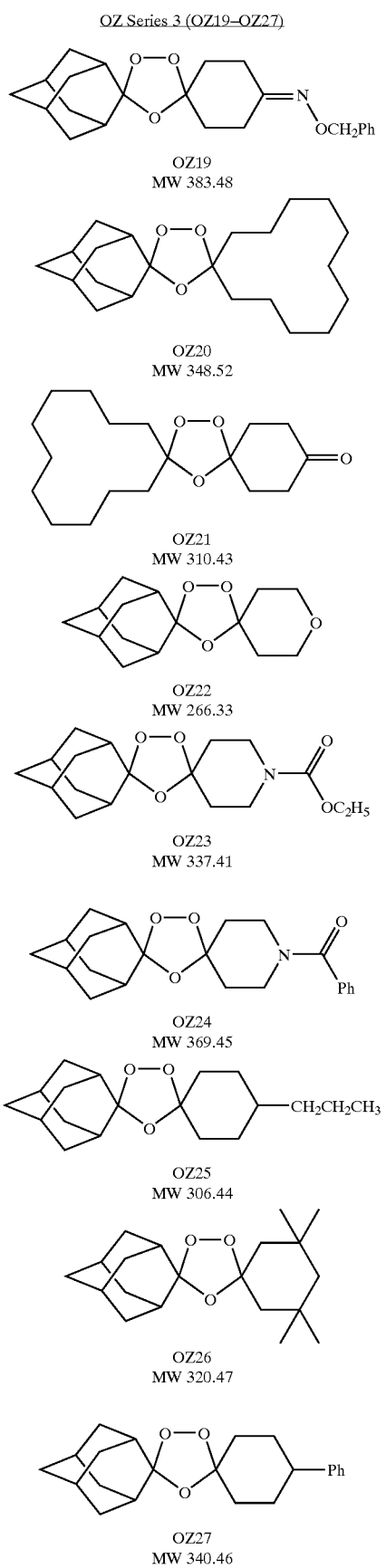
OZ19
MW 383.48
OZ20
MW 348.52
OZ21
MW 310.43
OZ22
MW 266.33
OZ23
MW 337.41
OZ24
MW 369.45
OZ25
MW 306.44
OZ26
MW 320.47
OZ27
MW 340.46

OZ Series 4 (OZ28–OZ36)

OZ28
MW 349.46

OZ29
MW 458.46

OZ30
MW 411.49

OZ31
MW 398.49

OZ32
280.36

OZ33
292.41

OZ34
MW 416.55

OZ35
MW 365.46

OZ36
MW 368.51

OZ Series 5 (OZ37–OZ45)

OZ37
MW 333.42

OZ38
MW 422.47

OZ39
MW 446.56

OZ40
MW 306.44

OZ41
MW 358.45

OZ42
MW 348.43

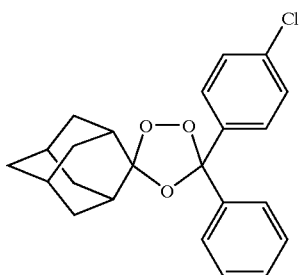
OZ43
MW 417.32
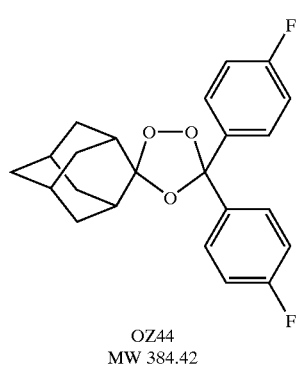
OZ44
MW 384.42
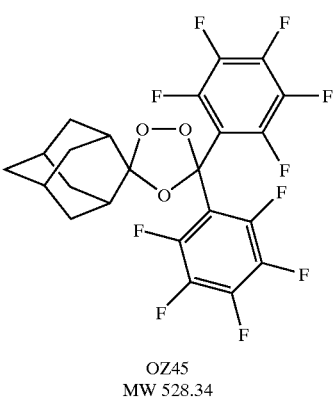
OZ45
MW 528.34
OZ Series 6 (OZ46–OZ54)
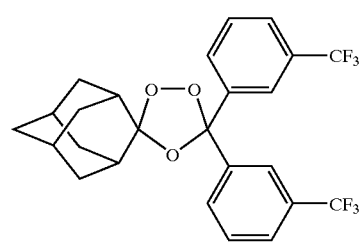
OZ46
MW 484.43
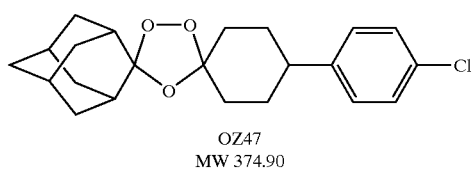
OZ47
MW 374.90
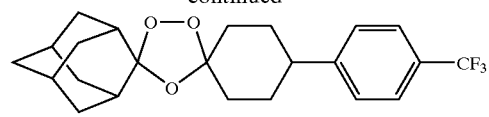
OZ48
MW 408.45
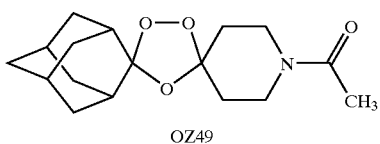
OZ49
MW 307.38
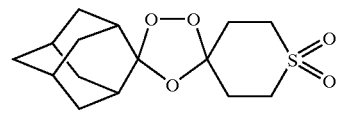
OZ50
MW 314.40
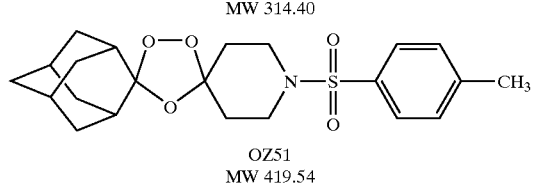
OZ51
MW 419.54
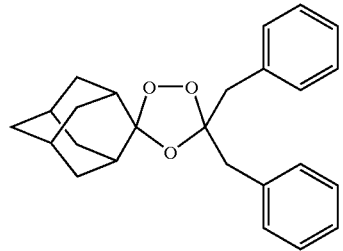
OZ52
MW 376.49
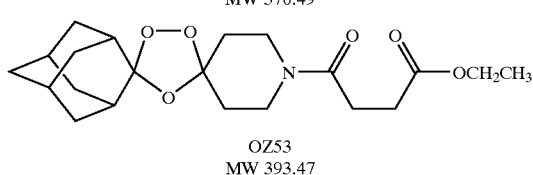
OZ53
MW 393.47
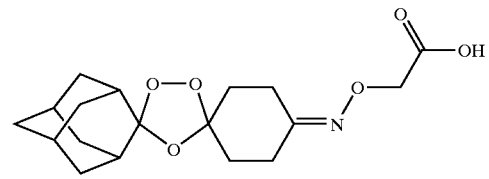
OZ54
MW 351.39
OZ Series 7 (OZ55–OZ63)
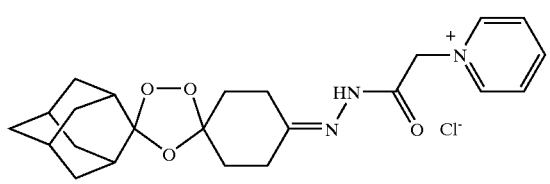
OZ55
MW 447.95

-continued
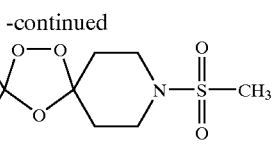
OZ56
MW 343.44
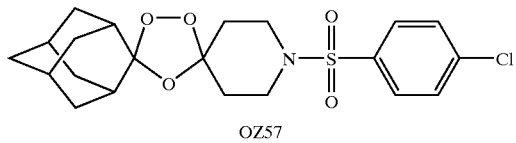
OZ57
MW 439.95
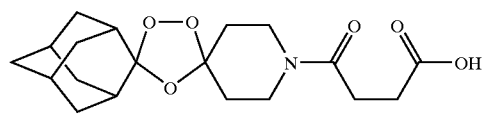
OZ58
MW 365.42
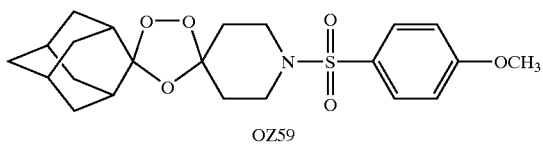
OZ59
MW 435.53
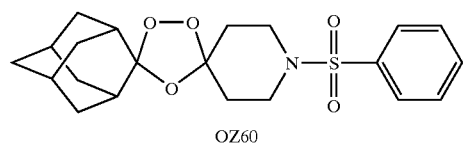
OZ60
MW 405.51
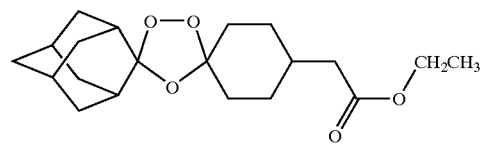
OZ61
MW 350.45
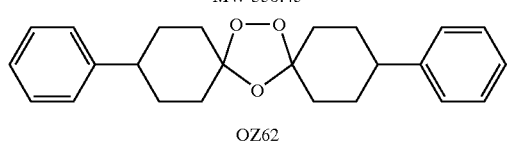
OZ62
MW 364.48
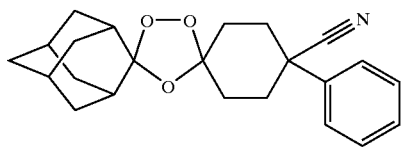
OZ63
MW 365.47
OZ Series 8 (OZ64–OZ72)
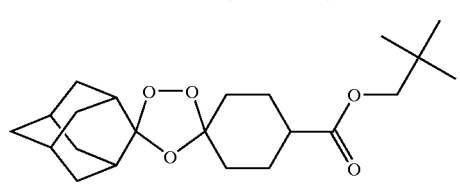
OZ64
MW 378.50
-continued
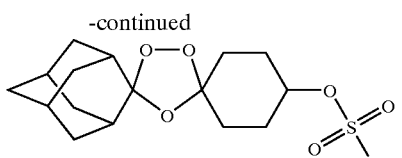
OZ65
MW 382.41
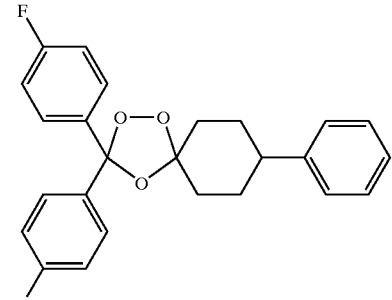
OZ66
MW 408.44
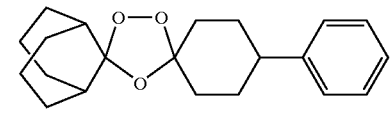
OZ67
MW 328.45
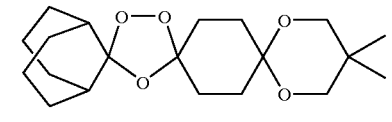
OZ68
MW 352.47
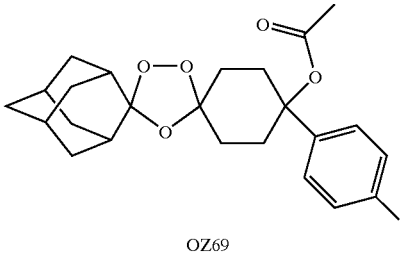
OZ69
MW 416.48
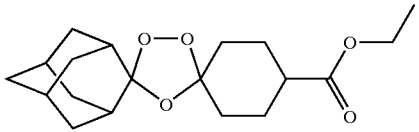
OZ70
MW 336.42
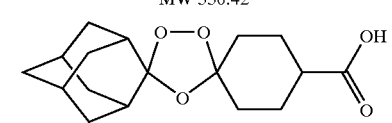
OZ71
MW 308.37
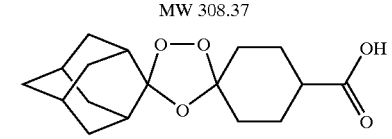
OZ72
MW 308.37

OZ Series 9 (OZ73–OZ81)

OZ73
MW 363.49

OZ74
MW 384.47

OZ75
MW 434.35

OZ76
MW 374.45

OZ77
MW 388.47

OZ78
MW 322.40

OZ79
MW 357.47

OZ80
MW 301.81

OZ81
MW 350.41

OZ Series 10 (OZ82–OZ90)

OZ82
MW 365.42

OZ83
MW 323.38

OZ84
MW 312.40

OZ85
MW 312.40

OZ86
MW 423.50

OZ87
MW 341.83

OZ88
MW 457.52

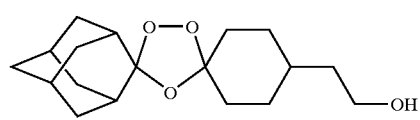
OZ89
MW 308.41
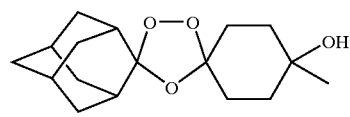
OZ90
MW 294.39
OZ Series 11 (OZ91–OZ99)
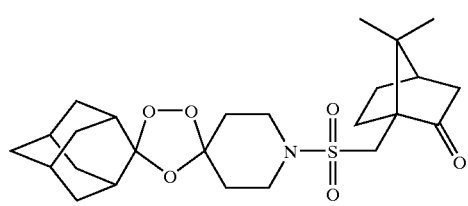
OZ91
MW 479.63
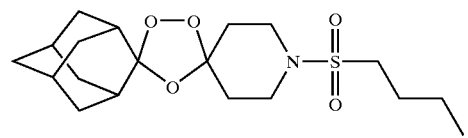
OZ92
MW 385.52
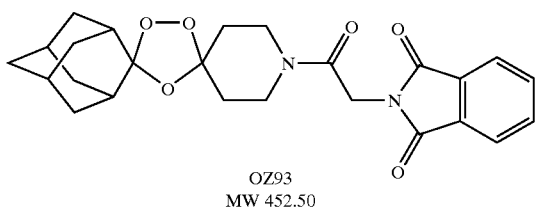
OZ93
MW 452.50
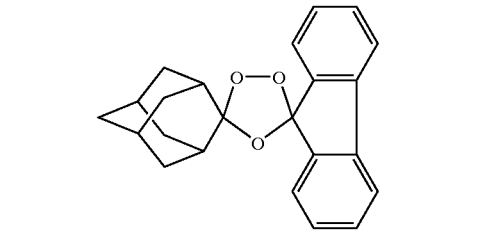
OZ94
MW 346.42
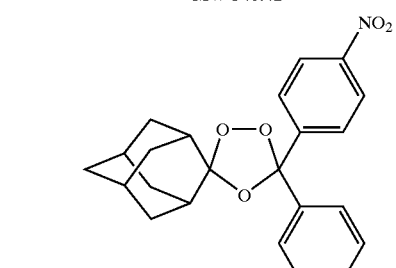
OZ95
MW 393.43
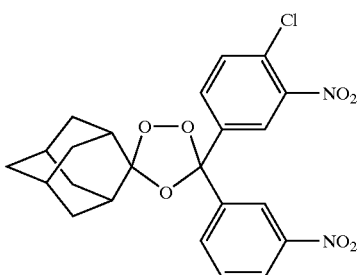
OZ96
MW 507.32
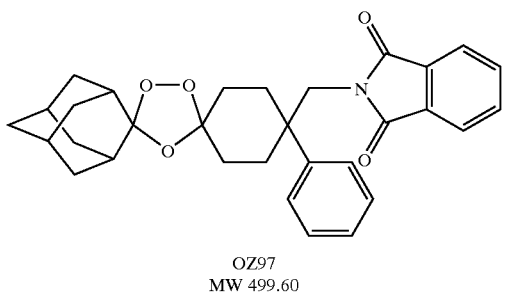
OZ97
MW 499.60
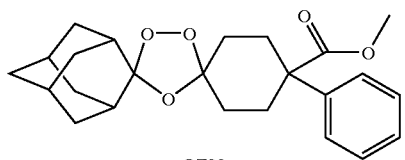
OZ98
MW 398.49
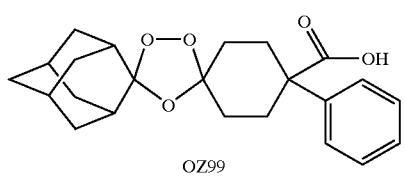
OZ99
MW 384.47
OZ Series 12 (OZ100–OZ108)
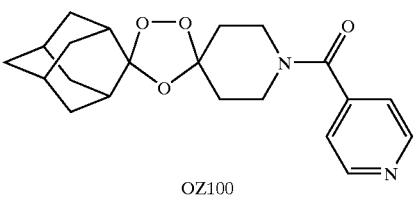
OZ100
MW 370.44
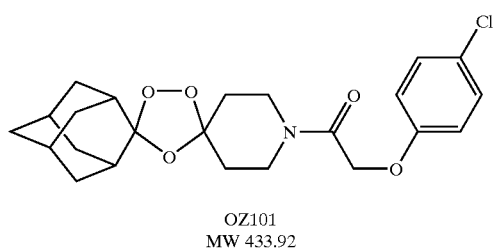
OZ101
MW 433.92

OZ Series 13 (OZ109–OZ117)

OZ102 MW 384.47

OZ103 MW 373.45

OZ104 MW 462.56

OZ105 MW 438.43

OZ106 MW 580.58

OZ107 MW 323.38

OZ108 MW 322.44

OZ109 MW 415.44

OZ110 MW 363.45

OZ111 MW 363.49

OZ112 MW 381.42

OZ113 MW 337.41

OZ114 MW 456.56

OZ115 MW 441.63

OZ116 MW 323.38

OZ117 MW 405.96

OZ Series 14 (OZ118–OZ126)
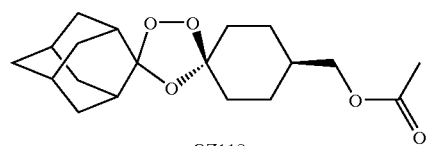
OZ118
MW 336.42
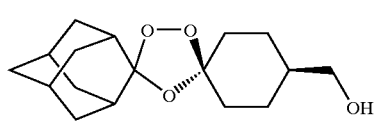
OZ119
MW 294.39
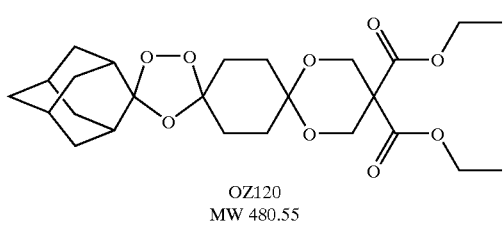
OZ120
MW 480.55
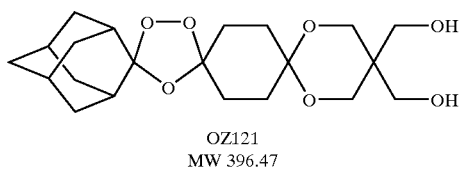
OZ121
MW 396.47
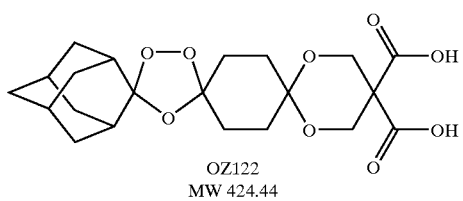
OZ122
MW 424.44
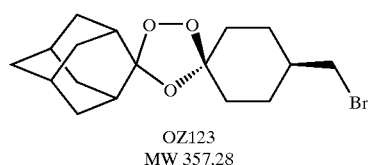
OZ123
MW 357.28
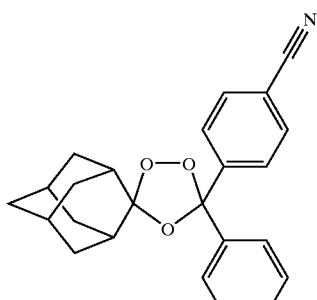
OZ124
MW 373.44
-continued
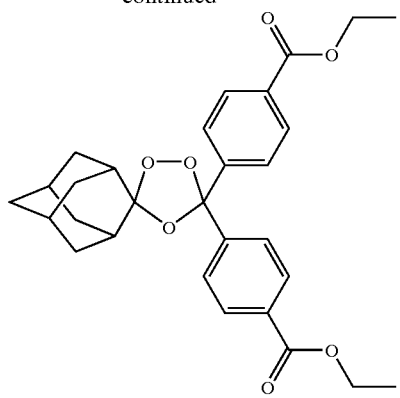
OZ125
MW 492.56
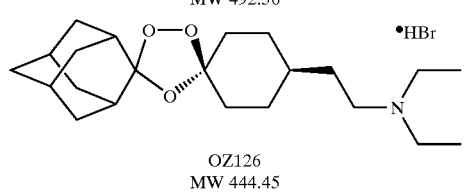
OZ126
MW 444.45
OZ Series 15 (OZ127–OZ135)
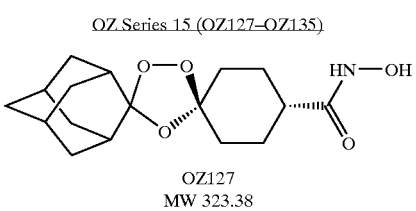
OZ127
MW 323.38
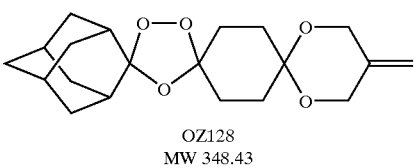
OZ128
MW 348.43
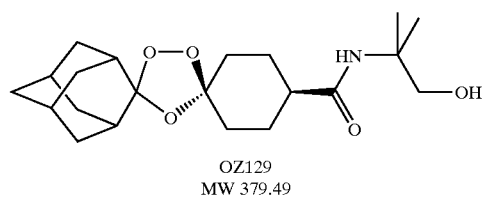
OZ129
MW 379.49
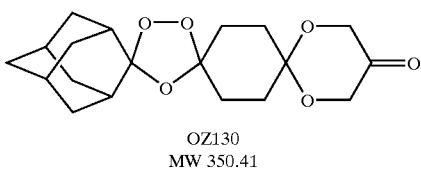
OZ130
MW 350.41
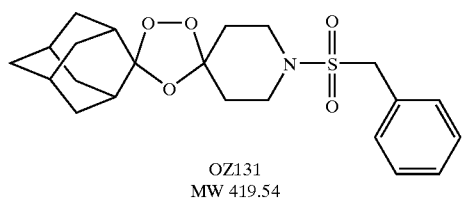
OZ131
MW 419.54

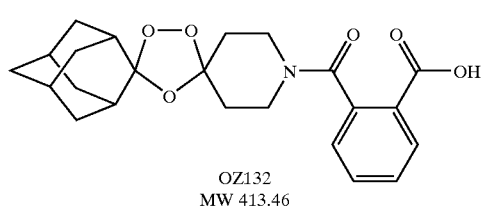
OZ132
MW 413.46
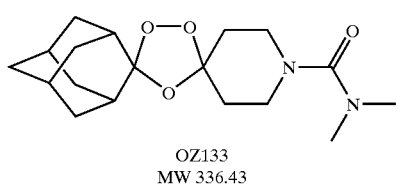
OZ133
MW 336.43
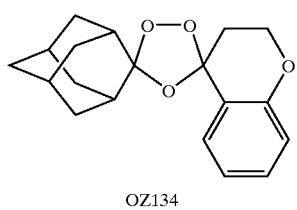
OZ134
MW 314.38
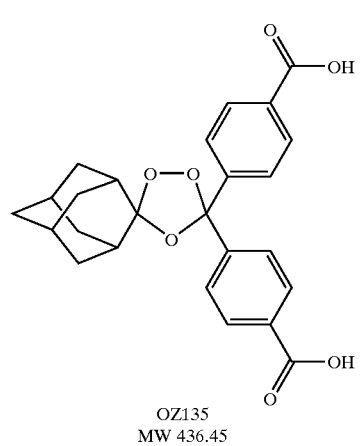
OZ135
MW 436.45
OZ Series 16 (OZ136–OZ144)
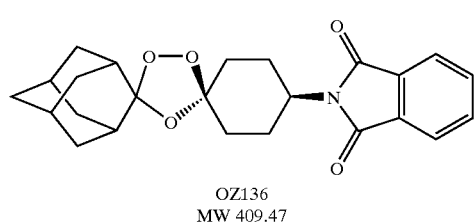
OZ136
MW 409.47
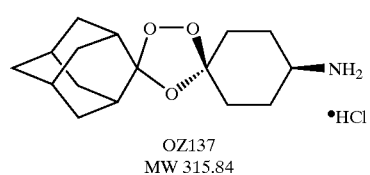
OZ137
MW 315.84
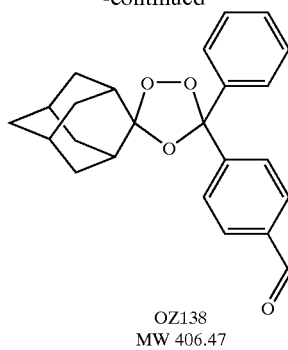
OZ138
MW 406.47
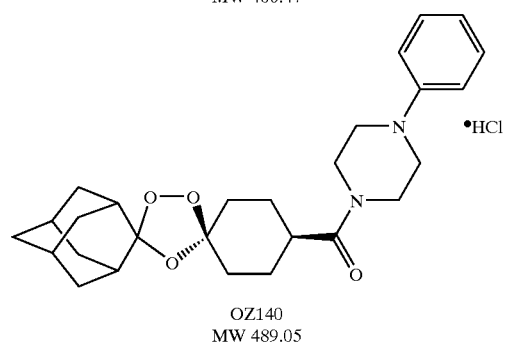
OZ140
MW 489.05
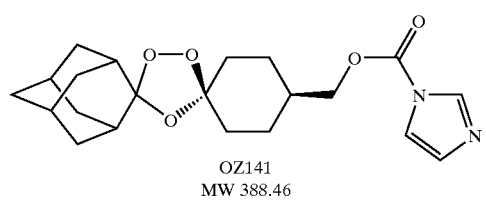
OZ141
MW 388.46
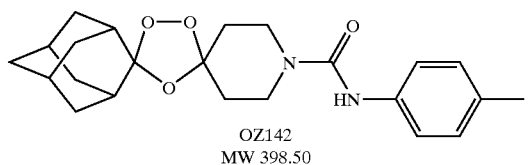
OZ142
MW 398.50
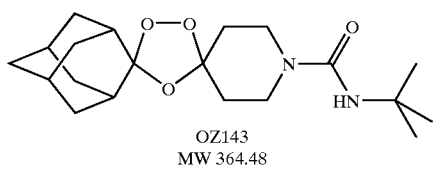
OZ143
MW 364.48
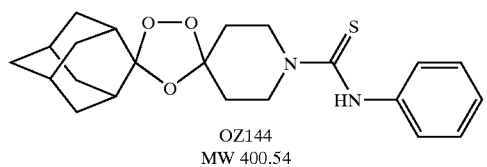
OZ144
MW 400.54
OZ Series 17 (OZ145–OZ153)
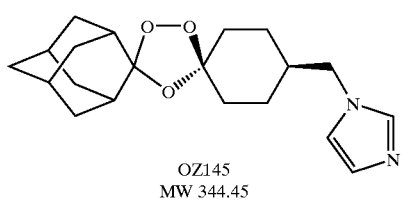
OZ145
MW 344.45

-continued
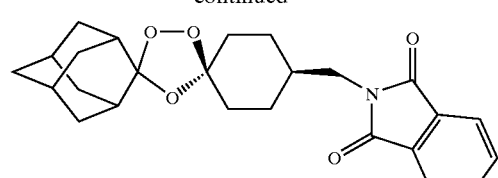
OZ146
MW 423.50
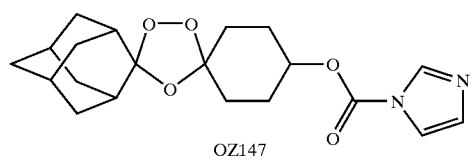
OZ147
MW 374.43
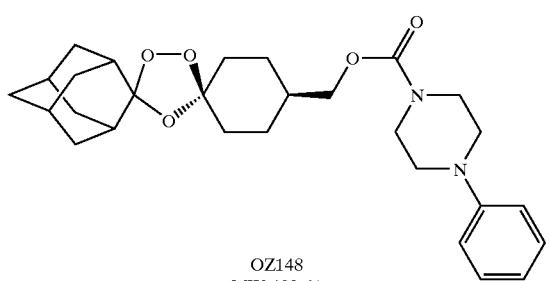
OZ148
MW 482.61
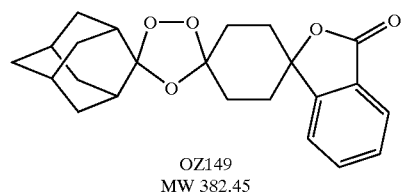
OZ149
MW 382.45
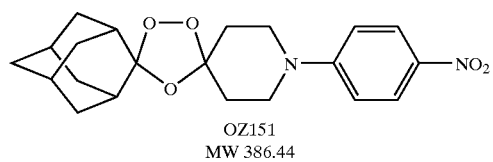
OZ151
MW 386.44
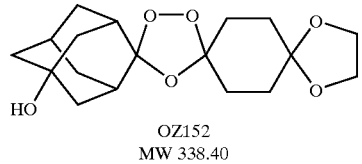
OZ152
MW 338.40
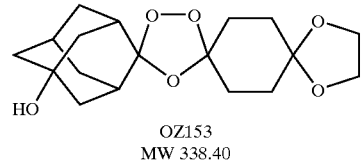
OZ153
MW 338.40
OZ Series 18 (OZ154–OZ162)
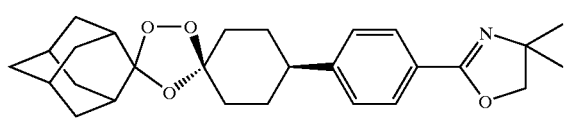
OZ154
MW 437.57
-continued
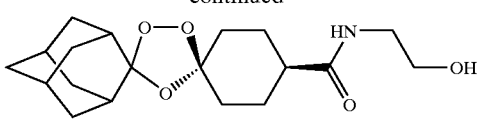
OZ155
MW 351.44
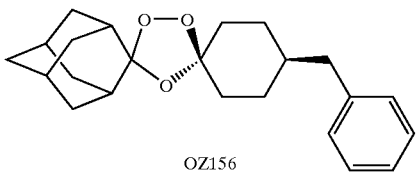
OZ156
MW 354.48
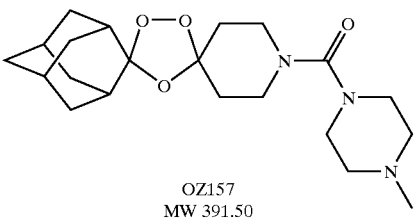
OZ157
MW 391.50
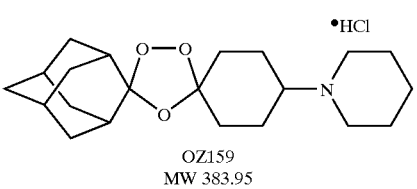
OZ159
MW 383.95
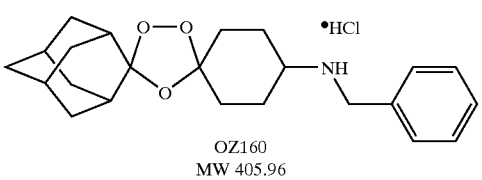
OZ160
MW 405.96
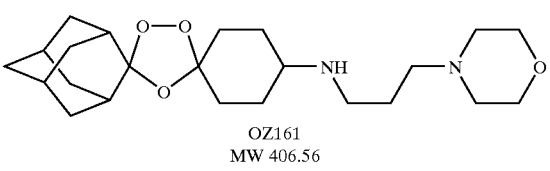
OZ161
MW 406.56
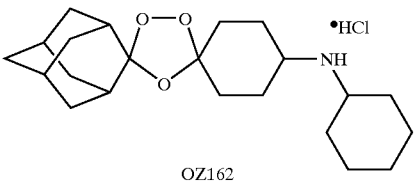
OZ162
MW 397.98
OZ Series 19 (OZ163–OZ171)
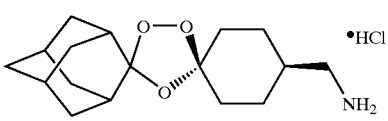
OZ163
MW 329.86

-continued
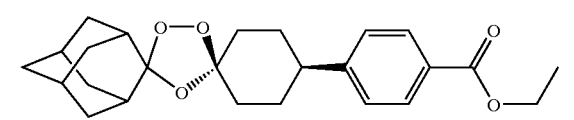
OZ164
MW 412.52
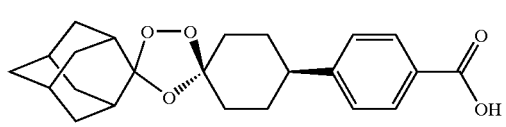
OZ165
MW 384.47
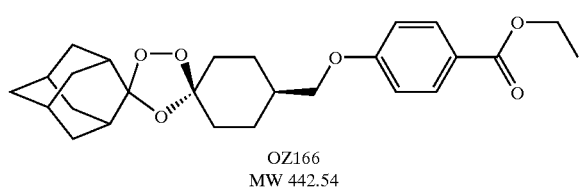
OZ166
MW 442.54
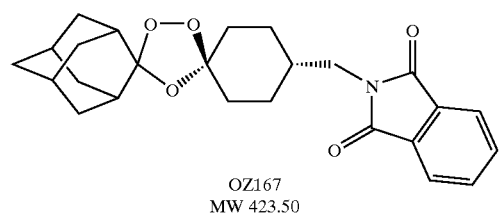
OZ167
MW 423.50
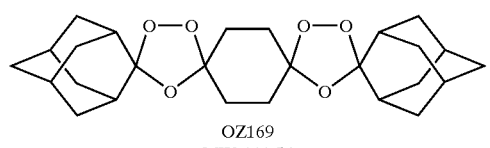
OZ169
MW 444.56
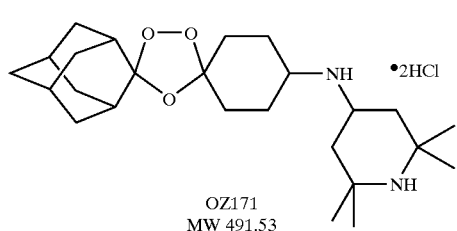
OZ171
MW 491.53
OZ Series 20 (OZ172–OZ180)
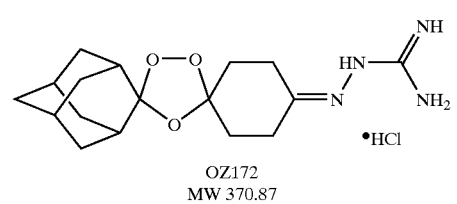
OZ172
MW 370.87
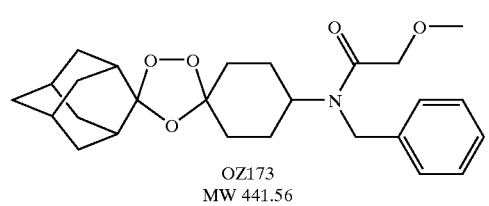
OZ173
MW 441.56
-continued
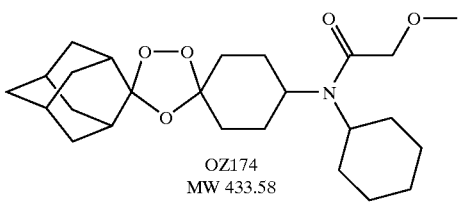
OZ174
MW 433.58
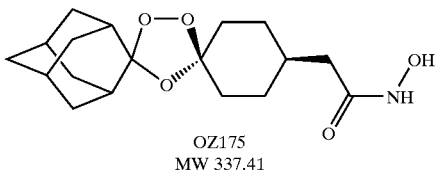
OZ175
MW 337.41
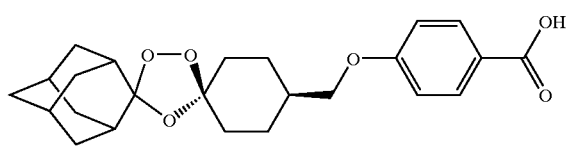
OZ176
MW 414.49
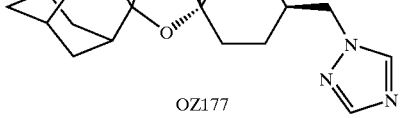
OZ177
MW 345.44
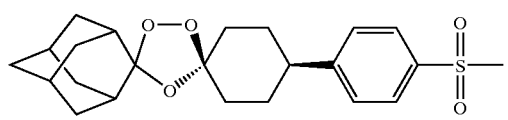
OZ178
MW 418.55
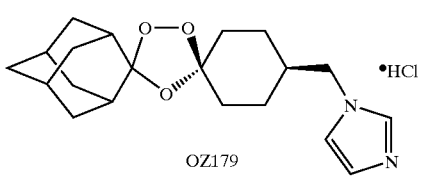
OZ179
MW 380.91
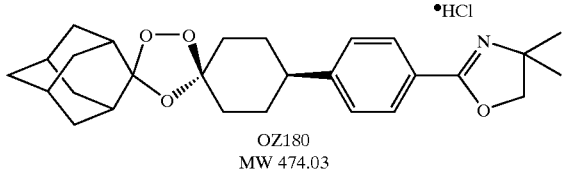
OZ180
MW 474.03
OZ Series 21 (OZ181–OZ189)
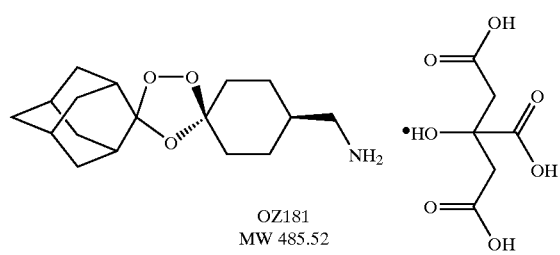
OZ181
MW 485.52

-continued
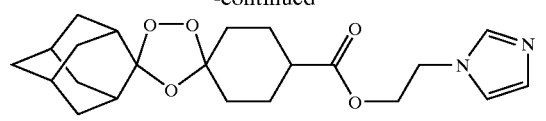
OZ182
MW 402.48
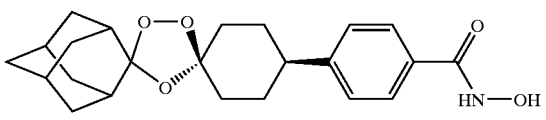
OZ183
MW 399.48
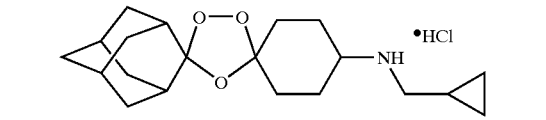
OZ184
MW 369.93
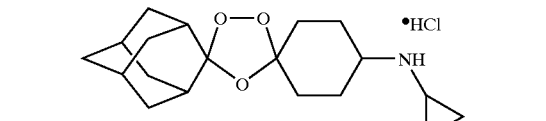
OZ185
MW 355.90
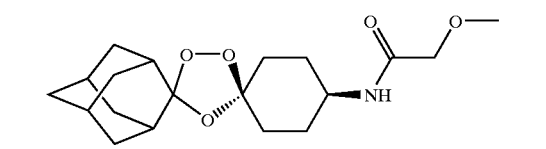
OZ186
MW 351.44
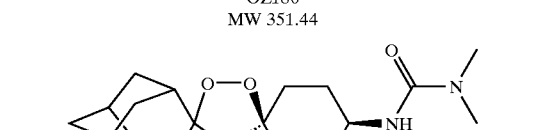
OZ187
MW 350.45
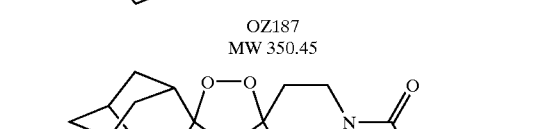
OZ188
MW 378.46
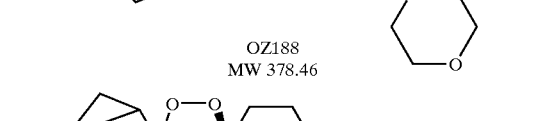
OZ189
MW 391.50
OZ Series 22 (OZ190–OZ198)
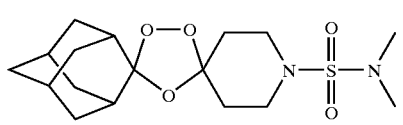
OZ190
MW 372.48
-continued
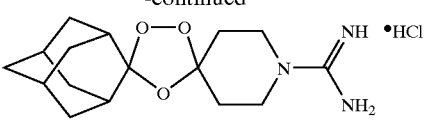
OZ191
MW 343.85
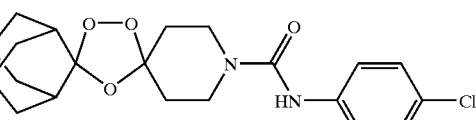
OZ192
MW 418.91
OZ193
MW 374.45
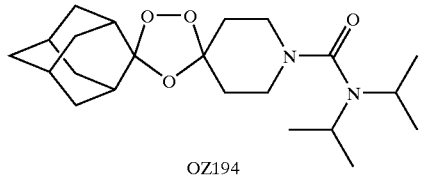
OZ194
MW 392.53
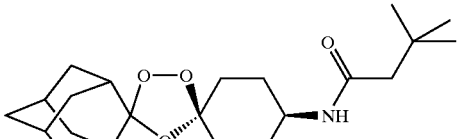
OZ195
MW 377.52
OZ196
MW 379.45
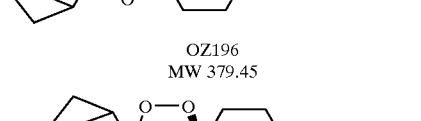
OZ197
MW 375.46
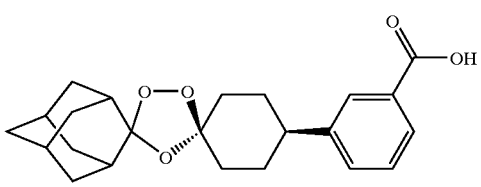
OZ198
MW 384.47

OZ Series 23 (OZ199–OZ207)
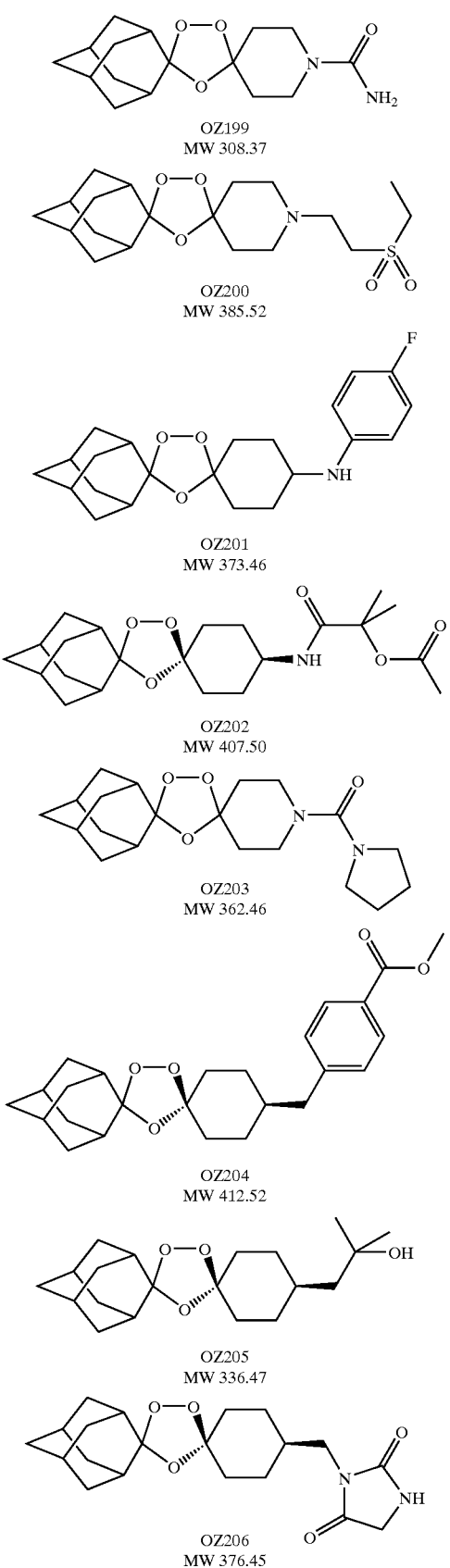
OZ199 MW 308.37
OZ200 MW 385.52
OZ201 MW 373.46
OZ202 MW 407.50
OZ203 MW 362.46
OZ204 MW 412.52
OZ205 MW 336.47
OZ206 MW 376.45
-continued
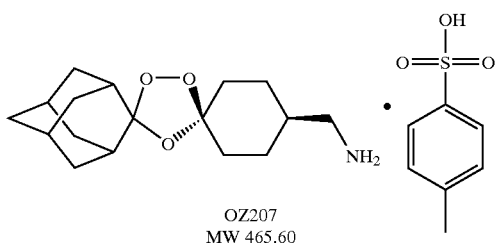
OZ207 MW 465.60
OZ Series 24 (OZ208–OZ216)
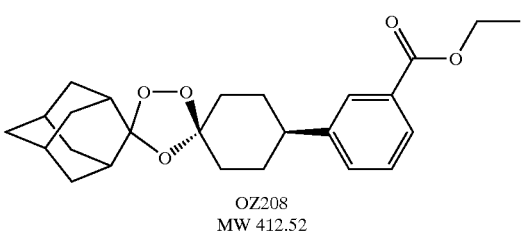
OZ208 MW 412.52
OZ209 MW 389.51
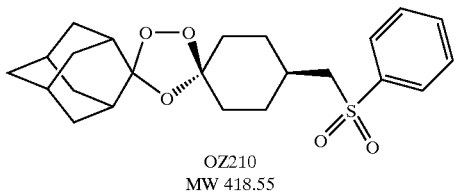
OZ210 MW 418.55
OZ211 MW 344.45
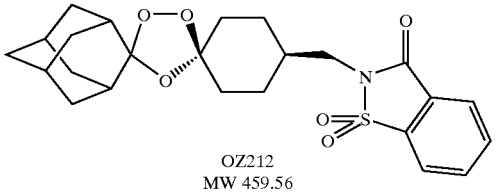
OZ212 MW 459.56
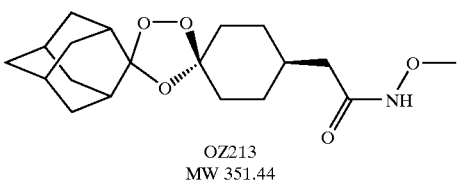
OZ213 MW 351.44

-continued
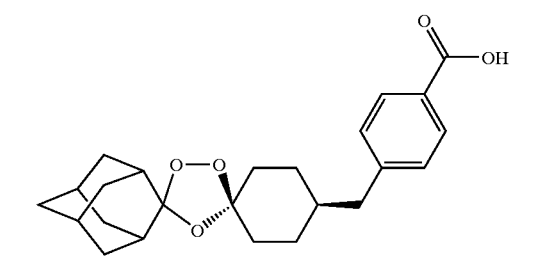
OZ214
MW 398.49
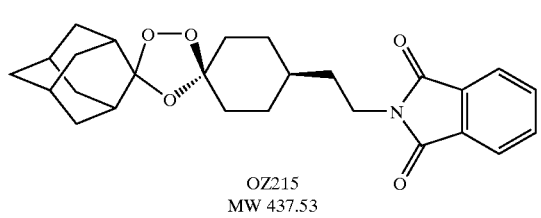
OZ215
MW 437.53
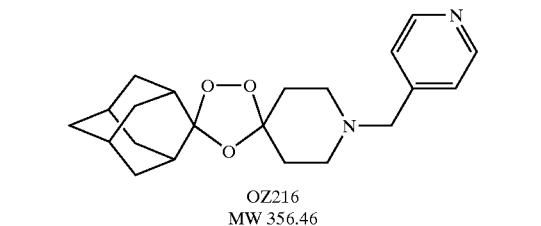
OZ216
MW 356.46
OZ Series 25 (OZ217–OZ225)
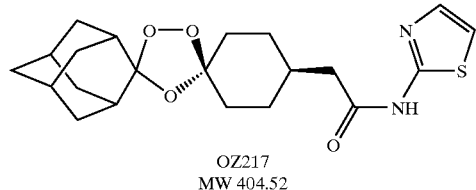
OZ217
MW 404.52
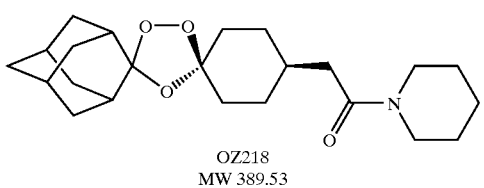
OZ218
MW 389.53
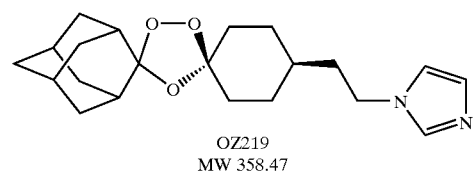
OZ219
MW 358.47
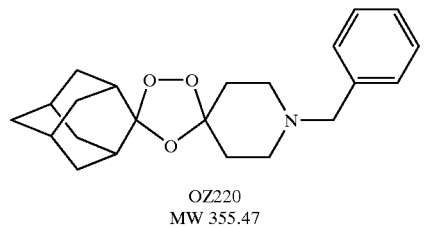
OZ220
MW 355.47
-continued
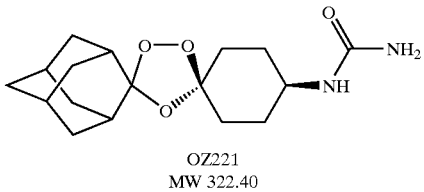
OZ221
MW 322.40
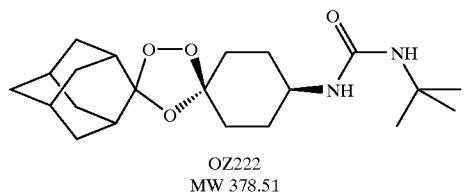
OZ222
MW 378.51
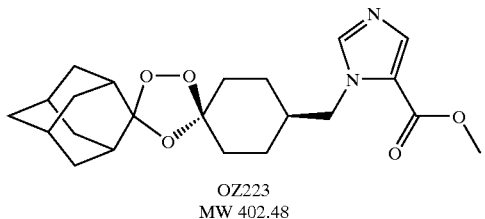
OZ223
MW 402.48
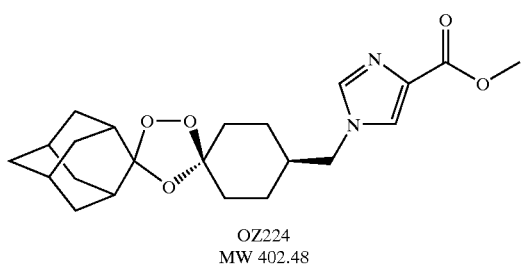
OZ224
MW 402.48
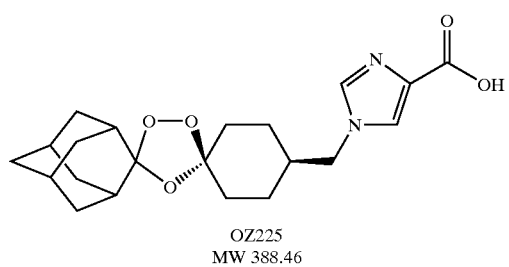
OZ225
MW 388.46
OZ Series 26 (OZ226–OZ234)
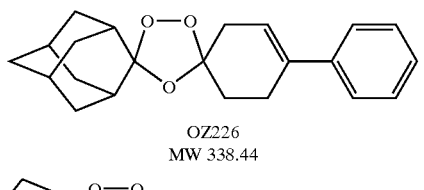
OZ226
MW 338.44
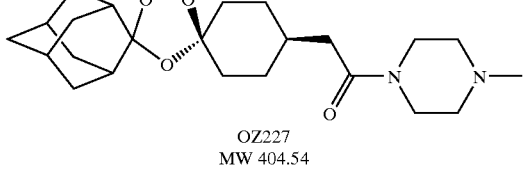
OZ227
MW 404.54

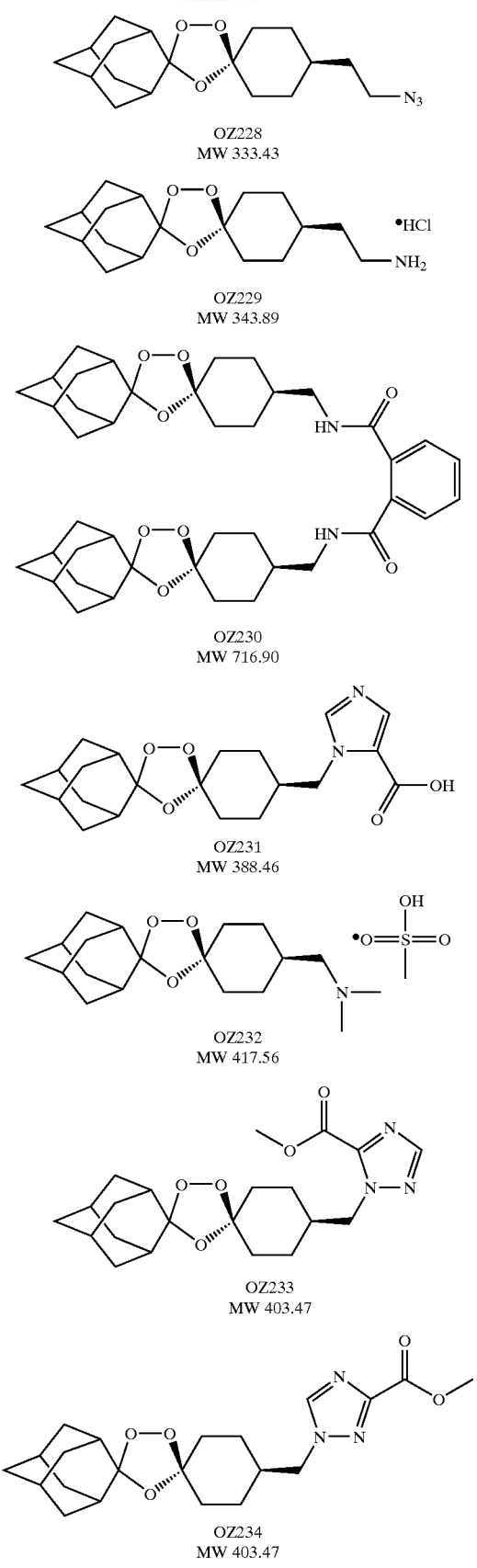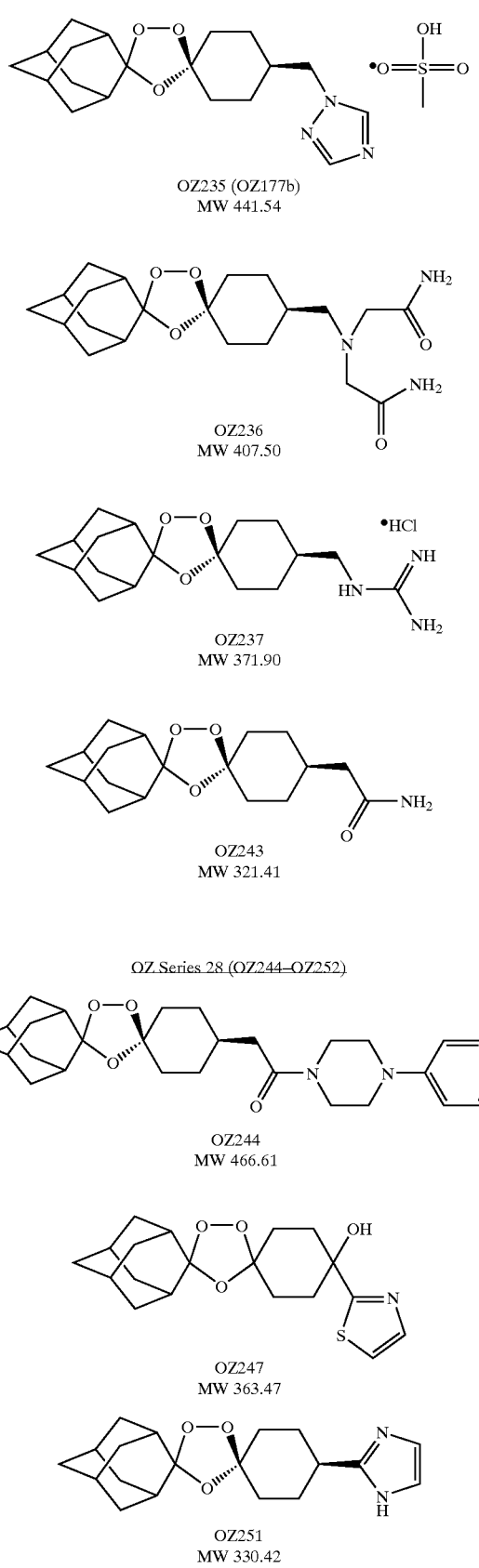

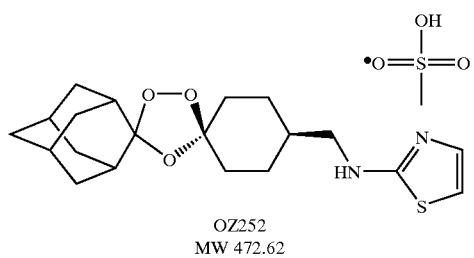
OZ252
MW 472.62
OZ Series 29 (OZ253–OZ261)
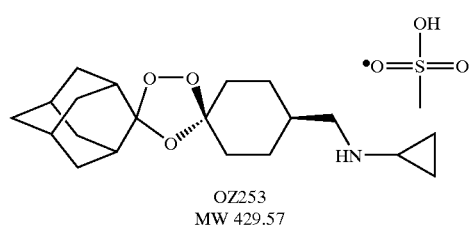
OZ253
MW 429.57
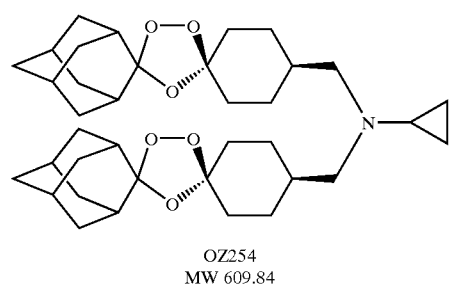
OZ254
MW 609.84
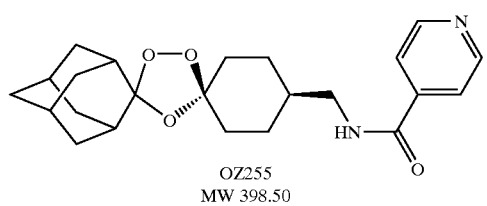
OZ255
MW 398.50
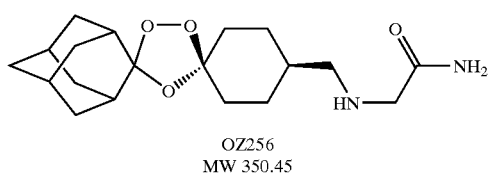
OZ256
MW 350.45
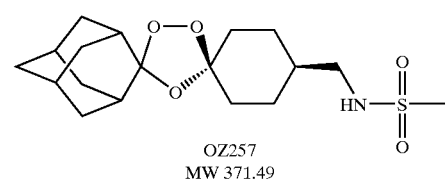
OZ257
MW 371.49
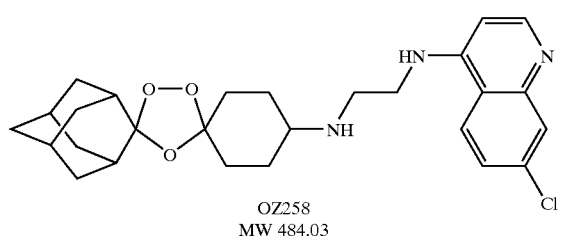
OZ258
MW 484.03
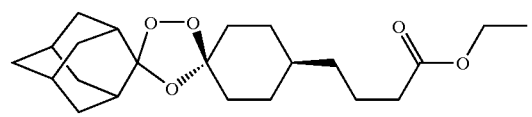
OZ260
MW 378.50
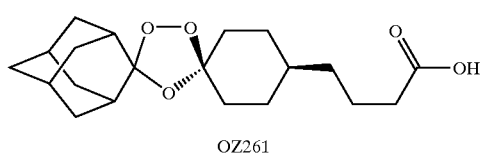
OZ261
MW 350.45
OZ Series 30 (OZ262–OZ270)
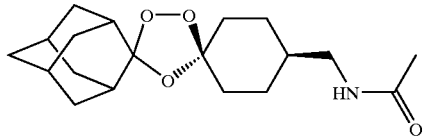
OZ262
MW 335.44
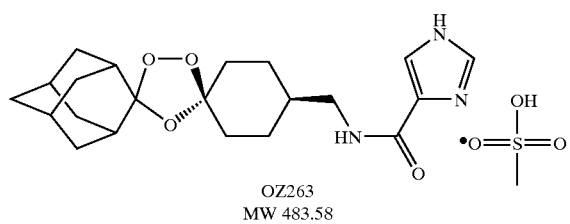
OZ263
MW 483.58
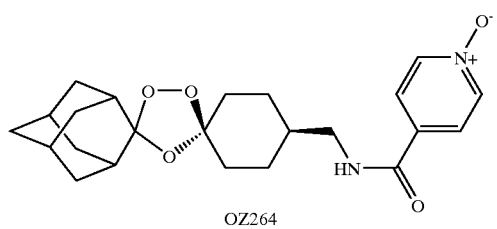
OZ264
MW 414.49
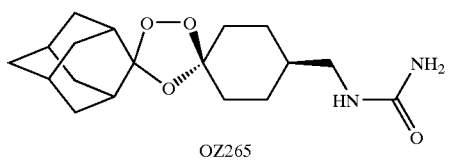
OZ265
MW 336.43
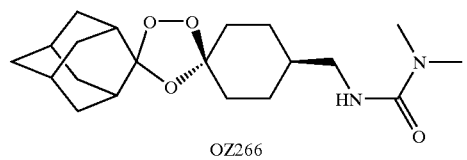
OZ266
MW 364.48
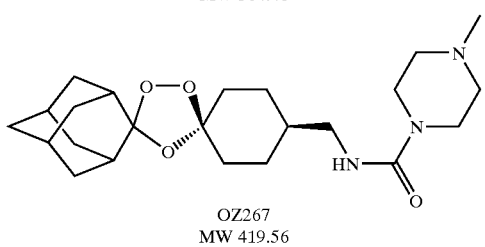
OZ267
MW 419.56

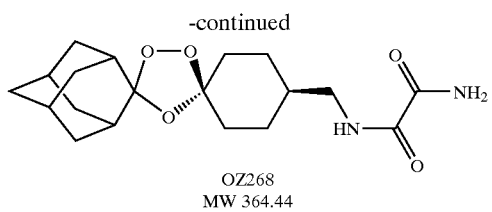
OZ268
MW 364.44
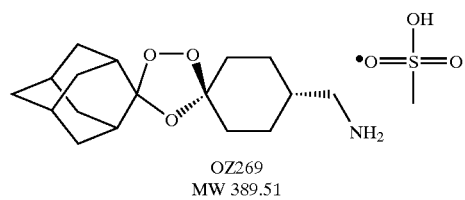
OZ269
MW 389.51
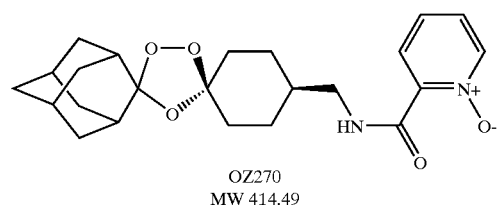
OZ270
MW 414.49
OZ Series 31 (OZ271–OZ279)
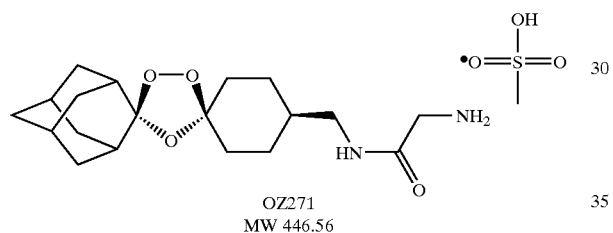
OZ271
MW 446.56
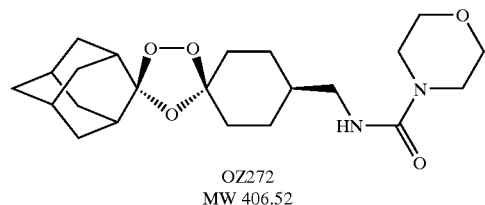
OZ272
MW 406.52
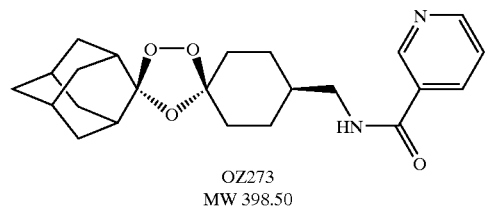
OZ273
MW 398.50
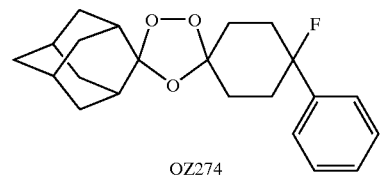
OZ274
MW 358.45
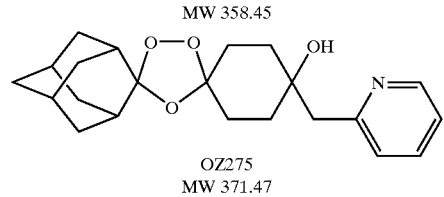
OZ275
MW 371.47
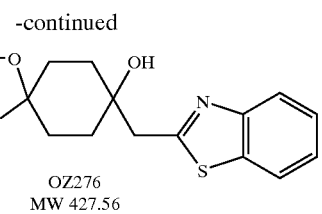
OZ276
MW 427.56
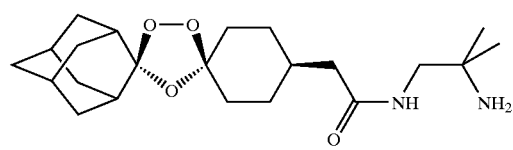
OZ277
MW 564.73
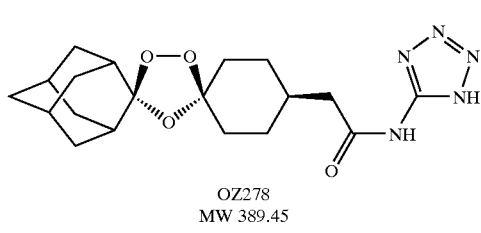
OZ278
MW 389.45
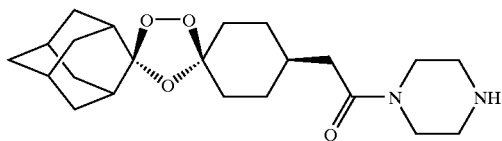
OZ279
MW 562.72
OZ Series 32 (OZ280–OZ288)
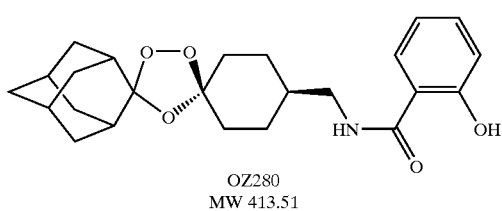
OZ280
MW 413.51

-continued
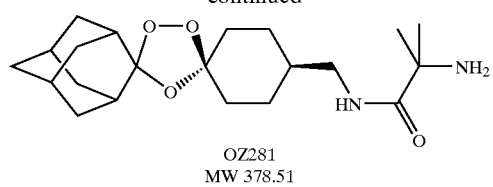
OZ281
MW 378.51
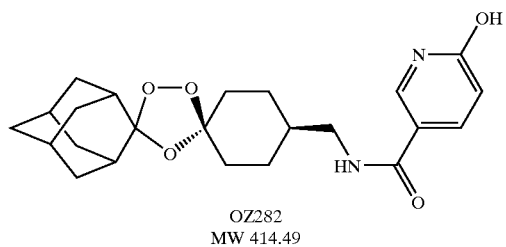
OZ282
MW 414.49
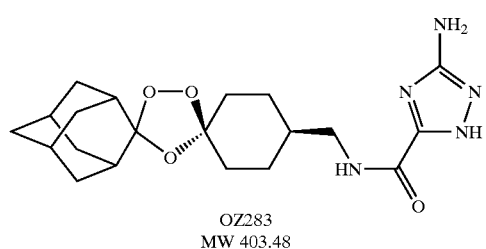
OZ283
MW 403.48
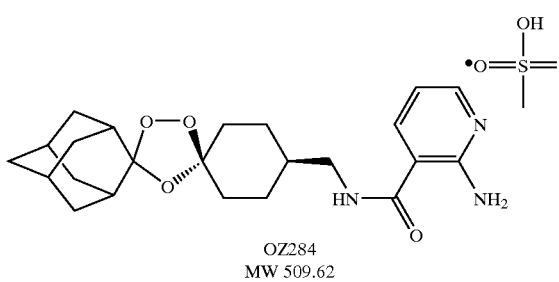
OZ284
MW 509.62
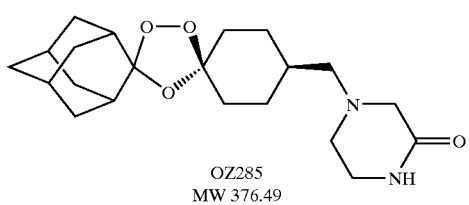
OZ285
MW 376.49
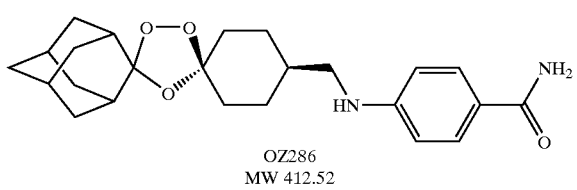
OZ286
MW 412.52
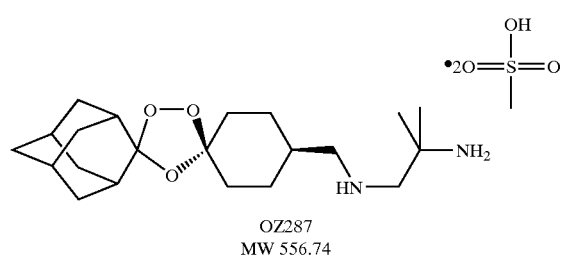
OZ287
MW 556.74
-continued
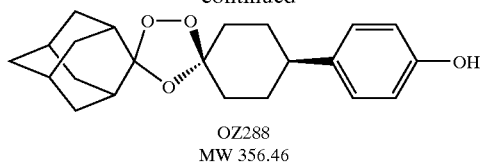
OZ288
MW 356.46
OZ Series 33 (OZ289–OZ297)
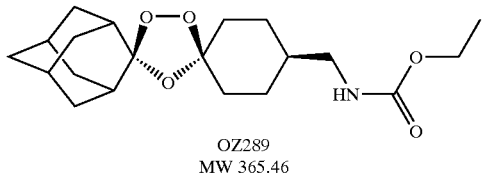
OZ289
MW 365.46
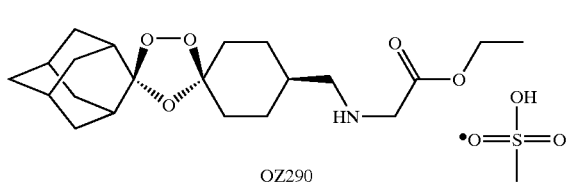
OZ290
MW 475.60
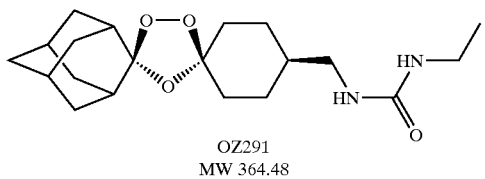
OZ291
MW 364.48
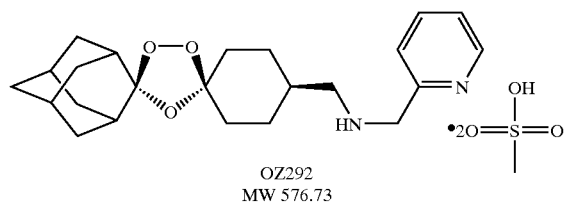
OZ292
MW 576.73
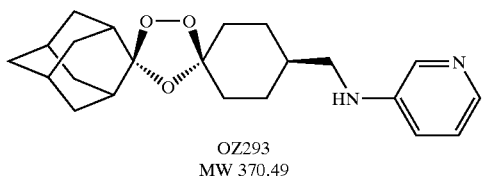
OZ293
MW 370.49
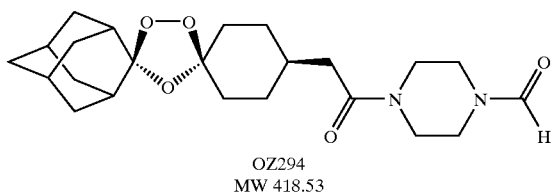
OZ294
MW 418.53
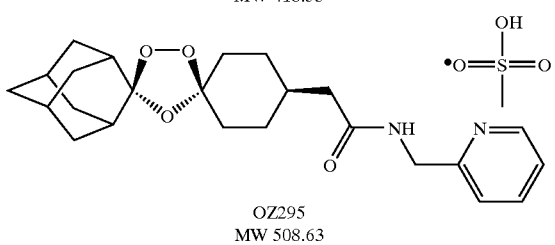
OZ295
MW 508.63

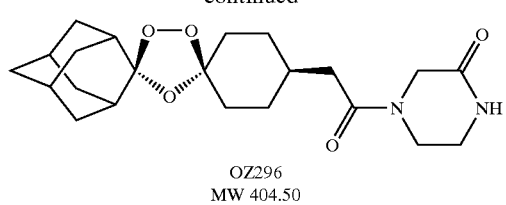
OZ296
MW 404.50
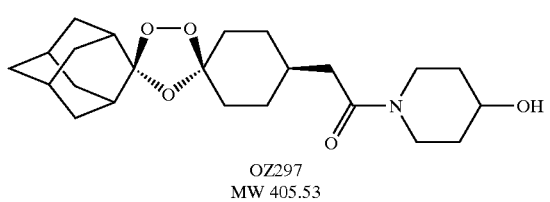
OZ297
MW 405.53
OZ Series 34 (OZ298–OZ306)
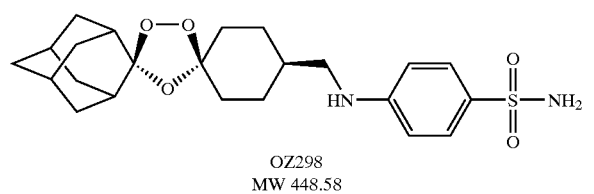
OZ298
MW 448.58
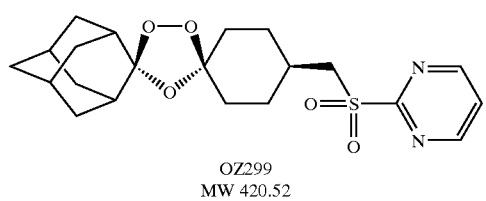
OZ299
MW 420.52
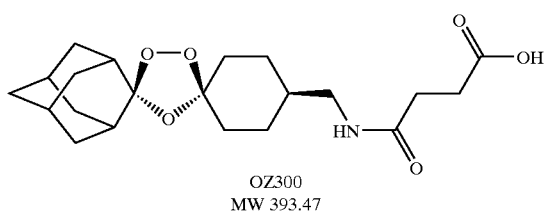
OZ300
MW 393.47
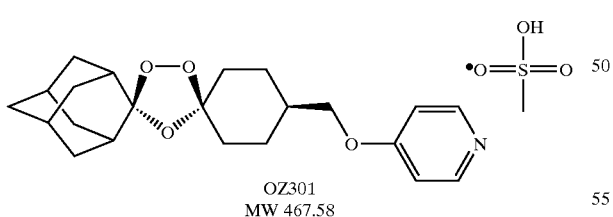
OZ301
MW 467.58
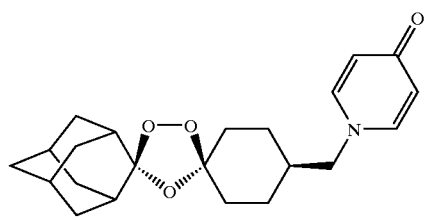
OZ302
MW 371.47
OZ303
MW 390.52
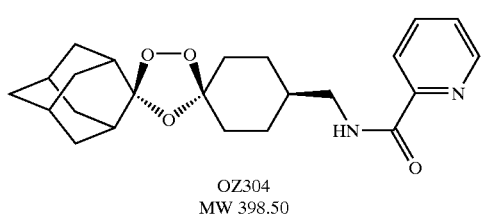
OZ304
MW 398.50
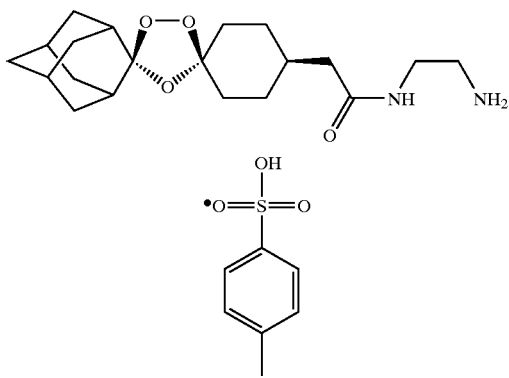
OZ305
MW 536.68
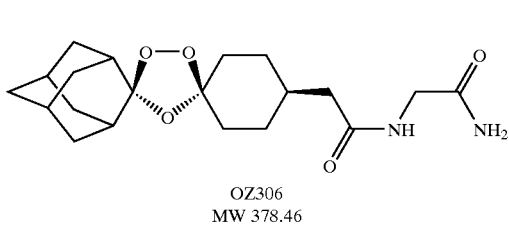
OZ306
MW 378.46
OZ Series 35 (OZ307–OZ315)
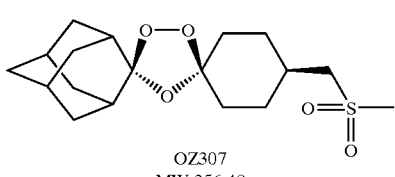
OZ307
MW 356.48
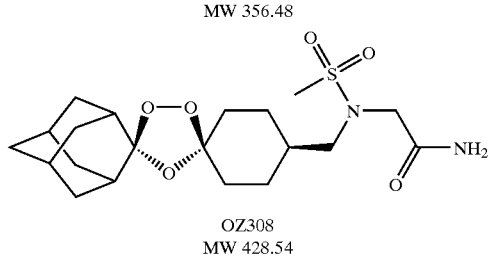
OZ308
MW 428.54

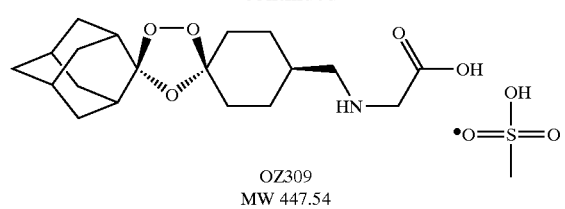
OZ309
MW 447.54
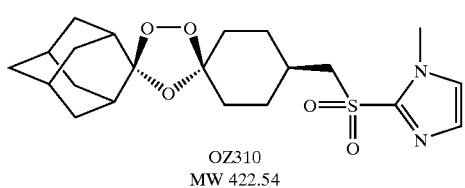
OZ310
MW 422.54
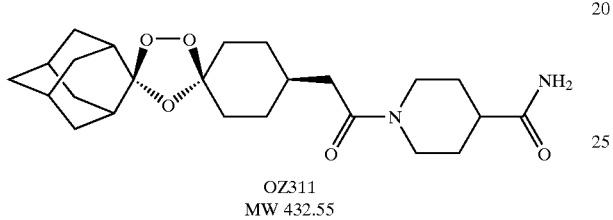
OZ311
MW 432.55
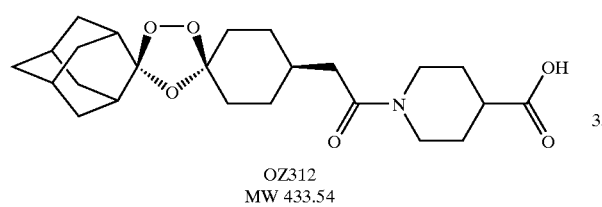
OZ312
MW 433.54
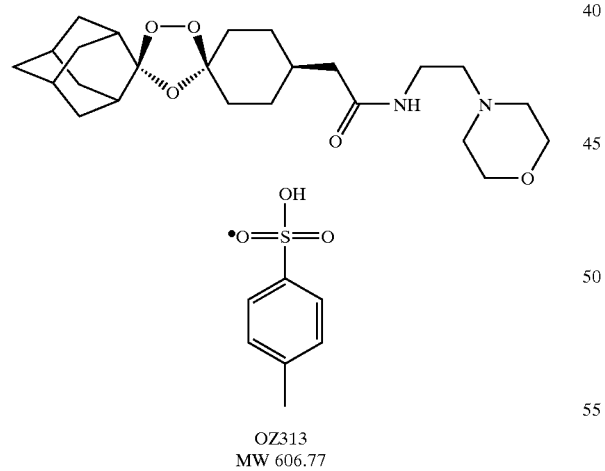
OZ313
MW 606.77
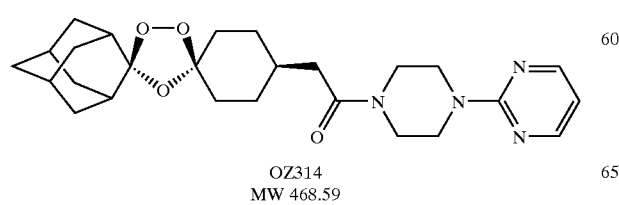
OZ314
MW 468.59
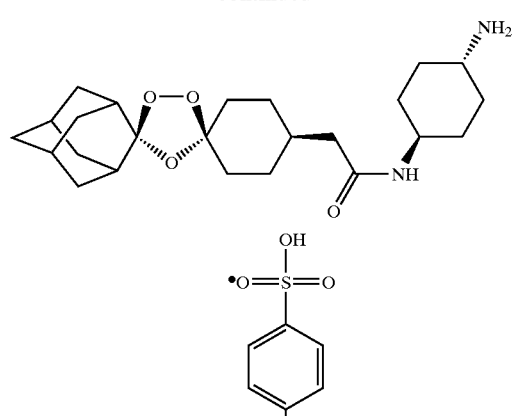
OZ315
MW 590.77
OZ Series 36 (OZ316–OZ324)
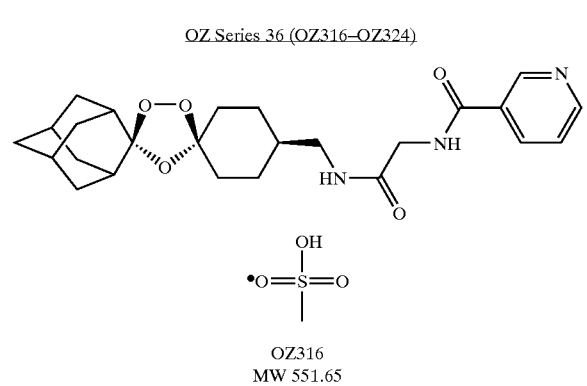
OZ316
MW 551.65
OZ317
MW 404.54
OZ318
MW 565.72

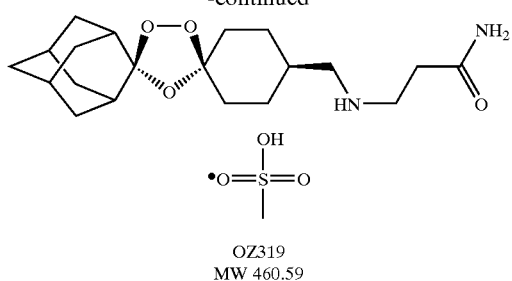
OZ319
MW 460.59
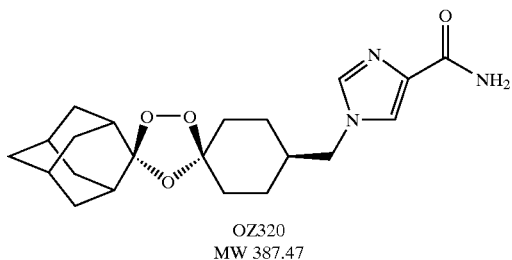
OZ320
MW 387.47
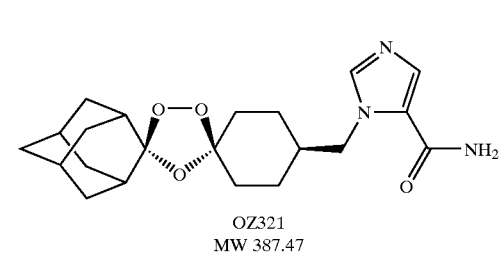
OZ321
MW 387.47
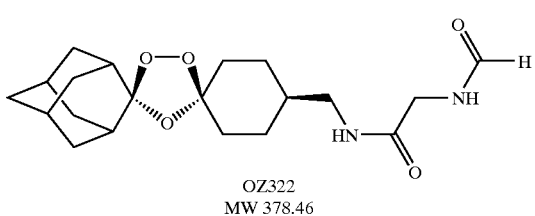
OZ322
MW 378.46
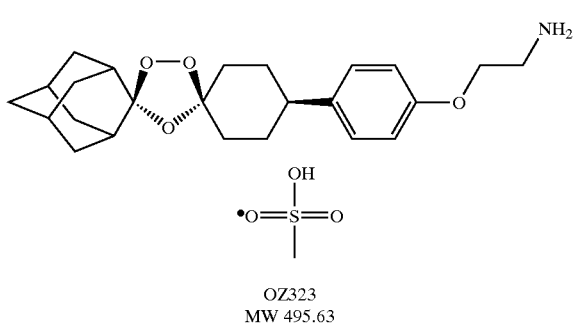
OZ323
MW 495.63
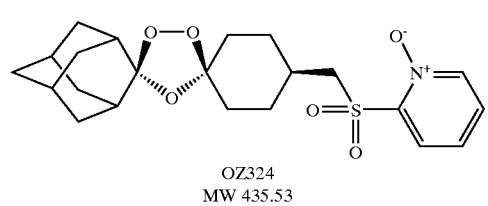
OZ324
MW 435.53
OZ Series 37 (OZ325–OZ333)
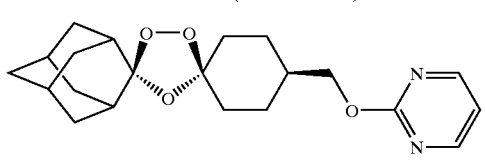
OZ325
MW 468.56
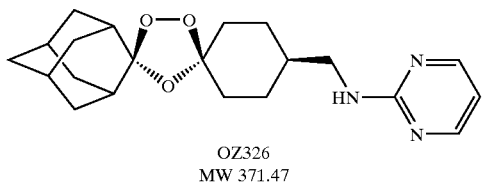
OZ326
MW 371.47
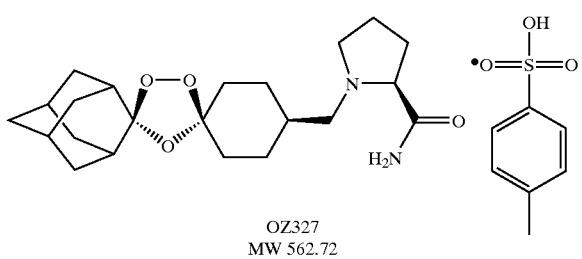
OZ327
MW 562.72
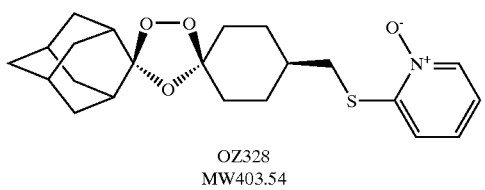
OZ328
MW 403.54
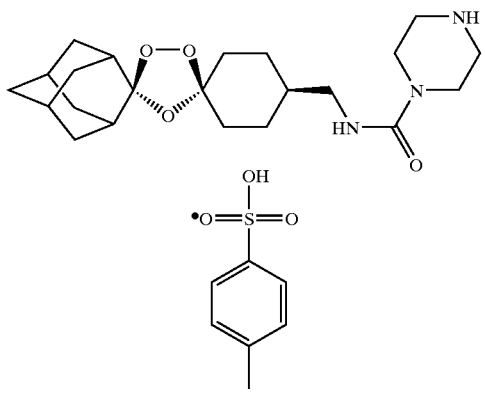
OZ329
MW 577.73
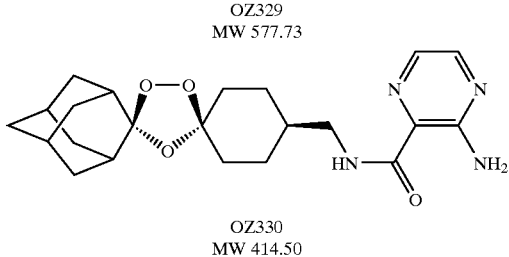
OZ330
MW 414.50

-continued
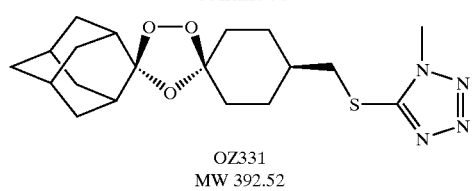
OZ331
MW 392.52
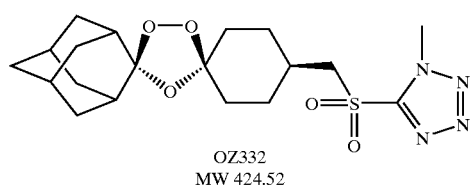
OZ332
MW 424.52
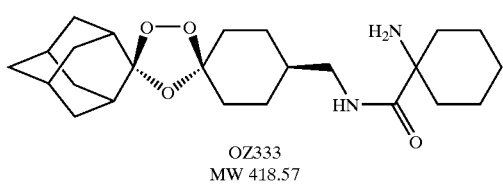
OZ333
MW 418.57
OZ Series 38 (OZ334–OZ342)
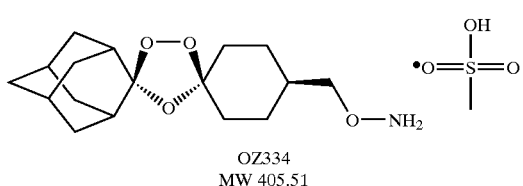
OZ334
MW 405.51
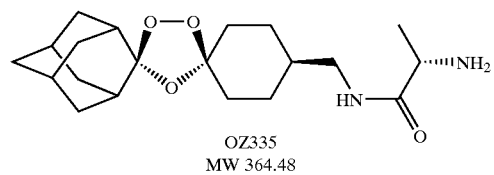
OZ335
MW 364.48
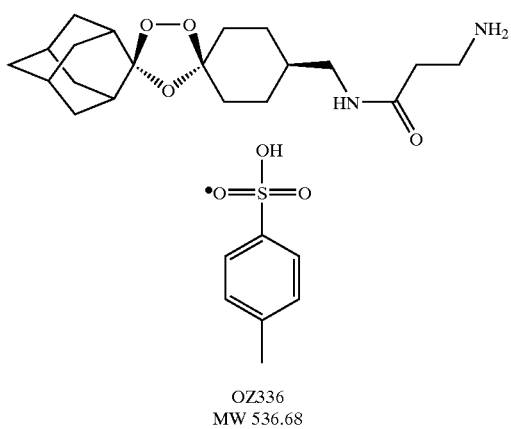
OZ336
MW 536.68
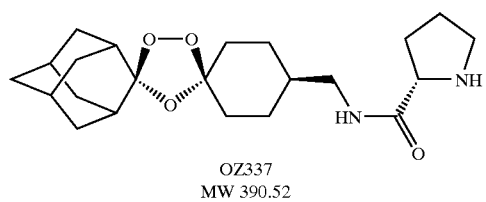
OZ337
MW 390.52
-continued
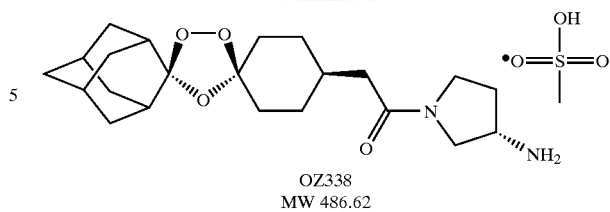
OZ338
MW 486.62
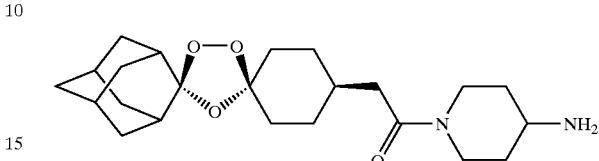
OZ339
MW 576.75
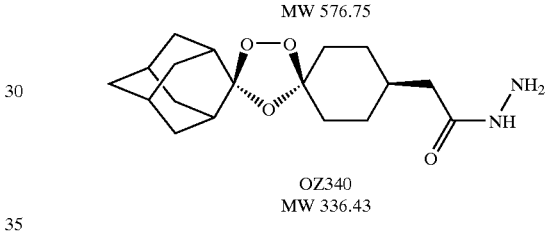
OZ340
MW 336.43
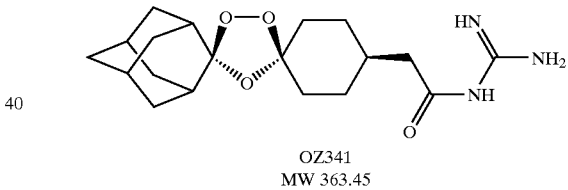
OZ341
MW 363.45
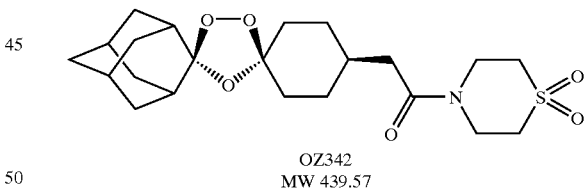
OZ342
MW 439.57
OZ Series 39 (OZ343–OZ351)
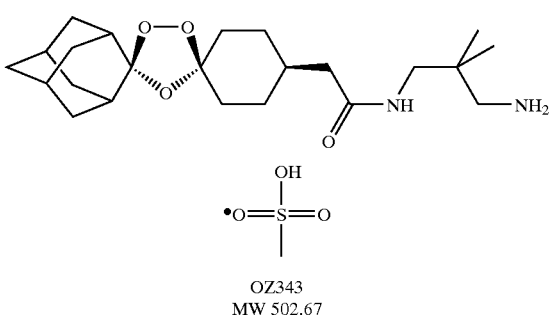
OZ343
MW 502.67

-continued
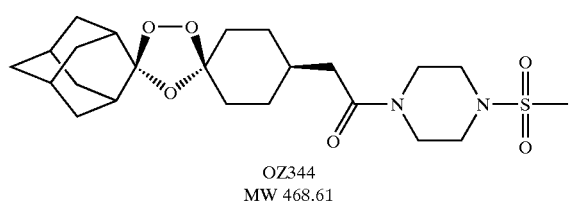
OZ344
MW 468.61
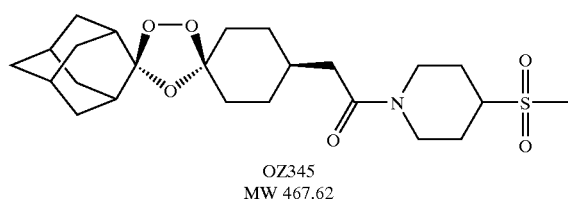
OZ345
MW 467.62
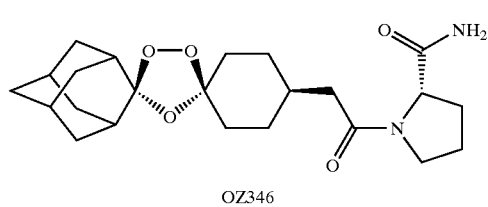
OZ346
MW 418.53
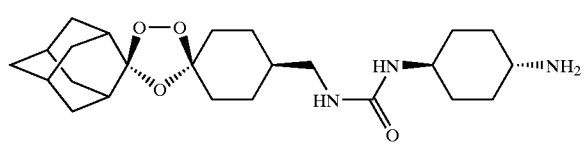
OZ347
MW 605.79
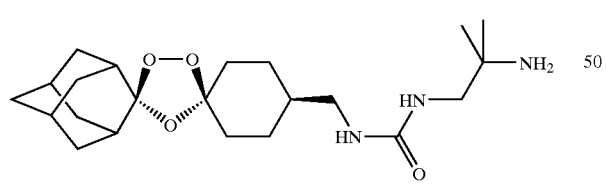
OZ348
MW 579.75
-continued
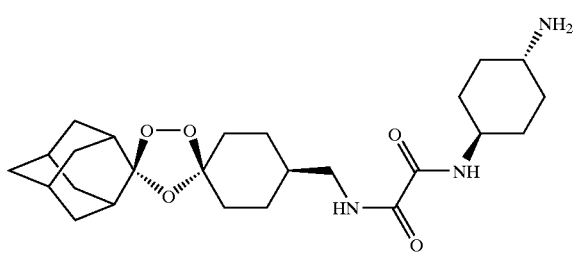
OZ349
MW 633.80
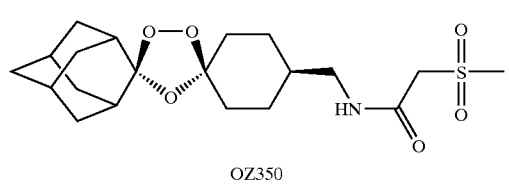
OZ350
MW 413.53
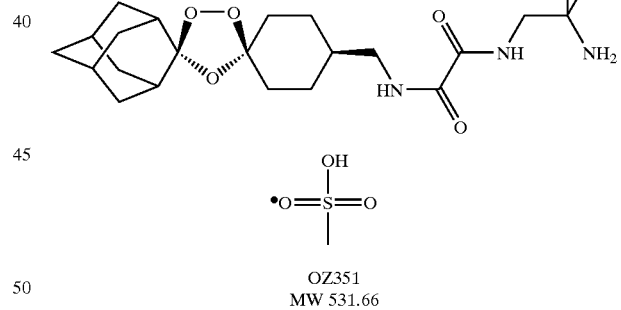
OZ351
MW 531.66
OZ Series 40 (OZ352–OZ360)
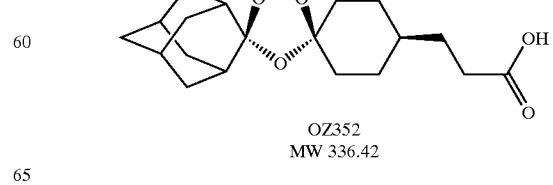
OZ352
MW 336.42

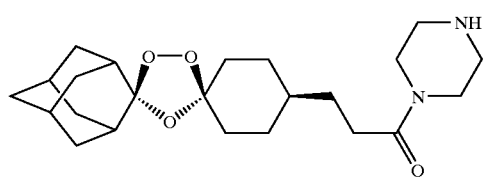
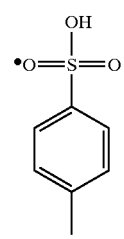
OZ353
MW 576.74
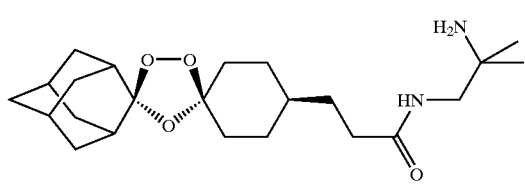
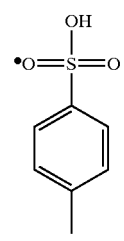
OZ354
MW 578.76
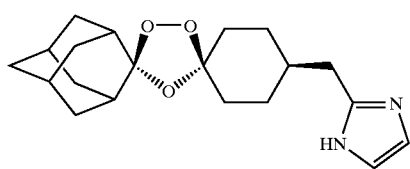
OZ355
MW 344.45
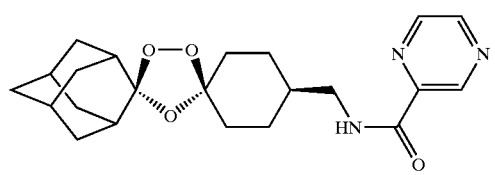
OZ356
MW 399.48
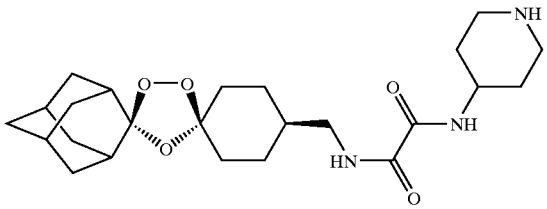
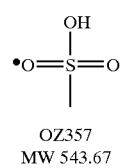
OZ357
MW 543.67
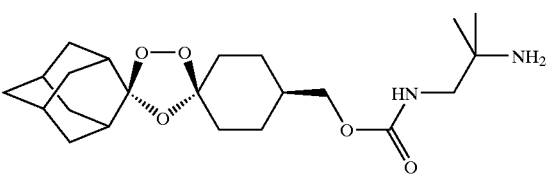
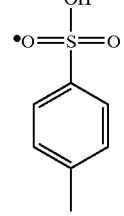
OZ358
MW 580.73
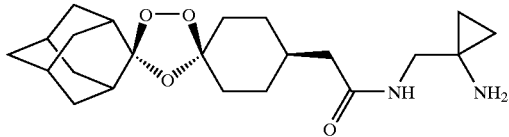
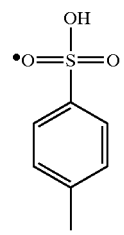
OZ359
MW 562.72
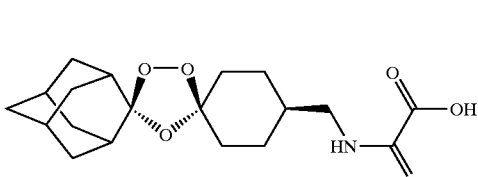
OZ360
MW 365.42

OZ Series 41 (OZ361–OZ369)
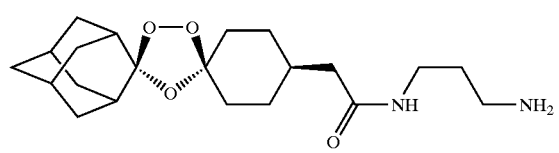
OZ361
MW 550.71
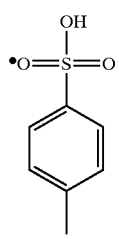
OZ362
MW 451.58
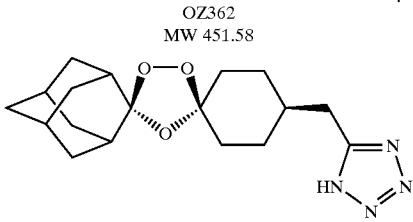
OZ363
MW 346.42
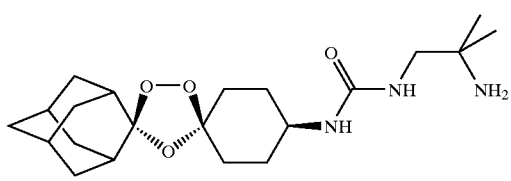
OZ364
MW 565.72
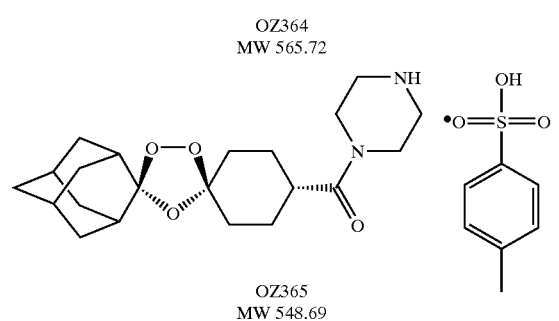
OZ365
MW 548.69
-continued
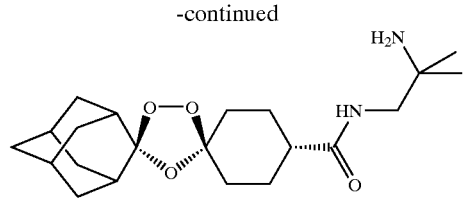
OZ366
MW 550.71
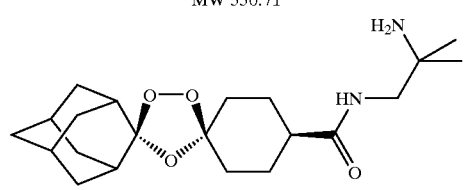
OZ367
MW 550.71
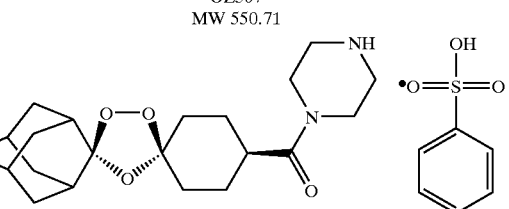
OZ368
MW 548.69
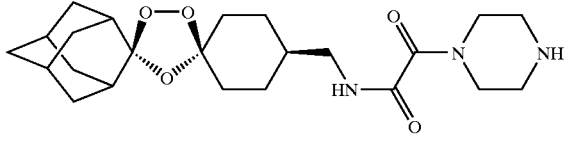
OZ369
MW 529.65
The prototype trioxolanes of this invention are OZ03 and OZ05. Preferred compounds identified thus far include OZ03, OZ05, OZ11, OZ25, OZ27, OZ61, OZ71, OZ78, OZ127, OZ145, OZ156, OZ163, OZ175, OZ177, OZ179, OZ181, OZ189, OZ205, OZ207, OZ209, OZ210, OZ219, OZ227, OZ229, OZ235, OZ255, OZ256, OZ257, OZ263, OZ264, OZ265, OZ266, OZ267, OZ268, OZ269, OZ270, OZ271, OZ277, OZ281, OZ279, OZ288, OZ289, OZ290, OZ296, OZ297, OZ298, OZ301, OZ305, OZ309, OZ315, OZ317 OZ319, OZ320, OZ323, OZ329, OZ333, OZ335, OZ336, OZ337, OZ338, OZ339, OZ343, OZ349, OZ351, OZ353, OZ354, OZ357, OZ358, OZ359, OZ365, and OZ368. The most preferred compounds are OZ78, OZ163, OZ181, OZ207, OZ209, OZ255, OZ256, OZ257, OZ263, OZ264, OZ267, OZ271, OZ277, OZ279, OZ301, OZ305, OZ315, OZ317, OZ319, OZ323, OZ329, OZ338, OZ339, OZ349, OZ351, OZ354, OZ357, OZ359, and OZ368, with OZ277 and OZ279 being the best of those compounds identified thus far. In general, the highest in vitro potency against malarial parasites is obtained for trioxolanes functionalized or substituted at the 4-position of the spirocyclohexyl ring. As a general rule, non-symmetrical, achiral trioxolanes are also preferred.

Notable features of these spiro and dispiro 1,2,4-trioxolanes in comparison to the artemisinin semisynthetic derivatives are their structural simplicity and ease of synthesis. For example, dispiro trioxolanes may be easily synthesized by the coozonolysis of the O-methyl oximes of cycloalkanones in the presence of the requisite cycloalkanone derivatives according to the method of Griesbaum et al. (1997a; 1997b) as illustrated below for the symmetrical dispiro cyclohexyl trioxolane:

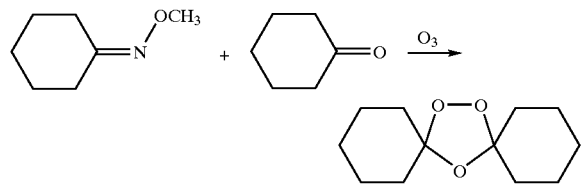

If yields are low in this coozonolysis reaction, yields can improve dramatically when the O-methyloxime and ketone are "reversed." This novel procedure provides a uniquely convenient method to synthesize spiro and dispiro trioxolanes. Advantages of the oxime ether route over the alkene approach include convenient synthesis of starting materials (oxime ethers vs. tetrasubstituted alkenes), higher yield and selectivity of formation of desired trioxolanes by the judicious selection of paired reaction substrates. The trioxolanes may be purified by crystallization or by flash column chromatography. Their structures and purity may be confirmed by analytical HPLC, $^1$H and $^{13}$C NMR, IR, melting point and elemental analysis.

Recently, Griesbaum et al. (1997b) discovered that tetrasubstituted 1,2,4-trioxolanes are conveniently obtained by ozonolysis of O-alkyl ketone oximes in the presence of carbonyl compounds. Formation of a trioxolane from an oxime ether and a ketone is presumed to be a three-step process. The sequence begins by the electrophilic addition of ozone to the oxime double bond to form a primary ozonide. Second, the very unstable primary adduct fragments to a reactive carbonyl oxide driven in part by the concomitant expulsion of the relatively stable methyl nitrite. Third, the carbonyl oxide undergoes a [3+2] cycloaddition with a ketone to give the secondary ozonide or 1,2,4-trioxolane. It remains to be:

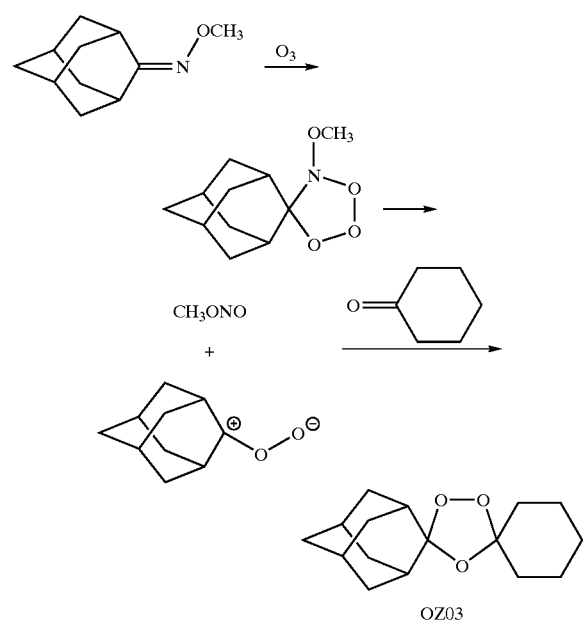

determined whether this is a stepwise or a concerted recombination process.

As illustrated above by the synthesis of OZ03, most of the new dispiro trioxolanes contain a spiroadamantane and can be synthesized by the coozonolysis of adamantanone O-methyl oxime in the presence of the requisite cycloalkanone derivative. The preferred reaction solvents for the coozonolysis reactions are hydrocarbon solvents such as pentane or cyclohexane; more polar solvents tend to decrease the yield of the reaction. When ketones are not readily soluble in pentane or cyclohexane, a mixed solvent (pentane/methylene chloride) or methylene chloride alone may be used. Several factors govern the ratio of oxime ether to ketone. In some reactions, in order to avoid diperoxide (1,2,4,5-tetraoxane) formation, to preclude diozonide formation from diketones, and to promote the reaction with readily pentane soluble ketones, excess ketone (2:1) is used. Most commonly in the discovery synthesis stage, and especially in cases where ketones are not readily soluble in pentane, expensive, or difficult to remove in the reaction workup, a 1:1 ratio of ketone to oxime ether may be used. In large scale trioxolane syntheses, a 1.5-fold excess of oxime ether can be used to achieve higher conversions of ketones into the desired product trioxolanes without causing purification problems.

There are several examples of where post-ozonolysis transformations were used to obtain trioxolane target compounds difficult, or in some cases, impossible to obtain directly (Kashima et al., 1987) by the coozonolysis method. Trioxolane tertiary alcohols OZ90 and

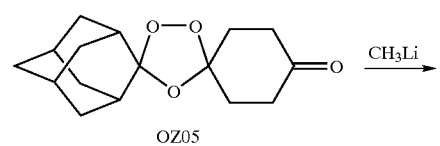

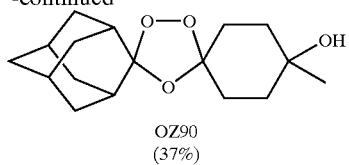

OZ90
(37%)

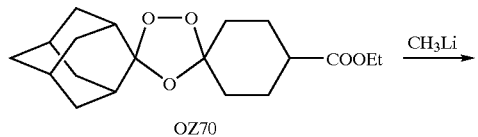

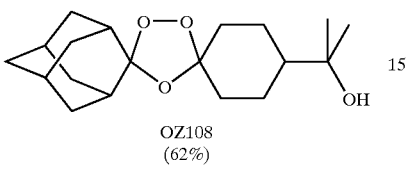

OZ108
(62%)

OZ108 can be obtained by methyllithium treatment of trioxolane ketone OZ05 and trioxolane ester OZ70, respectively. In other reactions, trioxolane lactone OZ17 and trioxolane alcohol OZ32 were obtained by treatment of OZ05 with m-CPBA and sodium borohydride, respectively. In addition, various oxime ethers, hydrazones, ketals, and amines (reductive amination with sodium triacetoxyborohydride) were also obtained from trioxolane ketone OZ05 in good to excellent yields. In the examples noted above, it is evident that troxolane ketone OZ05 is a key intermediate as its ketone functional group provides a convenient means for functional group transformation.

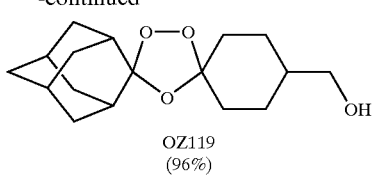

OZ119
(96%)

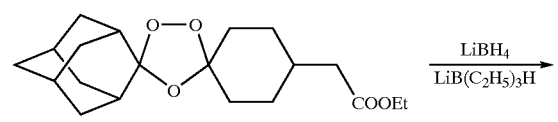

OZ61

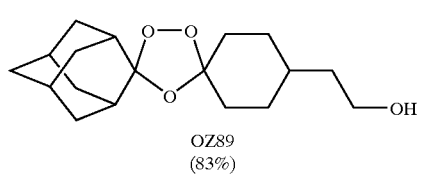

OZ89
(83%)

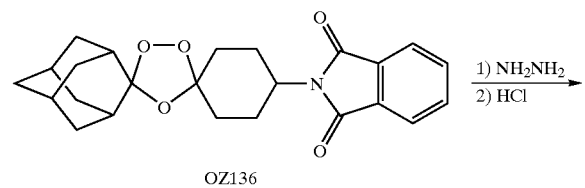

OZ136

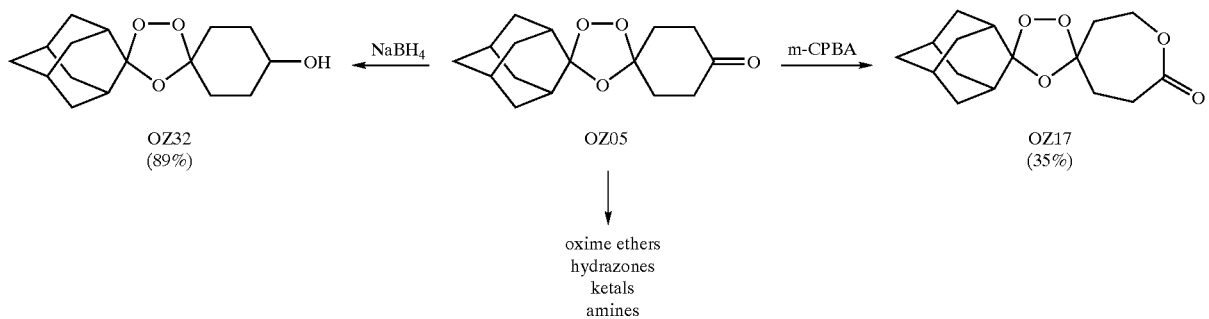

OZ32 (89%) ← NaBH₄ — OZ05 — m-CPBA → OZ17 (35%)

↓ oxime ethers
hydrazones
ketals
amines

Further evidence of the stability of these trioxolanes to reducing agents is shown by the reduction of trioxolane esters OZ70 and OZ61 into their corresponding trioxolane alcohols OZ119 and OZ89 with a mixture of lithium borohydride and lithium triethylborohydride, and the hydrazinolysis of the trioxolane phthalimides OZ136 and

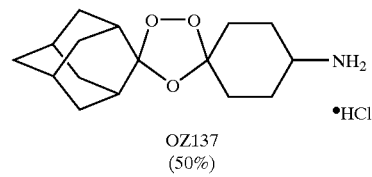

OZ137
(50%)

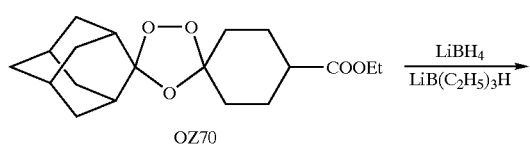

OZ70

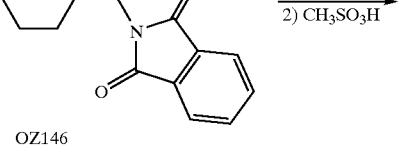

OZ146

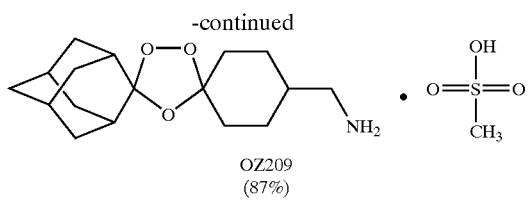

OZ209
(87%)

OZ146 into their corresponding trioxolane amines OZ137 and OZ209.

As shown in the examples below, trioxolane esters can be conveniently converted into their corresponding trioxolane acids.

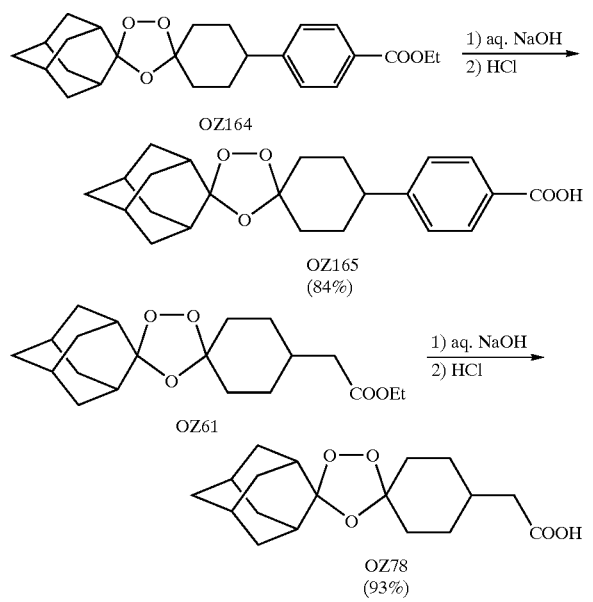

In addition to trioxolane ketone OZ05, trioxolane amine mesylate OZ209, trioxolane ester OZ61 and trioxolane acid OZ78, trioxolane alcohols OZ119 and OZ89 have and will continue to be key intermediates for post-ozonolysis synthetic transformations. A recent example is the

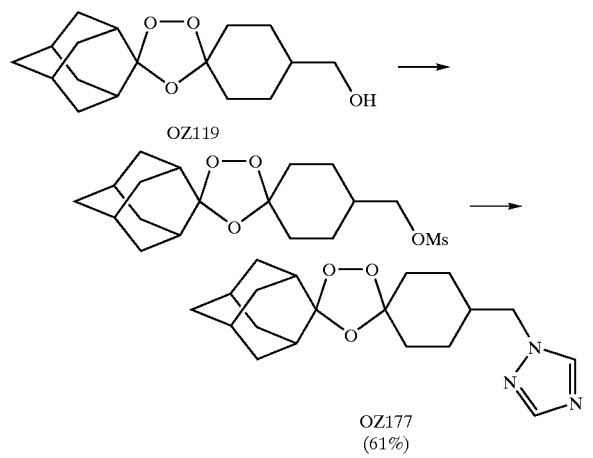

synthesis of trioxolane triazole OZ177 in a reaction between the mesylate derivative of OZ119 and the sodium salt of 1,2,4-triazole.

It has been found that the coozonolysis method using oxime methyl ethers offers a rapid, flexible, and predictable access to structurally diverse trioxolanes. In fact, several key trioxolanes that have served as important building blocks have been prepared in large scale including OZ05 (100 mmol), OZ61 (100 mmol), and OZ146 (60 mmol), with no decrease in reaction yields over the usual 5–10 mmol scale. Furthermore, both OZ61 and OZ146 can be conveniently isolated as white solids by addition of ethanol to the crude reaction mixtures.

Differential scanning calorimetry (DSC) experiments (Cammenga, and Epple, 1995) reveal that these compounds have good thermal stability, comparable to artemisinin. The average Tm, dec was 160±15° C. compared to a Tm, dec of 181° C. for artemisinin. It is presumed that thermal decomposition of these trioxolanes was initiated by formation of a 1,5 diradical produced by homolytic cleavage of the peroxide bond of the trioxolane ring.

Since most of the target trioxolanes contain the symmetrical spiroadamantane structural framework, their stereochemistry is largely a function of the starting material ketone structure or reagents used in post-ozonolysis reactions. For OZ27 and other similarly 1,4-substituted trioxolanes, two achiral diastereomers are possible. However, as exemplified by OZ27, the majority of these trioxolanes were isolated as single achiral diastereomers rather than as mixtures of two achiral diastereomers. For example, in OZ27, no chirality is present since the trioxolane ring and phenyl substituent are in a 1,4 relationship in a six membered ring. Such compounds possess a plane of symmetry.

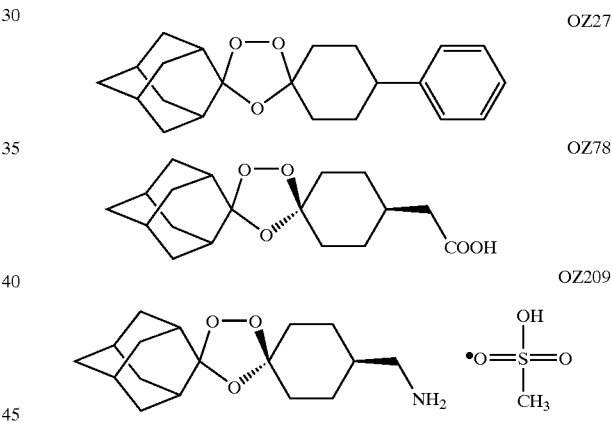

As determined by X-ray crystallography, the assignment of stereochemistry for OZ78, OZ209 and their derivatives was determined to be cis where the peroxide oxygens are in an axial position.

The starting material 2-adamantanone may be obtained from Aldrich Chemical Co. or from TCI American Organic Chemicals or may also be synthesized. Persons skilled in the art can readily ascertain other appropriate means of synthesizing the starting materials and compounds in accordance with this invention.

The Spiro and dispiro trioxolane compositions of the present invention may be generally used for the prophylaxis and treatment of malaria. The trioxolane compositions of the present invention are administered along with a pharmaceutically acceptable carrier. Any pharmaceutically acceptable carrier may be generally used for this purpose, provided that the carrier does not significantly interfere with the stability or bioavailability of the trioxolane compounds of this invention.

The trioxolanes of this invention can be administered in any effectively pharmaceutically acceptable form to warm blooded animals, including human and other animal subjects, e.g. in topical, lavage, oral, suppository, parenteral, or infusible dosage forms, as a topical, buccal, sublingual, or nasal spray or in any other manner effective to deliver the agents. The route of administration will preferably be designed to optimize delivery and/or localization of the agents to target cells.

In addition to the active compounds i.e. the trioxolanes, the pharmaceutical compositions of this invention may contain suitable excipients and auxiliaries which facilitate processing of the active compounds into preparations which can be used pharmaceutically. Oral dosage forms encompass tablets, capsules, and granules. Preparations which can be administered rectally include suppositories. Other dosage forms include suitable solutions for administration parenterally or orally, and compositions which can be administered buccally or sublingually.

The pharmaceutical preparations of the present invention are manufactured in a manner which is itself well known in the art. For example the pharmaceutical preparations may be made by means of conventional mixing, granulating, dragee-making, dissolving, lyophilizing processes. The processes to be used will depend ultimately on the physical properties of the active ingredient used.

Suitable excipients are, in particular, fillers such as sugars for example, lactose or sucrose mannitol or sorbitol, cellulose preparations and/or calcium phosphates, for example, tricalcium phosphate or calcium hydrogen phosphate, as well as binders such as starch, paste, using, for example, maize starch, wheat starch, rice starch, potato starch, gelatin, gum tragacanth, methyl cellulose, hydroxypropylmethylcellulose, sodium carboxymethylcellulose, and/or polyvinyl pyrrolidone. If desired, disintegrating agents may be added, such as the above-mentioned starches as well as carboxymethyl starch, cross-linked polyvinyl pyrrolidone, agar, or alginic acid or a salt thereof, such as sodium alginate. Auxiliaries are flow-regulating agents and lubricants, for example, such as silica, talc, stearic acid or salts thereof, such as magnesium stearate or calcium stearate and/or polyethylene glycol. Oral dosage forms may be provided with suitable coatings which, if desired, may be resistant to gastric juices.

For this purpose concentrated sugar solutions may be used, which may optionally contain gum arabic, talc, polyvinylpyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, dyestuffs and pigments may be added to the tablet coatings, for example, for identification or in order to characterize different combination of compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition stabilizers may be added. Possible pharmaceutical preparations which can be used rectally include, for example, suppositories, which consist of a combination of the active compounds with the suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base material include for example liquid triglycerides, polyethylene glycols, or paraffin hydrocarbons.

Suitable formulations for parenteral administration include aqueous solutions of active compounds in water-soluble or water-dispersible form. In addition, suspensions of the active compounds as appropriate oily injection suspensions may be administered. Suitable lipophilic solvents or vehicles include fatty oils for example, sesame oil, or synthetic fatty acid esters, for example, ethyl oleate or triglycerides. Aqueous injection suspensions may contain substances which increase the viscosity of the suspension, including for example, sodium carboxymethyl cellulose, sorbitol and/or dextran. Such compositions may also comprise adjuvants such as preserving, wetting, emulsifying, and dispensing agents. They may also be sterilized, for example, by filtration through a bacteria-retaining filter, or by incorporating sterilizing agents into the compositions. They can also be manufactured in the form of sterile solid compositions which can be dissolved or suspended in sterile water, saline, or other injectable medium prior to administration.

In addition to administration with conventional carriers, active ingredients may be administered by a variety of specialized delivery drug techniques which are known to those of skill in the art, such as portable infusion pumps.

The trioxolane compositions of the present invention are administered along with a pharmaceutically acceptable carrier in an amount sufficient to prevent malarial infection and/or treat an active infection. The trioxolane compounds of this invention have extremely low toxicity and a low degree of side effects even at high doses. The dosing range of the trioxolane compositions will vary depending on a number of factors, such as whether it is used for prophylaxis or treatment of an active infection, route of administration, dosing schedule, etc. In general, the therapeutic dose of trioxolane may range between about 0.1–1000 mg/kg/day, with between about 1–100 mg/kg/day being preferred. The foregoing doses may be administered as a single dose or may be divided into multiple doses for administration. The trioxolane compositions may be administered once to several times daily. For malaria prevention, a typical dosing schedule could be, for example, 2.0–1000 mg/kg weekly beginning 1–2 weeks prior to malaria exposure taken up until 1–2 weeks post-exposure.

The spiro and dispiro trioxolanes of this invention may be administered as any pharmaceutically effective salt form. Such salts are well known in the art and include, but are not limited to acetate, adipate, alginate, citrate, aspartate, benzoate, benzene sulfonate, bisulfate, butyrate, camphorate, camphor sulfonate, digluconate, glycerophosphate, hemisulfate, heptanoate, hexanoate, fumarate, hydrochloride, hydrobromide, hydroiodide, 2-hydroxyethansulfonate (isothionate), lactate, maleate, methane sulfonate, nicotinate, 2-naphthalene sulfonate, oxalate, palmitoate, pectinate, persulfate, 3-phenylpropionate, picrate, pivalate, propionate, succinate, tartrate, thiocyanate, phosphate, glutamate, bicarbonate, p-toluene sulfonate and undecanoate salts. Preferred salts are those that increase the bioavailability of the trioxolane compounds. This will depend upon a number of factors, including the chemical structure of the trioxolane, the carrier to which it is incorporated, the route of administration, etc.

The spiro and dispiro trioxolanes of this invention have been found to be effective in the treatment of schistosomiasis. Schistosomiasis ranks second behind malaria in terms of socioeconomic and public health importance in tropical and subtropical areas. The disease is endemic in 74 developing countries, infecting more than 200 million people in rural agricultural and peri-urban areas. An estimated 500–600 million people worldwide are at risk from the disease.

The major forms of human schistosomiasis are caused by five species of water-borne flatworm, or blood flukes, called schistosomes. One of these species is *Schistosoma mansoni*, which has been reported in 53 countries in Africa, the Eastern Mediterranean, the Caribbean, and South America. The parasites enter the body through contact with infested surface water, primarily among people engaged in agriculture and fishing. The parasites normally infect the host during the cercaria, or larval stage. Once inside the host, the cercaria develop into adults or schistosomes.

Current treatments for schistosomiasis have focused primarily on prophylaxis, i.e. prevention of host infection by cercaria. Currently, praziquantel is the most widely used drug for treatment of schistosomiasis. While artemether has demonstrated activity in the prophylaxis of schistosomiasis, it has not shown any activity against adult *S. mansoni*.

It has now been unexpectedly discovered that the spiro and dispiro trioxolanes of this invention are active against both cercaria and adult *S. mansoni*, *S. japonicum* when administered in the dosages and manner outlined above with respect to treatment of malarial parasites. It is also believed the trioxolanes of this invention will be active against *S. haematobium*. Preferred compounds identified for use in the treatment of schistosomiasis include OZ05, OZ11, OZ23, OZ25, OZ28, OZ32, OZ71, OZ78, OZ89, OZ90, OZ119, OZ145, OZ179, OZ205, OZ207, and OZ209. Most preferred compounds are OZ78, OZ207, and OZ209. Preferred dosing levels of the spiro and dispiro trioxolanes are about 100–200 mg/kg/day orally. The prototype trioxolanes of this invention are OZ03 and OZ05.

The spiro and dispiro trioxolanes of this invention may also have effectiveness in the treatment of cancer. Compounds having an endoperoxide moiety that is reactive with heme and iron have shown an ability to kill cancer cells. (See e.g. U.S. Pat. No. 5,578,637, the disclosure of which is hereby incorporated by reference). As noted with respect to artemisinin, trioxolanes' mechanism of action against malarial parasites is based on the ability of trioxolane compounds to react with the iron in free heme molecules in malaria parasites, with the generation of free radicals leading to cellular destruction. Similarly, trioxolanes are selective against cancer cells due to the higher concentration of transferrin receptors on cancer cell membranes that pick up iron at a higher rate than normal cells. In the presence of the trioxolanes of this invention, the cancer cells will accumulate high concentrations of free radicals, leading to cell death. For cancer treatment, the trioxolanes of this invention may be administered in the doses and manner outlined above.

Other drugs besides trioxolanes which are compatible with the carrier ingredients may also be incorporated into the carrier. Such drugs may be readily ascertained by those of ordinary skill in the art and may include, for instance, antibiotics, other antimalarials, antiinflammatory agents, etc.

It is understood that the present invention contemplates the use of not only the above-stated trioxolane compounds themselves, but their prodrugs which metabolize to the compound and the analogues and biologically active salt forms thereof, as well as optical isomers which provide the same pharmaceutical results.

The following examples are offered to illustrate but not limit the invention. Thus, they are presented with the understanding that various formulation modifications as well as method of delivery modifications may be made and still be within the spirit of the invention.

EXAMPLE 1

General Procedure for the Preparation of 1,2,4-Trioxolanes

Synthesis of O-methyl 2-adamantanone oxime (representative procedure). To a solution of 2-adamantanone (4.51 g, 30 mmol) in methanol (30 ml) were added pyridine (4.5 ml) and methoxylamine hydrochloride (3.76 g, 45.0 mmol). The reaction mixture was stirred at room temperature for 48 h, concentrated in vacuo, and diluted with $CH_2Cl_2$ (50 ml) and water (50 ml). The organic layer was separated, and the aqueous layer extracted with $CH_2Cl_2$ (30 ml). The combined organic extracts were washed with 1M HCl (30 ml×2) and saturated aqueous NaCl (30 ml), and dried over $MgSO_4$. Evaporation in vacuo afforded O-methyl 2-adamantanone oxime (4.77 g, 89%) as a colorless solid. mp 70–71° C.; $^1H$ NMR (300 MHz, $CDCl_3$) δ1.60–2.10 (m, 12H), 2.54 (s, 1H), 3.47 (s, 1H), 3.82 (s, 3H).

Ref: Corey, E. J.; Niimura, K.; Konishi, Y.; Hashimoto, S.; Hamada, Y. A New Synthetic Route to Prostaglandins. *Tetrahedron Lett*. 1986, 27, 2199–2202.

O-Methyl cyclohexanone oxime. Yield, 76%; colorless oil; $^1H$ NMR (300 MHz, $CDCl_3$) δ1.40–1.80 (m, 6H), 2.20 (t, J=6.0 Hz, 2H), 2.45 (t, J=6.1 Hz, 2H), 3.81 (s, 3H).

O-Methyl cyclododecanone oxime. Yield, 98%; colorless oil; $^1H$ NMR (500 MHz, $CDCl_3$) δ1.20–1.49 (m, 14H), 1.50–1.60 (m, 2H), 1.61–1.70 (m, 2H), 2.22 (t, J=6.8 Hz, 2H), 2.35 (t, J=6.6 Hz, 2H), 3.81 (s, 3H).

O-Methyl 3,3,5,5-tetramethylcyclohexanone oxime. Yield, 91%; colorless oil; $^1H$ NMR (500 MHz, $CDCl_3$) δ0.96 (s, 6H), 0.97 (s, 6H), 1.33 (s, 2H), 1.95 (s, 2H), 2.20 (s, 2H), 3.80 (s, 3H).

O-Methyl 4-phenylcyclohexanone oxime. Yield, 92%; colorless solid; mp 45–47° C.; $^1H$ NMR (500 MHz, $CDCl_3$) δ1.57–1.76 (m, 2H), 1.82–1.92 (m, 1H), 1.99–2.13 (m, 2H), 2.19–2.30 (m, 1H), 2.47–2.56 (m, 1H), 2.72–2.81 (m, 1H), 3.32–3.42 (m, 1H), 3.85 (s, 3H), 7.17–7.34 (m, 5H).

O-Methyl bicyclo[3.3.1]nonan-9-one oxime. Yield, 96%; colorless oil; $^1H$ NMR (500 MHz, $CDCl_3$) δ1.46–1.62 (m, 2H), 1.72–2.11 (m, 10H), 2.47 (br s, 1H), 3.40 (br s, 1H), 3.82 (s, 3H).

1-(p-Toluenesulfonyl)-4-piperidone. To a solution of 4-piperidone monohydrate hydrochloride (7.68 g, 50 mmol) in methylene chloride (50 ml) were added sequentially p-toluenesulfonyl chloride (10.50 g, 55.07 mmol) and triethylamine (21 ml). The mixture was stirred at room temperature for 16 h before being quenched with water (100 ml). The organic layer was washed with 1M HCl (100 ml) and brine (100 ml), and dried over sodium sulfate. Evaporation of the solvent gave the desired ketone (8.60 g, 68%) as a colorless solid. mp 130–132° C.; $^1H$ NMR (500 MHz, $CDCl_3$) δ2.40 (s, 3H), 2.58 (t, J=6.4 Hz, 4H), 3.38 (t, J=6.4 Hz, 4H), 7.35 (d, J=7.8 Hz, 2H), 7.68 (d, J=8.3 Hz, 2H).

1-[3-(Ethoxycarbonyl)propionyl]-4-piperidone. To a solution of 4-piperidone monohydrate hydrochloride (7.68 g, 50 mmol) and triethylamine (21 ml) in methylene chloride (100 ml) was added 3-(ethoxycarbonyl)propionyl chloride (9.87 g, 60 mmol) at 0° C. over a period of 10 min. The mixture was stirred at room temperature for 16 h before being quenched with water (100 ml). The organic layer was separated and the aqueous layer was extracted with methylene chloride (100 ml). The combined organic layers were washed with 1M HCl (100 ml), saturated aqueous sodium bicarbonate (100 ml), and brine (100 ml), dried over sodium sulfate, and concentrated. Purification by flash chromatography (silica gel, 30% ether in hexanes) gave the desired ketone (3.80 g, 33%) as a light yellow oil. $^1$H NMR (500 MHz, CDCl$_3$) δ1.27 (t, J=7.3 Hz, 3H), 2.48 (t, J=6.4 Hz, 2H), 2.53 (t, J=6.4 Hz, 2H), 2.68 (s, 4H), 3.82 (t, J=6.3 Hz, 2H), 3.82 (t, J=6.3 Hz, 2H), 4.16 (q, J=7.3 Hz, 2H).

1,1-Dioxotetrahydrothiopyran-4-one. To a solution of tetrahydrothiopyran-4-one (400 mg, 3.45 mmol) in acetonitrile (5 ml) was added aqueous Na$_2$EDTA (3 ml, 0.0004 M). A mixture of oxone (6.30 g, 10.30 mmol) and sodium bicarbonate (2.70, 32 mmol) was added in small portions to the above solution over a period of 20 min. The slurry was stirred for another 1 h before being quenched with methylene chloride. The organic solvent was decanted and the solid residue was triturated with ethyl acetate (3×25 ml). The combined organic layers were dried over sodium sulfate and concentrated to give the desired ketone (0.37 g, 73%) as a colorless solid. mp 170–172° C. (lit. 168–170° C.); $^1$H NMR (500 MHz, CDCl$_3$) 2.99 (t, J=6.8 Hz, 4H), 3.39 (t, J=6.8 Hz, 4H). Ref: Yang, D.; Yip, Y.-C.; Jiao, G.-S.; Wong, M.-K. Design of Efficient Ketone Catalysts for Epoxidation by Using the Field Effect. *J. Org. Chem,* 1998, 63, 8952–8956.

Synthesis of 1-benzenesulfonyl-4-piperidone (representative procedure). To a solution of 4-piperidone monohydrate hydrochloride (4.59 g, 30 mmol), triethylamine (12.5 ml, 90 mmol) in CH$_2$Cl$_2$ (50 ml) was added benzenesulfonyl chloride (5.30 g, 30 mmol). The mixture was stirred at 25° C. for 16 h. After evaporation of solvents, the residue was triturated with water (100 ml), filtered, and further purified by recrystallization from hexanes/CH$_2$Cl$_2$ (3:1) to afford the desired ketone (5.97 g, 83%) as a colorless solid. mp 116–118° C.; $^1$H NMR (500 MHz, CDCl$_3$) δ2.54 (t, J=6.4 Hz, 4H), 3.41(t, J=6.4 Hz, 4H). 7.58 (d, J=7.8 Hz, 2H), 7.63 (t, J=7.0 Hz, 1H), 7.81 (d, J=7.8 Hz, 2H).

1-(4-Methoxybenzenesulfonyl)-4-piperidone. Yield, 77%; colorless solid; mp 130–132° C.; $^1$H NMR (500 MHz, CDCl$_3$) δ2.56 (t, J=6.4 Hz, 4H), 3.38 (t, J=6.3 Hz, 4H), 3.95 (s, 3H), 7.00 (d, J=8.2 Hz, 2H), 7.75 (d, J=8.2 Hz, 2H).

1-(4-Chlorobenzenesulfonyl)-4-piperidone. Yield, 73%; colorless solid; mp 166–168° C.; $^1$H NMR (500 MHz, CDCl$_3$) δ2.55 (t, J=6.4 Hz, 4H), 3.41 (t, J=6.4 Hz, 4H), 7.54 (d, J=8.3 Hz, 2H), 7.81 (d, J=8.4 Hz, 2H).

1-Methanesulfonyl-4-piperidone. To a suspension of 4-piperidone monohydrate hydrochloride (2.0 g, 13 mmol) and K$_2$CO$_3$ (9.0 g, 65.2 mmol) in acetone (40 ml) was added methanesulfonyl chloride (5.96 g, 52.1 mmol) at 0–5° C. The mixture was stirred at 25° C. for 24 h. The solid material was removed by filtration, and the filtrate was concentrated to dryness. The residue was purified by flash chromatography (silica gel, 80% ether in hexanes) to afford the desired ketone (1.20 g, 52%) as a colorless solid. mp 102–104° C.; $^1$H NMR (500 MHz, CDCl$_3$) δ2.58 (t, J=6.4 Hz, 4H), 2.90 (s, 3H), 3.60 (t, J=6.4 Hz, 4H).

Ethoxycarbonylmethylene triphenylphosphorane. To a solution of triphenylphosphine (26.20 g, 100 mmol) in benzene (150 ml) was added ethyl bromoacetate (16.70 g, 100 mmol) at 0–5° C. The mixture was kept at room temperature for 16 h. The resulting phosphonium salt was filtered, washed with benzene (100 ml), and dried. To a solution of the solid in water (200 ml) was added benzene (200 ml), followed by 10% NaOH solution (100 ml). The organic layer was separated, and the aqueous layer was extracted with benzene (200 ml). The combined organic layers were washed with water (100 ml) and brine (100 ml), concentrated to 50 ml in vacuo, and poured onto hexane (200 ml). The precipitate was filtered and dried to afford the desired phosphorane (28.00 g, 80%) as a colorless solid. mp 128–130° C.

4-Oxocyclohexylideneacetic acid ethyl ester. To a solution of 1,4-cyclohexanedione (5.00 g, 44.64 mmol) in benzene (100 ml) was added the ylide (15.55 g, 44.68 mole). The mixture was heated under reflux for 12 h. After removal of the solvent by evaporation, the residue was purified by flash chromatography (silica gel, 5% ethyl acetate in hexanes) to afford the ketone ester (5.80 g, 71%) as a colorless oil. $^1$H NMR (500 MHz, CDCl$_3$) δ1.26 (t, J=6.4 Hz, 3H), 2.42–2.50 (m, 4H,), 2.60–2.66 (m, 2H), 3.12–3.20 (m, 2H), 4.16 (q, J=6.4 Hz, 2H), 5.86 (s, 1H).

4-Oxocyclohexaneacetic acid ethyl ester. To a solution of the unsaturated ester (2.50 g, 13.74 mmol) in ethanol (25 ml) was added Raney nickel (1.0 g). The mixture was stirred at room temperature under H$_2$ (balloon) for 24 h. After the catalyst was removed by filtration, the filtrate was concentrated to give the alcohol ester, which was used for the Jones' oxidation without further purification. To a solution of the above residue in acetone (20 ml) at 0° C. was added Jones' reagent (6 ml), prepared by dissolving CrO$_3$ (27.20 g) in concentrated sulfuric acid (25 ml) and further diluting the solution to 100 ml with water. The reaction was stirred at 0° C. for 2 h before being quenched with isopropanol (3 ml). The organic solvent was removed in vacuo and the residue was diluted with ether (100 ml) and washed with water (50 ml) and brine (50 ml). The organic layer was dried over MgSO$_4$ and concentrated to afford the ketone ester (1.80 g, 71%) as a colorless oil. $^1$H NMR (500 MHz, CDCl$_3$) δ 1.26 (t, J=6.4 Hz, 3H), 1.44–1.48 (m, 3H), 2.08–2.10 (m, 2H), 2.29–2.31 (d, J=8.3 Hz, 2H), 2.39–2.40 (m, 4H), 4.18 (q, J=6.4 Hz, 2H).

4-Oxocyclohexanecarboxylic acid. A mixture of ethyl 4-oxocyclohexanecarboxylate (1.74 g, 10 mmol), methanol (25 ml), and 17% aq. KOH (5 ml) was heated at 50° C. for 1.5 h. After being cooled to room temperature, the reaction mixture was acidified to pH 3 with conc. HCl, concentrated to 10 ml under reduced pressure, and extracted with chloroform (3×15 ml). The combined organic layers were dried over MgSO$_4$, filtered, and concentrated to afford the desired ketone acid (1.30 g, 91%) as a colorless solid. mp 62–64° C.; $^1$H NMR (500 MHz, CDCl$_3$) δ 2.05–2.10 (m, 2H), 2.23–2.27 (m, 2H), 2.35–2.41 (m, 2H), 2.49–2.54 (m, 2H), 2.80–2.84 (m, 1H).

Neopentyl 4-oxocyclohexanecarboxylate. To a solution of 4-oxocyclohexanecarboxylic acid (852 mg, 6 mmol), triphenylphosphine (1.59 g, 6 mmol), and neopentyl alcohol (635 mg, 7.2 mmol) in dry THF (18 ml) at 0° C. was added dropwise a solution of diethyl azodicarboxylate (0.96 ml, 6 mmol) in dry THF (7.5 ml). The reaction was stirred at rt overnight before being quenched by addition of saturated aqueous NaHCO$_3$ (50 ml). The aqueous phase was separated and extracted with CH$_2$Cl$_2$ (2×30 ml). The organic extracts were combined, dried over MgSO$_4$, and concentrated in vacuo. The residue was diluted with ether (10 ml) and petroleum ether (20 ml) and filtered to remove triphenylphosphine oxide. The solvent was removed in vacuo and the residue was purified by chromatography (20% ether in petroleum ether) to afford the desired ketone ester (820 mg, 65%) as a colorless oil. $^1$H NMR (500 MHz, CDCl$_3$) δ 0.96 (s, 9H), 2.04–2.07 (m, 2H), 2.22–2.25 (m, 2H), 2.34–2.40 (m, 2H), 2.46–2.50 (m, 2H), 2.80 (m, 1H), 3.82 (s, 2H).

4-Hydroxy-4-(4-fluorophenyl)cyclohexanone ethylene ketal. To a 500 ml round-bottom flask equipped with a mechanical stirrer, condenser and addition funnel were added magnesium turnings (3.50 g, 140 mmol) and enough THF to cover the Mg. A solution of 1-bromo-4-fluorobenzene (12.45 g, 70.43 mmol) in THF (90 ml) was added dropwise at such a rate that the reaction maintained a gentle reflux following reaction-initiation (the initiation may be accomplished by warming the flask). After the mixture was refluxed for an additional 2.5 h, a solution of 1,4-cylohexanedione monoethylene ketal (10.00 g, 64.03 mmol) in THF (75 ml) was added dropwise. The mixture was kept at refluxing for an additional 2 h before being quenched with saturated ammonium chloride solution (7 ml). After removal of the magnesium salts by filtration, the filtrate was concentrated to dryness. The residue was dissolved in $CHCl_3$ and washed with water and brine. The organic layer was separated, dried over $MgSO_4$, and concentrated. The residue was purified by flash chromatography (30% ether in petroleum ether) to afford the desired alcohol (13.50 g, 87%) as a colorless solid. mp 133–134° C. $^1H$ NMR (500 MHz, $CDCl_3$) δ 1.69 (d, J=11.7 Hz, 2H), 1.79 (d, J=12.2 Hz, 2H), 2.05–2.18 (m, 4H), 3.98 (m, 4H), 7.02 (t, J=8.3, 2H). 7.47–7.50 (m, 2H).

4-Hydroxy-4-(4-fluorophenyl)cyclohexanone. A mixture of 4-hydroxy-4-(4-fluorophenyl)cyclohexanone ethylene ketal (7.20 g, 28.6 mmol), THF (125 ml) and 5% aq. HCl (65 ml) was refluxed for 14 h. The reaction mixture was cooled to rt, concentrated to 60 ml, and extracted with $CH_2Cl_2$ (3×60 ml). The combined organic layers were dried over $MgSO_4$ and concentrated in vacuo. The residue was purified by crystallization from hexanes to afford the desired alcohol ketone (5.30 g, 89%) as a colorless solid. mp 111–114° C. (lit. 115–117° C.). $^1H$ NMR (500 MHz, $CDCl_3$) δ 2.17–2.20 (m, 2H), 2.23–2.29 (m, 2H), 2.32–2.37 (m, 2H), 2.87–2.94 (m, 2H), 7.04–7.07 (m, 2H), 7.48–7.51 (m, 2H).

4-Acetoxy-4-(4-fluorophenyl)cyclohexanone. To a solution of 4-hydroxy-4-(4-fluorophenyl)cyclohexanone (520 mg, 2.5 mmol), pyridine (2 ml) and 4-dimethylaminopyridine (46 mg) in $CH_2Cl_2$ (25 ml) at 0° C. was added dropwise a solution of acetic anhydride (1 ml) in $CH_2Cl_2$ (5 ml). The mixture was warmed to room temperature and stirred for 28 h before being quenched with water (30 ml). The organic phase was washed with 1M HCl (2×30 ml) and brine (30 ml), dried over $MgSO_4$, and concentrated in vacuo. The residue was purified by flash chromatography (25% ether in petroleum ether) to afford the desired ketone (510 mg, 82%) as a colorless solid. mp 113–115° C. $^1H$ NMR (500 MHz, $CDCl_3$) δ 2.11 (s, 3H), 2.20 (m, 2H), 2.43 (m, 2H), 2.68 (m, 2H), 2.86 (m, 2H), 7.05 (t, J=8.3, 2H), 7.35–7.38 (m, 2H).

General procedure for the preparation of 1,2,4-trioxolanes. Ozone was produced with an OREC ozone generator (0.6 L/min $O_2$, 60 V), passed through an empty gas washing bottle that was cooled to −78° C., and bubbled through a solution of an O-methyl ketone oxime and a ketone in pentane/$CH_2Cl_2$ at 0° C. O-methyl oximes of cyclohexanone, 2-adamantanone, and 3,3,5,5-tetramethylcyclohexanone (1 mmol) were consumed within 3 min while O-methyl cyclododecanone oxime (1 mmol) required 6 min to disappear. After completion, the solution was flushed with oxygen for 5 min before being concentrated in vacuo at room temperature to give a residue that was purified by flash chromatography.

EXAMPLE 2

Antimalarial Activity of OZ01-OZ369

Antimalarial Assays

Various OZ compounds were tested by the semiautomated microdilution assay against intraerythrocytic forms of *Plasmodium falciparum* derived from asynchronous stock cultures. The culture medium used was RPMI 1640 supplemented with 10% human type $A^+$ serum, 25 mM HEPES, 25 mM $NaHCO_3$ (pH 7.3). Human type $A^+$ erythrocytes served as host cells. The culture was kept at 37° C. in an atmosphere of 3% $O_2$, 4% $CO_2$, and 93% $N_2$ in humidified modular chambers.

Compounds were dissolved in DMSO (10 mg/ml), pre-diluted in complete culture medium, and titrated in duplicate in serial twofold dilutions over a 64-fold range in 96-well microtiter plates. After addition of the parasite cultures with an initial parasitemia (expressed as the percentage of erythrocytes infected) of 0.75% in a 2.5% erythrocytes suspension, the test plates were incubated under the conditions described above for 72 h. Growth of the parasites cultures was measured by the incorporation of radiolabelled [$^3H$]-hypoxanthine added 16 h prior to termination of the test. Fifty percent inhibitory concentration ($IC_{50}$) were estimated by Logit regression analysis. Compounds were tested against reference *P. falciparum* strains, K1 strain (Thailand resistant to chloroquine) and NF54 strain (an airport strain of unknown origin that is sensitive to standard antimalarials).

In the single dose STI in vivo screen, Moro SPF or NMRI mice infected with the ANKA strain of *P. berghei* (groups of 3–5 mice) were treated on day one post-infection with trioxolanes dissolved or suspended in 3% ethanol and 7% Tween 80. Trioxolanes were administered as single 10 mg/kg doses sc and po. Trioxolanes were also administered as single 3 mg/kg and 10 mg/kg doses in standard suspending vehicle (SSV). SSV consists of 0.5% w/v CMC, 0.5% v/v benzyl alcohol, 0.4% v/v Tween 80, and 0.9% w/v sodium chloride in water. Antimalarial activity was measured by percent reduction in parasitemia on day three post-infection and survival times compared to an untreated control group. Survival to day 30 post-infection is considered to be a cure. In U.S. Pat. No. 6,486,199, Table 1 presented data for trioxolanes OZ01-OZ90 along with the controls, fenozan, artemisinin, arteether, artemether, and artesunate. The data showed that antimalarial activity falls off both when the trioxolane peroxide bond is too exposed or is sterically inaccessible to iron(II) species. Other factors influencing antimalarial activity include the stability of carbon radicals formed by β-scission subsequent to the initial electron transfer to the peroxide bond and the influence of steric effects remote from the peroxide bond on the interactions between carbon radicals and potential drug targets. The data also demonstrated that trioxolane carboxylic acids are usually less active than their hydrocarbon, ester, and hydroxamic acid counterparts.

Below is the activity data for OZ91-OZ369.

TABLE 1

| Compd | $IC_{50}$ (ng/ml) K1/NF54 | Activity (%) po/SSVpo/sc | Survival (days) po/SSVpo/sc |
|---|---|---|---|
| NONE | — | 0 | 5.6 ± 0.3 |
| OZ01 | >100/>100 | 0/NA/0[1] | 5.3/NA/5.3[1] |
| OZ02 | >100/94 | 0/NA/0[1] | 5.0/NA/5.0[1] |
| OZ03 | 1.2/1.6 | 94/NA/100 | 7.2/NA/11.9 |
| OZ04 | >100/>100 | 0/NA/0[1] | 5.3/NA/5.3[1] |
| OZ05 | 0.19/0.36 | 94/74/99.7 | 7.1/6.2/8.6 |

TABLE 1-continued

| | | | |
|---|---|---|---|
| OZ06 | 18/22 | T/NA/T[1] | 1.0/NA/1.0[1] |
| OZ07 | 66/49 | 0/NA/0[1] | 6.0/NA/5.7[1] |
| OZ08 | 2.4/2.8 | 99.7/NA/99.9[1] | 8.0/NA/9.7[1] |
| OZ09 | 32/39 | 0/NA/81[1] | 5.0/NA/6.3[1] |
| OZ10 | 0.40/0.67 | 99.6/NA/99.98 | 8.9/NA/10.5 |
| OZ11 | 1.5/2.7 | 99.99/98/100 | 11.4/7.4/18 |
| OZ12 | 0.60/0.77 | 75/NA/99.8 | 7.0/NA/9.3 |
| OZ13 | 0.40/0.50 | 56/NA/99.7 | 6.7/NA/9.7 |
| OZ14 | 91/>100 | 23/NA/96 | 6.0/NA/7.7 |
| OZ15 | 0.60/1.0 | 99.8/88/99.9 | 7.4/6.8/8.2 |
| OZ16 | 0.45/0.67 | 79/83/99.2 | 6.7/6.7/7.3 |
| OZ17 | 85/>100 | 0/NA/18 | 5.3/NA/6.3 |
| OZ18 | 63/84 | 0/NA/0 | 5.0/NA/5.3 |
| OZ19 | 1.3/2.7 | 98.3/56/99.98 | 7.5/6.0/13.4 |
| OZ20 | 15/20 | 97/14/90 | 7.4/6.0/7.0 |
| OZ21 | 14/25 | 0/NA/0 | 5.0/NA/6.0 |
| OZ22 | 0.32/0.56 | 35/NA/99.6 | 6.0/NA/7.7 |
| OZ23 | 0.29/0.57 | 99.5/99.34/99.9 | 7.7/7.0/8.9 |
| OZ24 | 0.35/0.58 | 93/66/99.9 | 7.0/6.8/8.7 |
| OZ25 | 1.1/2.1 | 99.9/96/99.97 | 8.4/7.2/16.5 |
| OZ26 | 3.1/5.0 | 88/NA/99.9 | 7.0/NA/9.7 |
| OZ27 | 2.2/4.8 | 99.97/96/99.92 | 12.6/8.0/17.1 |
| OZ28 | 2.1/2.5 | 93/NA/99.97 | 7.3/NA/12.3 |
| OZ29 | 9.7/13 | 0/NA/0 | 5.0/NA/5.0 |
| OZ30 | 0.65/1.3 | 0/NA/86 | 5.3/NA/9.0 |
| OZ31 | 3.0/3.0 | 99.95/90/99.95 | 9.0/7.3/17.7 |
| OZ32 | 0.25/0.51 | 79/93/91 | 6.7/7.0/8.7 |
| OZ33 | 2.3/3.5 | 80/NA/99.97 | 6.7/NA/11.7 |
| OZ34 | 42/60 | 0/NA/0 | 5.3/NA/5.7 |
| OZ35 | 1.7/2.1 | 74/NA/99.98 | 6.3/NA/9.3 |
| OZ36 | 24/62 | 0/NA/0 | 5.7/NA/5.7 |
| OZ37 | 1.1/1.6 | 83/NA/99.98 | 6.7/NA/13 |
| OZ38 | 0.86/1.3 | 83/15/99.98 | 6.7/5.0/25.3 |
| OZ39 | 1.4/1.8 | 61/NA/99.3 | 6.3/NA/7.7 |
| OZ40 | 1.4/2.0 | 99/NA/99.8 | 7.3/NA/9.0 |
| OZ41 | 3.5/4.6 | 99.98/81/99.5 | 12.1/6.8/10.7 |
| OZ42 | 2.3/2.6 | 68/NA/92 | 6.0/NA/7.0 |
| OZ43 | 11/7.5 | 99.97/18/97 | 8.9/5.4/7.3 |
| OZ44 | 2.5/2.3 | 99.3/NA/99.9 | 7.0/NA/8.3 |
| OZ45 | 17/27 | 15/NA/16 | 6.0/NA/5.0 |
| OZ46 | 22/19 | 99/NA/62 | 7.7/NA/6.0 |
| OZ47 | 7.5/7.4 | 99.98/NA/99 | 12.7/NA/8.0 |
| OZ48 | 11/13 | 99.8/NA/42 | 8.7/NA/6.3 |
| OZ49 | 0.82/0.93 | 81/NA/85 | 6.7/NA/7.3 |
| OZ50 | 1.1/1.2 | 77/57/97 | 7.0/5.7/7.3 |
| OZ51 | 2.5/2.5 | 89/NA/100 | 7.0/NA/14 |
| OZ52 | 3.1/3.0 | 88/NA/99.7 | 6.7/NA/8.0 |
| OZ53 | 1.4/1.7 | 9/NA/58 | 6.0/NA/6.3 |
| OZ54 | 32/35 | 85/NA/97 | 7.0/NA/7.0 |
| OZ55 | 0.49/0.60 | 45/NA/97 | 6.0/NA/7.3 |
| OZ56 | 0.59/0.64 | 93/63/99.97 | 6.7/5.7/10.3 |
| OZ57 | 3.1/2.8 | 32/NA/98.4 | 6.0/NA/7.7 |
| OZ58 | 7.1/7.2 | 39/NA/52 | 6.0/NA/6.3 |
| OZ59 | 1.4/1.3 | 51/NA/99.95 | 6.0/NA/10.0 |
| OZ60 | 1.1/1.2 | 71/NA/100 | 6.0/NA/10.3 |
| OZ61 | 0.52/0.53 | 91/NA/96 | 7.0/NA/7.3 |
| OZ62 | 33/28 | 0/NA/0 | 6.0/NA/5.0 |
| OZ63 | 1.6/1.6 | 99.62/65/99.91 | 7.3/6.0/9.3 |
| OZ64 | 1.5/1.3 | 95/NA/98 | 7.3/NA/8.0 |
| OZ65 | 57/65 | 0/NA/1 | 5.0/NA/5.0 |
| OZ66 | 44/36 | 0/NA/0 | 5.3/NA/5.7 |
| OZ67 | >100/>100 | 0/NA/0 | 5.0/NA/5.0 |
| OZ68 | 41/49 | 1/NA/6 | 5.0/NA/5.3 |
| OZ69 | 1.6/1.4 | 56/NA/40 | 6.3/NA/6.3 |
| OZ70 | 1.2/1.1 | 98/NA/94 | 7.7/NA/7.7 |
| OZ71 | 4.5/3.7 | 98/98/97 | 7.3/6.7/8.3 |
| OZ72 | 15/13 | 97/NA/95 | 7.7/NA/6.7 |
| OZ73 | 6.5/8.2 | 27/NA/36 | 6.0/NA/6.7 |
| OZ74 | 2.3/3.5 | 63/NA/99.97 | 6.3/NA/10.0 |
| OZ75 | 2.4/4.3 | 77/NA/5 | 7.3/NA/6.0 |
| OZ76 | 1.7/3.0 | 49/NA/94 | 6.3/NA/8.0 |
| OZ77 | 1.4/2.2 | 99.9/74/98 | 9.0/6.0/8.3 |
| OZ78 | 24/42 | 94/97/79 | 8.7/7.0/6.7 |
| OZ79 | 0.38/0.81 | 85/99.94 | 7.0/NA/9.3 |
| OZ80 | 0.15/0.34 | 59/NA/84 | 6.3NA/7.7 |
| OZ81 | >100/>100 | 0/NA/0 | 5.3/NA/5.0 |
| OZ82 | 0.48/1.2 | 91/NA/79 | 7.3/NA/7.0 |
| OZ83 | 0.30/0.60 | 92/78/99.8 | 7.0/6.3/8.0 |
| OZ84 | 1.4/2.1 | 92/NA/99.99 | 7.7/NA/14.7 |
| OZ85 | 0.86/1.8 | 34/NA/99.7 | 6.0/NA/8.3 |
| OZ86 | 0.80/2.0 | 77/NA//99.9 | 6.7/NA/11.3 |
| OZ87 | 3.6/4.4 | 22/NA/53 | 5.7/NA/6.0 |
| OZ88 | 5.7/4.2 | 62/NA/99.1 | 6.0/NA/11.7 |
| OZ89 | 0.30/0.75 | 94/89/99.8 | 7.3/6.7/8.7 |
| OZ90 | 0.44/0.84 | 89/95/99 | 7.0/7.0/8.0 |
| OZ91 | 1.4/0.42 | 20/0/85 | 5.7/6.0/7.3 |
| OZ92 | 1.6/0.40 | 81/35/99.98 | 6.7/6.3/10.0 |
| OZ93 | 3.3/0.92 | 57/3/100 | 6.7/6.0/13.3 |
| OZ94 | 57/28 | 21/0/11 | 6.0/5.7/5.3 |
| OZ95 | 2.8/1.3 | 31/0/49 | 6.0/6.0/6.0 |
| OZ96 | 8.4/>10 | 12/14/19 | 5.7/5.7/5.3 |
| OZ97 | 2.2/1.8 | 59/2/66 | 6.7/5.3/7.0 |
| OZ98 | 2.3/0.9 | 72/11/77 | 6.3/5.3/7.3 |
| OZ99 | 77/27 | 30/40/36 | 6.3/5.7/6.3 |
| OZ100 | 1.4/0.34 | 61/36/80 | 6.7/6.3/7.0 |
| OZ101 | 3.0/1.6 | 44/0/99.97 | 6.3/5.3/13 |
| OZ102 | 1.6/0.45 | 92/73/99.97 | 7.0/6.7/19.7 |
| OZ103 | 0.64/0.17 | 86/63/87 | 7.3/6.7/7.3 |
| OZ104 | 1.4/0.50 | 56/0/99.98 | 6.3/5.7/12.0 |
| OZ105 | 5.4/5.0 | 16/0/28 | 5.7/5.7/6.3 |
| OZ106 | 2.2/1.7 | 0/0/0 | 5.3/5.05.3 |
| OZ107 | 1.0/0.30 | 70/32/99.74 | 6.3/6.3/8.0 |
| OZ108 | 68/29 | 0/0/0 | 5.0/5.0/5.7 |
| OZ109 | 21/24 | 2/0/24 | 5.7/5.7/6.3 |
| OZ110 | 5.3/2.1 | 50/0/97.97 | 6.7/5.3/7.7 |
| OZ111 | 0.92/0.35 | 98/79/99.94 | 7.7/6.3/8.3 |
| OZ112 | >10/>10 | 6/0/36 | 5.7/5.7/6.3 |
| OZ113 | 0.95/0.20 | 92/96/89 | 7.3/8.0/7.3 |
| OZ114 | 3.7/2.2 | 0/0/99.64 | 5.7/6.0/8.7 |
| OZ115 | 11/6.9 | 33/0/97 | 6.3/5.7/7.3 |
| OZ116 | 4.2/3.3 | 97/96/96 | 7.7/8.3/8.0 |
| OZ117 | 2.1/1.2 | 95/96/99.94 | 7.0/7.7/8.7 |
| OZ118 | 1.0/0.24 | 99.0/98/99.57 | 7.0/8.0/8.3 |
| OZ119 | 0.83/0.20 | 99.29/99.15/99.66 | 7.7/8.0/8.3 |
| OZ120 | 1.2/0.59 | 33/8/96 | 6.0/5.7/8.0 |
| OZ121 | 0.96/0.41 | 91/98/99.61 | 7.3/8.0/7.3 |
| OZ122 | >100/>100 | 10/3/0 | 5.7/5.3/5.0 |
| OZ123 | 1.6/1.9 | 99.66/94/99.96 | 8.0/7.0/16 |
| OZ124 | 2.1/1.7 | 72/17/86 | 6.3/5.3/7.0 |
| OZ125 | 68/>100 | 8/0/0 | 5.3/5.7/6.0 |
| OZ126 | 0.20/0.50 | 55/72/99.44 | 7.0/6.7/8.5 |
| OZ127 | 0.61/1.3 | 95/98/97 | 7.0/7.7/7.7 |
| OZ128 | 0.59/1.1 | 99.93/99.95/99.98 | 8.3/8.7/11.7 |
| OZ129 | 10/>10 | 0/4/0 | 5.3/5.7/5.7 |
| OZ130 | 0.62/0.94 | 98.8/98.9/98.6 | 9.0/8.0/7.3 |
| OZ131 | 1.7/4.1 | 21/41/90 | 5.7/6.0/8.0 |
| OZ132 | 9.8/>10 | 38/0/40 | 6.3/6.3/6.3 |
| OZ133 | 0.70/1.1 | 94/97/72 | 7.0/7.3/7.0 |
| OZ134 | 0.88/1.1 | 72/27/99.95 | 6.3/6.0/15.3 |
| OZ135 | >100/>100 | 1/0/0 | 5.3/5.3/5.3 |
| OZ136 | 23/21 | 0/0/0 | 6.0/6.0/6.0 |
| OZ137 | 11/18 | 0/6/61 | 5.7/6.3/7.0 |
| OZ138 | 10/19 | 0/5/7 | 5.7/6.3/6.3 |
| OZ140 | 5.9/8.2 | 0/8/60 | 6.0/6.3/7.0 |
| OZ141 | 1.7/1.9 | 98/97/99.89 | 8.0/8.0/8.7 |
| OZ142 | 2.3/2.3 | 0/2/99.98 | 6.0/6.3/14.3 |
| OZ143 | 0.98/1.8 | 48/44/99.85 | 6.7/6.7/9.7 |
| OZ144 | 1.4/2.1 | 99.45/92/99.94 | 7.3/7.3/16.7 |
| OZ145 | 0.50/0.76 | 99.82/99.21/99.87 | 8.3/10.7/10.7 |
| OZ146 | 2.2/2.7 | 62/40/91 | 7.0/6.3/9.0 |
| OZ147 | 1.1/1.8 | 85/71/99.89 | 8.0/8.0/19.7 |
| OZ148 | 17/16 | 38/58/21 | 7.3/7.7/6.3 |
| OZ149 | 8.0/8.8 | 64/3/87 | 7.7/6.0/14.3 |
| OZ151 | 3.8/4.0 | 71/71/99.63 | 7.3/7.3/11.0 |
| OZ152 | 3.2/7.2 | 0/12/22 | 6.3/6.3/6.7 |
| OZ153 | 7.7/19 | 15/23/20 | 6.3/7.0/6.3 |
| OZ154 | 5.0/6.1 | 99.74/81/59 | 14.7/8.7/7.7 |
| OZ155 | 12/>10 | 53/53/73 | 6.3/7.0/8.3 |
| OZ156 | 2.1/2.1 | 99.98/98.8/99.98 | 17.0/10.3/19.7 |
| OZ157 | 0.20/0.22 | 90/80/97 | 7.3/8.3/8.3 |
| OZ159 | 0.70/0.94 | 34/31/98 | 6.7/7.3/9.0 |
| OZ160 | 0.70/0.87 | 45/43/99.94 | 6.3/6.7/12.0 |
| OZ161 | 0.40/0.50 | 59/46/99.96 | 7.0/7.0/12.7 |
| OZ162 | 0.50/0.71 | 41/22/99.55 | 6.3/6.3/9.3 |
| OZ163 | 0.2/0.2 | 99.90/99.94/100 | 8.0/9.0/9.7 |
| OZ164 | 59/>10 | 11/0/7 | 5.7/5.7/6.3 |
| OZ165 | 39/>10 | 18/3/9 | 6.3/6.0/5.7 |
| OZ166 | 28/>10 | 11/0/4 | 6.7/6.3/5.7 |

TABLE 1-continued

| Compd | IC$_{50}$ (ng/ml) K1/NF54 | Activity (%) 10/3 mg/kg SSV po | Survival (days) 10/3 mg/kg SSV po |
|---|---|---|---|
| OZ167 | 6.7/>10 | 0/6/97 | 6.0/6.0/7.3 |
| OZ169 | 15/>10 | 98/22/99.76 | 7.7/6.7/9.0 |
| OZ171 | 1.3/1.4 | 98/85/99.94 | 9.0/7.0/9.7 |
| OZ172 | 3.5/5.0 | 68/82/100 | 8.0/0/10.3/10.3 |
| OZ173 | 58/32 | 15/0/80 | 7.0/6.7/9.7 |
| OZ174 | 27/34 | 0/15/90 | 6.7/7.3/10.3 |
| OZ175 | 1.4/2.0 | 99.1/97/92 | 10.0/12.3/8.7 |
| OZ176 | 25/35 | 11/18/24 | 7.0/7.7/7.0 |
| OZ177 | 0.9/1.7 | 99.91/99.88/99.91 | 12.3/12.7/17.7 |
| OZ178 | 21/27 | 32/23/31 | 7.3/7.3/10.0 |
| OZ179 | 1.3/1.1 | 99.91/99.78/99.91 | 11.3/10.3/11.3 |
| OZ180 | 3.7/2.8 | 99.91/97/65 | 13.7/12.7/10.3 |
| OZ181 | 0.58/0.35 | 99.98/99.91/100 | 9.0/10.0/11.0 |
| OZ182 | 4.5/5.5 | 91/96/95 | 8.0/7.3/7.7 |
| OZ183 | 0.80/2.1 | 65/19/81 | 6.0/6.0/8.3 |
| OZ184 | 1.0/1.4 | 54/59/97 | 6.7/7.0/8.7 |
| OZ185 | 1.1/1.4 | 86/56/99.96 | 7.7/6.7/10.7 |
| OZ186 | >10/>10 | 87/96/67 | 8.0/9.0/8.0 |
| OZ187 | 4.0/6.8 | 77/94/77 | 7.7/10.0/7.0 |
| OZ188 | 1.5/3.0 | 93/98/99.87 | 8.7/10.0/9.0 |
| OZ189 | 1.7/3.0 | 95/99.79/98 | 9.3/9.0/10.7 |
| OZ190 | 0.16/1.0 | 98/78/2 | 8.7/7.7/5.7 |
| OZ191 | 6.0/>10 | 7/5/17 | 5.7/5.7/6.0 |
| OZ192 | 2.5/4.4 | 38/45/99.98 | 6.0/7.0/13.7 |
| OZ193 | 5.5/8.3 | 99.75/93/99.92 | 9.3/8.0/11.0 |
| OZ194 | 2.0/6.6 | 87/73/99.95 | 8.3/8.0/20.3 |
| OZ195 | 2.2/3.7 | 98/99.02/99.75 | 9.3/10.7/9.0 |
| OZ196 | >10/>10 | 10/0/17 | 6.0/5.3/5.7 |
| OZ197 | 1.0/2.0 | 87/90/99.54 | 7.7/8.7/10.3 |
| OZ198 | >10/>10 | 4/6/6 | 5.7/6.0/5.7 |
| OZ199 | 0.69/1.1 | 99.48/76/99.44 | 8.3/7.7/8.7 |
| OZ200 | 1.0/2.9 | 81/78/92 | 7.0/7.3/8.0 |
| OZ201 | 2.0/3.1 | 100/100/100 | 13/10.3/25 |
| OZ202 | 6.0/7.9 | 79/51/74 | 7.0/7.3/7.3 |
| OZ203 | 3.9/6.7 | 87/99.42/99.72 | 7.3/8.7/9.7 |
| OZ204 | >10/>10 | 0/0/0 | 6.0/6.3/6.0 |
| OZ205 | 1.5/2.0 | 99.96/99.94/99.96 | 10.0/8.7/9.7 |
| OZ206 | 1.0/2.7 | 93/92/91 | 8.0/8.7/9.7 |
| OZ207 | 0.33/0.57 | 99.96/99.98/99.98 | 9.3/12.0/11.3 |
| OZ208 | 6.0/6.5 | 0/29/10 | 6.3/6.7/5.7 |
| OZ209 | 0.21/0.32 | 99.94/99.96/99.97 | 9.5/10.0/12.5 |
| OZ210 | 1.4/1.6 | 99.23/77/99.94 | 9.3/8.0/10.3 |
| OZ211 | 1.0/1.2 | 82/78/99.90 | 8.0/7.3/8.7 |
| OZ212 | 2.7/2.9 | 66/25/59 | 6.7/6.7/8.0 |
| OZ213 | 2.3/2.8 | 83/74/85 | 8.0/8.0/8.0 |
| OZ214 | >10/>10 | 44/54/65 | 6.3/7.3/7.7 |
| OZ215 | 6.4/7.3 | 96/25/39 | 9.76/3/7.0 |
| OZ216 | 0.40/0.67 | 62/69/99.02 | 6.3/7.7/11.0 |
| OZ217 | 2.0/2.0 | 67/8/98 | 7.0/6.0/8.0 |
| OZ218 | 2.0/3.0 | 98/99.30/99.68 | 10.0/14.3/9.0 |
| OZ219 | 0.85/1.6 | 99.89/99.82/99.91 | 8.7/8.0/9.3 |
| OZ220 | 6.9/4.9 | 40/0/99.95 | 6.0/5.3/10.0 |
| OZ221 | >10/>10 | 80/87/97 | 6.3/7.0/8.0 |
| OZ222 | 3.9/6.3 | 87/75/99.76 | 7.7/7.0/10.0 |
| OZ223 | 4.0/>10 | 89/79/99.57 | 7.3/6.3/12.0 |
| OZ224 | 2.0/3.0 | 0/5/20 | 6.0/5.7/5.7 |
| OZ225 | 7.3/>10 | 0/0/17 | 5.7/5.7/6.3 |
| OZ226 | 4.0/4.0 | 0/0/99.92 | 5.0/5.3/11.0 |
| OZ227 | 0.20/0.20 | 99.68/99.90/99.84 | 8.3/9.3/10.7 |
| OZ228 | 2.0/2.1 | 99.94/28/99.94 | 10.3/6.0/14.0 |
| OZ229 | 0.24/0.23 | 99.96/99.08/99.98 | 10.0/8.3/12.7 |
| OZ230 | 3.9/3.6 | 0/0/0 | 5.3/5.7/5.7 |
| OZ231 | >10/>10 | 0/0/0 | 5.3/5.7/6.0 |
| OZ232 | 0.30/0.50 | 76/74/99.94 | 8.0/7.3/8.7 |
| OZ233 | 1.7/1.9 | 69/76/99.66 | 7.0/7.7/8.3 |
| OZ234 | 3.0/3.6 | 12/0/0 | 6.0/6.0/6.3 |
| OZ235 | 1.0/2.0 | 99.92/99.97/97 | 8.7/9.0/8.0 |
| OZ236 | 2.0/2.0 | 89/86/98.61 | 6.3/7.7/7.7 |
| OZ237 | 5.7/7.1 | 5/9/52 | 6.0/6.0/6.7 |
| OZ243 | 0.91/1.1 | 87/97/70 | 7.3/8.7/6.3 |
| OZ244 | 4.0/4.2 | 6/0/18 | 5.7/5.3/6.3 |
| OZ247 | 1.8/2.3 | 57/27/99.85 | 6.3/6.0/9.0 |
| OZ251 | 0.60/0.35 | 29/6/99.87 | 6.7/6.0/9.0 |
| OZ252 | 2.3/2.2 | 98.91/99.49/99.82 | 8.3/9.0/9.3 |
| OZ253 | 0.56/0.45 | 75/59/99.82 | 7.0/6.7/9.3 |
| OZ254 | >100/57 | 27/11/2 | 6.0/5.7/5.7 |
| OZ255 | 2.2/1.1 | 99.61/99.54/99.92 | 9.0/8.7/10.0 |
| OZ256 | 0.3/0.2 | 99.70/99.67/99.95 | 8.7/8.7/9.7 |
| OZ257 | 42/21 | 99.00/99.49/99.84 | 8.3/7.7/9.7 |
| OZ258 | 5.8/5.2 | 75/70/99.95 | 6.0/6.0/10.7 |
| OZ260 | 5.6/4.3 | 72/51/81 | 6.7/7.0/7.7 |
| OZ261 | 39/18 | 61/47/92 | 7.0/7.0/8.0 |
| OZ262 | 0.63/0.84 | 96/98/99.39 | 11.7/12.3/10.0 |
| OZ263 | 0.84/1.1 | 99.53/99.45/99.92 | 13.0/13.3/11.0 |
| OZ264 | 1.2/1.5 | 99.61/99.92/99.97 | 11.0/10.3/13.7 |
| OZ265 | 0.56/1.6 | 99/98/99.67 | 13.0/9.7/11.7 |
| OZ266 | 1.1/1.5 | 99/99.39/99.75 | 13.7/11.7/11.7 |
| OZ267 | 0.20/0.34 | 99.92/99.89/99.97 | 8.3/8.7/9.3 |
| OZ268 | 0.44/0.71 | 99.86/99.47/99.92 | 9.3/13.3/9.7 |
| OZ269 | 0.32/0.61 | 98/86/99.92 | 10.7/11.3/9.0 |
| OZ270 | 0.85/1.3 | 99.17/99.47/99.81 | 13.7/12.3/11.3 |
| OZ271 | 0.36/0.29 | 99.93/99.52 | 8.7/8.6 |
| OZ272 | 1.1/1.3 | 98/49 | 10.3/6.6 |
| OZ273 | 0.97/1.0 | 99.58/64 | 11.7/7.2 |
| OZ274 | 5.1/5.7 | 11/ND | 7.0/ND |
| OZ275 | 0.66/0.74 | 68/ND | 7.3/ND |
| OZ276 | 0.86/0.94 | 17/ND | 7.3/ND |
| OZ277 | 0.57/0.58 | 99.98/99.28 | 9.3/9.6 |
| OZ278 | 23/39 | 56/ND | 7.3/ND |
| OZ279 | 0.21/0.24 | 99.98/99.42 | 9.3/8.4 |
| OZ280 | 1.2/1.4 | 0/ND | 5.7ND |
| OZ281 | 0.50/0.30 | 99.87/96 | 8.7/10.2 |
| OZ282 | 2.0/2.4 | 98.5/53 | 8.3/7.2 |
| OZ283 | 1.7/2.0 | 99.81/56 | 8.3/8.2 |
| OZ284 | 1.0/1.4 | 97/61 | 9.0/7.8 |
| OZ285 | 1.3/1.8 | 99.81/72 | 8.7/7.6 |
| OZ286 | 0.94/1.6 | 99.73/60 | 8.7/7.0 |
| OZ287 | 0.49/0.83 | 95/68 | 8.3/7.2 |
| OZ288 | 1.7/2.7 | 99.96/82 | 11.0/8.0 |
| OZ289 | 0.40/0.56 | 99.94/92 | 13.4/7.4 |
| OZ290 | 0.42/0.45 | 99.64/95 | 9.0/7.0 |
| OZ291 | 0.52/0.72 | 98/34 | 8.0/6.8 |
| OZ292 | 0.19/0.26 | 74/46 | 7.0/6.6 |
| OZ293 | 0.25/0.34 | 99.58/77 | 8.8/7.4 |
| OZ294 | 0.39/0.63 | 99.79/70 | 8.6/7.4 |
| OZ295 | 0.44/0.75 | 47/35 | 7.0/6.4 |
| OZ296 | 0.60/0.89 | 99.22/90 | 10.0/9.2 |
| OZ297 | 0.49/0.76 | 99.69/83 | 9.8/7.6 |
| OZ298 | 2.0/3.0 | 99.95/98 | 9.4/9.0 |
| OZ299 | 6.8/6.3 | 36/0 | 6.6/6.4 |
| OZ300 | 71/97 | 6/0 | 6.8/7.0 |
| OZ301 | 2.1/2.8 | 100/97 | 11.8/8.4 |
| OZ302 | 1.9/2.9 | 99.60/88 | 9.0/9.0 |
| OZ303 | 1.6/2.4 | 99.01/69 | 8.6/7.6 |
| OZ304 | 1.6/2.3 | 98/61 | 8.2/8.8 |
| OZ305 | 1.8/1.9 | 99.93/96 | 9.2/9.6 |
| OZ306 | 3.9/3.6 | 99.58/87 | 9.2/8.2 |
| OZ307 | 0.62/0.88 | 98/74 | 9.4/7.8 |
| OZ308 | 1.2/1.7 | 86/30 | 7.8/6.6 |
| OZ309 | 11/17 | 99.80/86 | 8.8/7.8 |
| OZ310 | 0.82/1.1 | 81/38 | 7.8/8.2 |
| OZ311 | 1.2/1.8 | 80/40 | 8.6/7.0 |
| OZ312 | 19/27 | 43/13 | 7.2/6.2 |
| OZ313 | 0.55/0.76 | 98.9/58 | 10.4/7.4 |
| OZ314 | 11/17 | 13/11 | 6.6/6.6 |
| OZ315 | 2.8/3.0 | 99.97/92 | 11.2/9.6 |
| OZ316 | 1.0/1.7 | 69/7 | 10.0/8.0 |
| OZ317 | 0.33/0.36 | 99.92/99.20 | 9.8/10.0 |
| OZ318 | 0.56/0.82 | 88/29 | 12.4/7.6 |
| OZ319 | 0.41/0.91 | 99.92/99.14 | 10.6/10.8 |
| OZ320 | 0.68/1.30 | 99.76/92 | 10.4/11.8 |
| OZ321 | 0.58/0.97 | 99.77/64 | 14.0/9.8 |
| OZ322 | 0.90/1.5 | 98/61 | 10.0/9.4 |
| OZ323 | 0.85/1.1 | 99.98/99.92 | 15.6/9.2 |
| OZ324 | 2.4/3.4 | 60/26 | 9.4/7.4 |
| OZ325 | 0.62/1.4 | 99.43/30 | 8.8/6.2 |
| OZ326 | 0.65/1.2 | 80/7 | 7.4/6.0 |
| OZ327 | 0.85/1.1 | 97/72 | 9.8/7.0 |
| OZ328 | 1.4/3.0 | 99.77/75 | 8.6/7.6 |
| OZ329 | 0.43/0.68 | 99.97/99.50 | 11.2/9.2 |
| OZ330 | 0.55/1.2 | 99.96/82 | 12.2/7.2 |
| OZ331 | 0.50/1.2 | 99.47/66 | 9.0/7.0 |
| OZ332 | 1.7/2.5 | 8/0 | 6.0/6.0 |

TABLE 1-continued

| | | | |
|---|---|---|---|
| OZ333 | 0.24/0.44 | 99.86/96 | 9.2/8.0 |
| OZ334 | 28/20 | 47/13 | 6.8/6.6 |
| OZ335 | 0.29/0.28 | 99.95/97 | 9.2/10.0 |
| OZ336 | 1.4/0.91 | 99.93/98 | 9.2/9.6 |
| OZ337 | 0.29/0.25 | 99.92/97 | 8.6/11.6 |
| OZ338 | 0.38/0.45 | 99.93/99.80 | 9.8/8.0 |
| OZ339 | 0.35/0.39 | 99.95/99.65 | 10.2/9.2 |
| OZ340 | 4.9/2.9 | 93/36 | 9.2/6.4 |
| OZ341 | 2.4/2.0 | 97/32 | 8.0/7.0 |
| OZ342 | 1.8/1.2 | 27/0 | 6.8/6.4 |
| OZ343 | 0.46/0.49 | 99.94/99.21 | 9.4/10.0 |
| OZ344 | 1.2/2.1 | 17/0 | 7.8/7.4 |
| OZ345 | 1.9/2.4 | 75/0 | 9.2/6.6 |
| OZ346 | 3.8/4.7 | 85/51 | 8.8/7.6 |
| OZ347 | 11/11 | 2/0 | 6.6/7.6 |
| OZ348 | 3.2/3.5 | 97/24 | 9.2/6.6 |
| OZ349 | 0.70/1.3 | 99.92/99.88 | 11.2/9.6 |
| OZ350 | 1.1/2.2 | 99.17/69 | 10.4/9.6 |
| OZ351 | 0.40/0.54 | 99.90/99.69 | 9.4/9.0 |
| OZ352 | 19/20 | 99.66/77 | 8.2/7.2 |
| OZ353 | 0.35/0.56 | 99.96/99.91 | 9.2/9.6 |
| OZ354 | 0.55/0.82 | 99.97/99.63 | 9.6/10.0 |
| OZ355 | 0.29/0.42 | 71/0 | 7.0/6.2 |
| OZ356 | 1.4/1.1 | 99.64/87 | 8.6/8.0 |
| OZ357 | 0.56/0.79 | 99.99/99.81 | 10.2/8.8 |
| OZ358 | 0.22/0.36 | 99.96/99.02 | 10.4/9.6 |
| OZ359 | 0.40/0.52 | 99.94/96 | 9.4/8.8 |
| OZ360 | 58/59 | 38/0 | 6.8/6.2 |
| OZ361 | 3.5/2.3 | 99.90/85 | 8.4/7.8 |
| OZ362 | 0.81/0.31 | 98/58 | 9.8/7.0 |
| OZ363 | 46/55 | 40/10 | 6.8/6.0 |
| OZ364 | 8.4/6.2 | 63/80 | 7.0/7.3 |
| OZ365 | 0.79/0.25 | 99.57/92 | 8.0/8.0 |
| OZ366 | 1.4/0.74 | 84/62 | 8.2/7.0 |
| OZ367 | 0.66/0.25 | 96/59 | 8.6/6.8 |
| OZ368 | 0.63/0.43 | 99.94/99 | 9.0/9.2 |
| OZ369 | 0.69/0.54 | 99.90/0 | 8.4/5.8 |
| AM | 0.45/0.36 | 99.75/79 | 9.4/8.7 |
| AS | 1.4/1.5 | 87/66 | 7.0/8.0 |
| CQ | 76/4.4 | 99.92/82 | 9.0/8.0 |
| MFQ | 2.2/5.0 | 99.11/9 | 17/6.3 |

For comparative analysis, data is also presented for the control antimalarial drugs artemether (AM), artesunate (AS), chloroquine (CQ), and mefloquine (MFQ).

Antimalarial activity falls off when the trioxolane peroxide bond is too exposed or is sterically inaccessible to iron(II) species. Other factors influencing antimalarial activity include the stability of carbon radicals formed by β-scission subsequent to the initial electron transfer to the peroxide bond and the influence of steric effects remote from the peroxide bond on the interactions between carbon radicals and potential drug targets. The new activity data demonstrates that trioxolane carboxylic acids are usually less active than their hydrocarbon, ester, amide, and hydroxamic acid counterparts. The position of ionizable functional groups such as carboxylic acids and amines is also critical to activity. The best combination of high intrinsic potency and good oral activity is found when a weak base functional group is present.

EXAMPLE 3

Onset of Action and Recrudescence of OZ11, OZ27, OZ78, OZ156, OZ175, OZ177, OZ207, OZ209, OZ277, and OZ279

Onset of Action and Recrudescence Experiments

The onset of drug action was determined after a single fixed dose of 100 mg/kg (SSV vehicle) po to groups of five animals on day +3 post-infection (day 0). Parasitemias at this point are usually between 25–40%. The infected controls do not survive beyond day +6 post-infection. The reduction of parasitemia is monitored 12, 24, and 48 h after treatment, and the time of recrudescence (>5% parasitemia) is assessed by daily blood smears for 14 days, followed by intermittent assessment for up to 60 days.

The onset part of this experiment reveals how rapidly a compound reduces parasite load; the recrudescence part of the experiment provides information about the efficacy of the compound against the parasite. A long delay in recrudescence can be due to a very good antiparasitic effect of the compound or to a compound with a long half-life.

Both the trioxolanes and the artemisinins produced a rapid decline in parasitemia, confirming that they are rapidly acting antimalarial agents. In contrast to both chloroquine and these peroxidic antimalarials, mefloquine has a slow onset of action. Recrudescence (>5% parasitemia) occurs quite rapidly for artemisinin and artesunate. The time of recrudescence increased for the more lipophilic artemisinin derivatives artemether and arteether.

In contrast to artemether, recrudescence occured much more slowly for the lipophilic trioxolanes OZ11 and OZ27; the recrudescence time for OZ27 was especially marked, superior to that of mefloquine. However, recrudescence times for the relatively polar trioxolanes OZ78, OZ175, and OZ277 were very similar to that of artemether. The more lipophilic trioxolane (OZ156) of the OZ156/OZ177 pair produced the longest delay in recrudescence, longer than chloroquine, but less than mefloquine. The recrudescence times for OZ177 and OZ279 were roughly equivalent to that of chloroquine.

Strikingly, there was no recrudescence observed for OZ207 and OZ209, two different salt forms (OZ207 —tosylate, OZ209 —mesylate) of aminomethyl trioxolane OZ163 (hydrochloride). The recrudescence data for these two trioxolanes suggests that they are either more powerful antimalarial agents or have longer half-lives than any of the semisynthetic artemisinins.

TABLE 2

| Compd | Time of Recrudescence (days) |
|---|---|
| OZ11 | 22.2 |
| OZ27 | 22.0 (3/5), >60 (2/5) |
| OZ78 | 11.2 |
| OZ156 | 19.0 (4/5), >60 (1/5) |
| OZ175 | 13.0 |
| OZ177 | 18.5 |
| OZ207 | >60 |
| OZ209 | >60 |
| OZ277 | 13.0 |
| OZ279 | 15.0 |
| Artemisinin | 8.4 |
| Artesunate | 8.6 |
| Artemether | 12.0 |
| Arteether | 11.4 |
| Chloroquine | 17.8 |
| Mefloquine | 28.0 |

EXAMPLE 4

Effect of Trioxolanes on *Schistosoma* Species

Effect of Trioxolane OZ207 on *Schistosoma japonicum*

TABLE 3

Comparative effect of OZ207 and artemether in mice infected with *Schistosoma japonicum*

| Drug | Age of worm | Dose (mg/kg × 1) | Mice without ♀ worm | MTWB/ x ± SD | WRR/% | MFWB/ x ± SD | FWRR/% |
|---|---|---|---|---|---|---|---|
| Control | — | — | 0/8 | 26.6 ± 4.2 | — | 11.6 ± 2.4 | — |
| OZ207 | 35 days | 200 | 4/7 | 9.1 ± 3.9 | 66 | 0.6 ± 0.7 | 95 |
| OZ207 | 35 days | 400 | 4/6 | 4.3 ± 1.2 | 84 | 0.7 ± 1.2 | 94 |
| Artemether | 35 days | 400 | 0/7 | 10.1 ± 4.4 | 62 | 3.4 ± 1.6 | 71 |
| OZ207 | 7 days | 200 | 0/8 | 5.4 ± 2.4 | 81 | 2.1 ± 1.0 | 82 |

MTWB, mean total worm burden;
WRR, worm reduction rate
MFWB, mean female worm burden;
FWRR, female worm reduction rate.

Table 3 illustrates that the mean total worm burden and mean female worm burden in OZ207 400 mg/kg group was significantly lower than those in artemether 400 mg/kg group ($P<0.01$). The mean female worm burden in OZ207 200 mg/kg group was also significantly lower than that in artemether group ($P<0.01$).

Effect of Trioxolanes on 21-day-old Schistosomules

Mice were infected with 100 *Schistosoma mansoni* cercariae on day 21 post-treatment. Each group was treated per os with trioxolanes at a single dose of 200 mg/kg. Untreated mice served as the control. All groups were killed 4 weeks after treatment and the liver and intestine were removed and separated. The liver and intestine were compressed and alive male and female worms could be seen and counted. The effect of the compounds was evaluated by mean total and female worm burden. The results are shown in Table 4.

Effect of Trioxolanes on Adult schistosomes (49-day-old)

Mice were infected with 100 *Schistosoma mansoni* cercariae on day 49 post-treatment. Each group was treated per os with OZ compounds at single doses of 200, 400, and 600 mg/kg. Untreated mice served as the control. All groups were killed 4 weeks after treatment and the liver and intestine were removed and separated. The liver and intestine were compressed and alive male and female worms could be seen and counted. The effect of the compounds was evaluated by mean total and female worm burden, and the results are set forth in Table 4.

TABLE 4

IN VIVO ACTIVITY AGAINST *SCHISTOSOMA MANSONI* (MICE female INFECTED)

| OZ COMPOUNDS TESTED | % reduction of schistosomule growth at day 21 after per os application of 200 mg/kg | | % reduction of adult worms growth at day 49 after per os application of . . . mg/kg | | |
|---|---|---|---|---|---|
| | | | 200 | 400 | 600 |
| | TWR (%) | FWR (%) | | TWR (%)/ DEAD WORM (%) | |
| OZ 03 liquid | 74 | 74 | | 29/8 | |
| OZ 04 | 7 | 7 | | 0/0 | |
| OZ 05 | 90 | 88 | 46/12 | 23/32 | 70/58 |
| OZ 10 | 66 | 73 | | 28/13 | 21/23 |
| OZ 11 | 85 | 84 | | 16/4 | |
| OZ 12 | 78 | 79 | | 14/0 | |
| OZ 14 | 7 | 0 | | 0/0 | |
| OZ 15 | 63 | 70 | | 0/10 | |
| OZ 16 | 78 | 77 | | ND | |
| OZ 17 | 23 | 7 | | 0/5 | |
| OZ 18 | 12 | 9 | | 0/0 | |
| OZ 19 | 77 | 74 | | ND | |
| OZ 20 | 0 | 0 | | 0/0 | |
| OZ 21 liquid | 18 | 20 | | 0/0 | |
| OZ 22 | 75 | 76 | | ND | |
| OZ 23 | 90 | 84 | | 0/4 | |
| OZ 24 | 65 | 61 | | 21/0 | |
| OZ 25 | 86 | 84 | | 46/34 | |
| OZ 26 | 37 | 40 | | ND | |
| OZ 27 | 63 | 58 | | 20/10 | |
| OZ 28 | 81 | 87 | | ND | |
| OZ 29 | 28 | 20 | | 0/0 | |
| OZ 30 | 16 | 12 | | ND | |
| OZ 31 | 60 | 63 | | 4/4 | |
| OZ 32 | 73 | 70 | | 27/28 | |
| OZ 33 | 28 | 14 | | ND | |

TABLE 4-continued

IN VIVO ACTIVITY AGAINST *SCHISTOSOMA MANSONI* (MICE female INFECTED)

| OZ COMPOUNDS TESTED | % reduction of schistosomule growth at day 21 after per os application of 200 mg/kg | | % reduction of adult worms growth at day 49 after per os application of . . . mg/kg | | | |
|---|---|---|---|---|---|---|
| | TWR (%) | FWR (%) | 200 TWR (%)/ DEAD WORM (%) | 400 | 600 | |
| OZ 35 | 73 | 63 | | ND | | |
| OZ 36 | 16 | 12 | | 0/0 | | |
| OZ 37 | 63 | 53 | | ND | | |
| OZ 43 | ND | ND | | 1/0 | | |
| OZ 49 | ND | ND | | 17/10 | | |
| OZ 50 | ND | ND | | 12/4 | | |
| OZ 56 | 69 | 66 | | ND | | |
| OZ 61 | ND | ND | | 8/21 | | |
| OZ 67 | ND | ND | | 38/0 | | |
| OZ 68 | ND | ND | | 17/0* | | *2 mice |
| OZ 71 | 91 | 85 | | 0/16 | | |
| OZ 72 | ND | ND | | 0/10 | | |
| OZ 76 | ND | ND | | 32/0 | | |
| OZ 78 | 82 | 87 | 24/29 | 0/17 | 0/14 | |
| OZ 79 | ND | ND | | 4/0 | | |
| OZ 80 | 79 | 75 | 0/3 | ND | | |
| OZ 81 | ND | ND | | 28/0 | | |
| OZ 83 | ND | ND | | 7/19 | | |
| OZ 89 | 86 | 81 | | 0/17 | | |
| OZ 90 liquid | 81 | 79 | | ND | | |
| OZ 105 | ND | ND | | 8/0 | | |
| OZ 107 | ND | ND | | 26/4 | | |
| OZ 108 | 30 | 28 | | 28/0 | | |
| OZ 111 | 71 | 68 | | ND | | |
| OZ 119 | 88 | 87 | | ND | | |
| OZ 126 | ND | ND | | 0/9 | | |
| OZ 130 | ND | ND | | 0/8 | | |
| OZ 140 | ND | ND | | 0/3 | | |
| OZ 145 | 80 | 83 | | ND | | |
| OZ 148 | ND | ND | | 25/0 | | |
| OZ 151 | 19 | 19 | | ND | | |
| OZ 152 | 19 | 11 | | ND | | |
| OZ 153 | ND | ND | | No alive/dead worm* | | *1 mouse |
| OZ 154 | ND | ND | | 58/0* | | *see 519+ OZ 180 |
| OZ 156 | 75 | 72 | | 0/6 | | |
| OZ 157 | 65 | 68 | | ND | | |
| OZ 159 | 19 | 19 | | ND | | |
| OZ 160 | 15 | 0 | | ND | | |
| OZ 163 | 84 | 80 | | ND | | |
| OZ 169 | 0 | 0 | | ND | | |
| OZ 189 | ND | ND | 0/17* | Tox: 3/3 | | *Tox: 2/3 |
| OZ 205 | 84 | 83 | | 0/12 | | |
| OZ 207 | ND | ND | 32/17 | 35/21 | 11/24++ | Tox: ++2/5 |
| OZ 209 | 85 | 84 | 39/34 | 16/28+ | 41/21++ | Tox: ++2/5 ++4/5 |
| OZ 226 | ND | ND | | 52/0* | | *1 mouse |
| OZ 256 | 85 | 86 | | 10/19 | | |
| OZ 271 | 88 | 86 | | 0/6 | | |
| OZ 277 | 91 | 92 | | 0/0 | 17/14 | 1 × 600 sc. 39/17 |
| OZ 279 | 86 | 88 | | 0/12 | 33/20 | 1 × 600 sc. 21/27 |
| OZ 281 | 91 | 90 | | 12/15 | | |
| OZ 285 liquid | 86 | 85 | | 17/22 | | |
| OZ 288 | 95 | 96 | | 52/45 | | |
| OZ 296 | 85 | 85 | | 1/13 | | |
| OZ 309 | 97 | 100 | | 19/17 | | |
| OZ 312 | 94 | 93 | | 16/9 | | |
| OZ 323 | 95 | 97 | | 20/23 | | |
| OZ 329 | 90 | 90 | | 15/6 | | |
| OZ 349 | ND | ND | | 36/16 | | |
| OZ 352 | 89 | 91 | | 16/26 | | |
| OZ 360 | 17 | 13 | | 0/0 | | |
| ARTEMETHER | (n4) 85 | (n4) 85 | (n2) | 53/29 | | |
| PRAZIQUANTEL | 0 | 0 | (n2) | 96/96 | 100/100 | |

EXAMPLE 5

Activity of Trioxolanes Against *P. berghei*

In the single dose $ED_{50}/ED_{90}/ED_{99}$ determinations, Moro SPF or NMRI mice (group of three) infected with the ANKA strain of *Plasmodium berghei* were treated on day one post-infection. Trioxolanes were dissolved or suspended in the standard suspending vehicle (SSV) and administered as single 10, 6, 3, 1, 0.3, and 0.1 mg/kg doses po and sc. The SSV consists of 0.5% w/v CMC, 0.5% v/v benzyl alcohol, 0.4% v/v Tween 80, and 0.9% w/v sodium chloride in water. Antimalarial activity was measured by percent reduction in parasitemia on day three post-infection. The $ED_{50}/ED_{90}$ values were calculated by nonlinear fitting.

TABLE 5

| Compd | $ED_{50}$ (mg/kg) | $ED_{90}$ (mg/kg) | $ED_{99}$ (mg/kg) |
|---|---|---|---|
| OZ05 | 8.7 | 12 | 15 |
| OZ11 | 4.4 | 6.2 | 8.2 |
| OZ27 | 2.9 | 5.7 | 9.9 |
| OZ78 | 4.2 | 9.1 | 17 |
| OZ113 | 3.6 | 9.0 | 19 |
| OZ127 | 2.5 | 7.6 | 19 |
| OZ156 | 1.3 | 2.6 | 4.7 |
| OZ175 | 3.5 | 6.2 | 9.9 |
| OZ177 | 2.1 | 3.7 | 5.8 |
| OZ179 | 1.4 | 3.3 | 6.6 |
| OZ181 | 0.63 | 1.8 | 4.0 |
| OZ205 | 1.6 | 3.3 | 6.0 |
| OZ207 | 0.37 | 1.2 | 3.0 |
| OZ209 | 0.55 | 1.4 | 3.0 |

TABLE 5-continued

| Compd | $ED_{50}$ (mg/kg) | $ED_{90}$ (mg/kg) | $ED_{99}$ (mg/kg) |
|---|---|---|---|
| OZ219 | 1.6 | 3.0 | 5.2 |
| OZ227 | 2.3 | 4.0 | 6.2 |
| OZ235 | 4.0 | 7.1 | 11 |
| OZ277 | 0.78 | 2.0 | 4.4 |
| OZ279 | 0.63 | 1.8 | 3.9 |
| Artesunate | 4.7 | 19 | 60 |
| Artelinate | 4.8 | 10 | 18 |
| Artemether | 2.2 | 4.2 | 7.1 |
| Chloroquine | 1.8 | 3.5 | 5.9 |
| Mefloquine | 4.0 | 5.4 | 6.8 |

Table 5 shows ED50/ED90/ED99 data obtained by po administration of trioxolanes in the SSV formulation. The relatively lipophilic artemether is substantially more active than the more polar artesunate and artelinate. In contrast, the most active trioxolanes (OZ181, OZ207, OZ209)—different salt forms of the same amino trioxolane, and amino and amide trioxolanes OZ277 and OZ279, are relatively polar compounds.

EXAMPLE 6

Dosing of OZ279, OZ277, OZ256, and OZ209

Based on results of dosing OZ279, OZ277, OZ256, and OZ209 in rats and dogs, the inventors determined projected optimal dosing of the same compounds in humans. Artesunate is listed as a reference compound.

TABLE 6

| Parameter | Ideal | Accept | Artes | OZ 279 | OZ 277 | OZ 256 | OZ 209 |
|---|---|---|---|---|---|---|---|
| Rat Data | | | | | | | |
| IV t1/2 (10 mg/kg) Oral Bioavailability | 180 min | 60 min | 40 (DMA) | 100.5 | 77.2 | 94.0 | 150.0 |
| 10 mg/kg | >30% | >20% | not done | 37.2 | 36.9 | 18.6 | 12.4 |
| 25 mg/kg | >30% | >20% | 21 (DMA) | 71.1 | 44.1 | 51.9 | 22.4 |
| Oral t1/2 (25 mg/kg) | 180 min | 60 min | not done | 166.8 | 90.5 | 73.3 | 101.5 |
| Dog Data | | | | | | | |
| IV t1/2 (10 mg/kg) Oral Bioavailability | 180 min | 60 min | not done | 177.5 | 95.0 | 85.4 | 182.8 |
| 10 mg/kg | >30% | >20% | not done | 32.8 (V) | 87.9 | 42.0 (V) | 24.5 (V) |
| 25 mg/kg | >30% | >20% | not done | 55.7 (V) | 96.1 | 38.3 (V) | 15.9 (V) |
| Oral t1/2 (10 mg/kg) | 180 min | 60 min | not done | 195.3 | 148.1 | 82.8 | 127.3 |
| Human Data | | | | | | | |
| Projected daily dose mg/day (% BA) | 150 mg | 300 mg | 150–300 (actual) | 105–154 (30%) | 28–56 (30%) | 91–133 (20%) | 35–70 (20%) |

EXAMPLE 7

Effectiveness of Selected OZ Compounds in the Treatment and Prophylaxis of Malarial Infections Moro NMRI male mice (Fü Albino specific pathogen free) weighing 18±2 g were infected intravenously (i.v.) with $2 \times 10^7$ P. berghei ANKA strain-infected erythrocytes from donor mice on day 0 of the experiment. From donor mice with circa 30% parasitemia, heparinized blood was taken and diluted in physiological saline to $10^8$ parasitized erythrocytes per ml. An aliquot (0.2 ml) of this suspension was injected i.v. into experimental and control groups of mice. In untreated control mice, parasitemia rose regularly to 40 to 50% by day 3 post-infection and 70 to 80% by day 4 post-infection. The mice died between days 5 and 7 post-infection. Throughout the experiments, mice were kept in groups of three or five animals in Makrolon type II cages in an air-conditioned animal room at 22 to 23° C. A diet with p-aminobenzoic acid (PABA) of 45 mg (NAFAG FUTTER© food N° 9009 PAB-45) per kg of body weight, and tap water is available ad libitum.

OZ compounds were prepared at an appropriate concentration, either as a solution or a suspension containing SSV (0.5% w/v CMC, 0.5% v/v benzyl alcohol, 0.4% v/v Tween 80, and 0.9% w/v sodium chloride in water). They were administered per os (p.o.) in a total volume of 0.01 ml per gram of mouse. The activity of the compound was determined by a variety of methods outlined in subsequent sections. Survival time was also recorded, and survival to day 30 post-infection was considered to be a cure.

The first experiment conducted consisted of administration of a divided 3×10 mg/kg p.o. dose administered on days 1, 2, and 3 post-infection vs. a single 1×30 mg/kg po dose administered on day 1 post-infection. On day 4 post-infection, blood smears of all animals were prepared and stained with Giemsa. Parasitemia was determined microscopically, and the difference between the mean value of the control group (taken as 100%) and those of the experimental groups was calculated and expressed as percent reduction. Compounds were administered orally in the SSV vehicle. The results are shown in Table 7 below:

TABLE 7

| | 1 × 30 mg/kg | | | 3 × 10 mg/kg | | |
|---|---|---|---|---|---|---|
| | Activity % | Survival (days) | | Activity (%) | Survival (days) | |
| OZ | p.o. SSV | | Cures | p.o. SSV | | Cures |
| 209 | 100 | >30 | 0/5 | 100 | >30 | 3\3 |
| 271 | 99.97 | 14 | 0/5 | 100 | 27.8 | 4\5 |
| 277 | 99.92 | 10.4 | 0/5 | 100 | 27.6 | 4\5 |
| 279 | 99.95 | 14.8 | 0/5 | 100 | 25.4 | 3\5 |
| 301 | NA | NA | NA | 100 | >30 | 5\5 |
| 315 | NA | NA | NA | 100 | >30 | 5\5 |
| CQ | 99.94 | 9.5 | 0/5 | 99.99 | 14.3 | 0/5 |
| M FQ | 99.94 | 20.3 | 0/5 | 99.92 | 23.3 | 0/5 |
| AS | 83.83 | 9 | 0/5 | 98.62 | 11 | 0/5 |

As shown by Table 7, a 3×10 mg/kg dose of these trioxolanes cured between 3/5 and 5/5 of the infected mice. At this same dose, none of the standard antimalarial drugs cured any of the infected mice. At the 1×30 mg/kg dose, all tested trioxolanes showed activities >99.9% on day 3 post-treatment.

The second experiment consists of administration of divided 3×3 mg/kg and 3×1 mg/kg po doses administered on days 1, 2, and 3 post-infection. On day 4 post-infection, blood smears of all animals were prepared and stained with Giemsa. Parasitemia was determined microscopically, and the difference between the mean value of the control group (taken as 100%) and those of the experimental groups was calculated and expressed as percent reduction. Compounds were administered orally in the SSV vehicle. The results are shown in Table 8.

TABLE 8

| | 3 × 3 mg/kg | | | 3 × 1 mg/kg | |
|---|---|---|---|---|---|
| | Activity (%) | Survival (days) | | Activity (%) | Survival (days) |
| OZ | p.o. SSV | | Cures | p.o. SSV | |
| 209 | 100 | 16.4 | 0\5 | 99.51 | 9.4 |
| 271 | 99.99 | 16.2 | 0\5 | 87 | 8.8 |
| 277 | 100 | 14 | 0\5 | 83 | 9.4 |
| 279 | 100 | 14.8 | 0\5 | 83 | 8.8 |
| 281 | 100 | 12.4 | 0\5 | 92 | 13 |
| 288 | 99 | 10.2 | 0\5 | 49 | 8.4 |
| 289 | 100 | 17.2 | 0\5 | 41 | 7.4 |
| 290 | 93 | 10.6 | 0\5 | 14 | 6.8 |
| 296 | 94 | 9.4 | 0\5 | 49 | 7.8 |
| 297 | 89 | 9.4 | 0\5 | 22 | 6.4 |
| 298 | 99.99 | 16.4 | 0\5 | 93 | 11 |
| 301 | 100 | 23 | 1\5 | 58 | 8.8 |
| 302 | 99.51 | 13.4 | 0\5 | 87 | 13.4 |
| 305 | 99.91 | 12.2 | 0\5 | 87 | 9.6 |
| 306 | 99.75 | 7.6 | 0\5 | 85 | 11 |
| 309 | 99 | 9.2 | 0\5 | 66 | 9.4 |
| 315 | 99.99 | 22 | 0\5 | 81 | 12.2 |
| 317 | 100 | 16.8 | 0\5 | 73 | 11.4 |
| 319 | 99.97 | 11.2 | 0\5 | 92 | 13 |
| 320 | 96 | 9.6 | 0\5 | 50 | 8.6 |
| 323 | 99.95 | 14.4 | 0\5 | 66 | 14.4 |
| 329 | 100 | 27 | 2\5 | 99.86 | 11 |
| 330 | 99 | 12.6 | 0\5 | 45 | 9.2 |
| 333 | 99 | 10.2 | 0\5 | 64 | 9.4 |
| 335 | 99.99 | 15.4 | 0\5 | 98 | 10 |
| 336 | 100 | 20.8 | 0\5 | 99.14 | 10.4 |
| 337 | 99.98 | 14.4 | 0\5 | 96 | 9.4 |
| 338 | 100 | 25.6 | 0\5 | 98 | 9.4 |
| 339 | 100 | 27 | 3\5 | 97 | 9.2 |
| 343 | 100 | 22.2 | | 87 | 9.4 |
| 349 | 99.98 | 25.2 | 2\5 | 98 | 9.4 |
| 351 | 100 | 22.8 | | 99 | 9.6 |
| 343 | 100 | 22.2 | | 87 | 9.4 |
| 349 | 99.98 | 25.2 | 2\5 | 98 | 9.4 |
| 351 | 100 | 22.8 | | 99 | 9.6 |
| 353 | 99.99 | 16.4 | | 91 | 10 |
| 354 | 99.99 | 24.4 | | 95 | 8 |
| 357 | 100 | 22.4 | 1\5 | 98 | 9.2 |
| 358 | 99.98 | 9.8 | | 79 | 9.8 |
| 359 | 99.65 | 8.6 | | 79 | 8 |
| 365 | 99.96 | 12 | | 79 | 8.4 |
| 368 | 99.99 | 22.2 | | 91 | 8.6 |
| CQ | 99.54 | 10 | | 25 | 7.2 |
| MFQ | 98 | 12 | | 2 | 6.2 |
| AM | 86 | 9.4 | | 51 | 7.2 |
| AS | 78 | 9.4 | | 39 | 6.8 |

As shown by Table 8, at the 3×3 mg/kg dose, fourteen trioxolanes had activities of 100% and produced high survival numbers. Of these, OZ301, OZ329, OZ339, OZ349, and OZ357 cured 1/5, 2/5, 3/5, 2/5, and 1/5 of the infected mice, respectively. At the 3×1 mg/kg dose, most of the trioxolanes were more potent than the reference antimalarial drugs; sixteen of these had activities ≧90%. OZ209, OZ329, and OZ336 were the only trioxolanes with activities greater than 99% at the 3×1 mg/kg dose. All of OZ343-OZ368 that were tested were more active than the reference antimalarial drugs.

Prophylactic activities of the compounds were compared after administering po single dose of 100 mg/kg to different groups of five animals at various times before infection. All groups including an untreated control group, were then infected at the same time. Parasitemia was determined for each animal on day 3 post-infection, and percent of reduction of the level of parasitemia compared to levels for animals given no drug is determined. The results are shown in Table 9.

TABLE 9

| | | | | Prophylactic Activity (%) | | | | | |
|---|---|---|---|---|---|---|---|---|---|
| | AM | AS | CO | MFQ | 209 | 256 | 271 | 277 | 279 | 281 |
| 72 h - | | | | 99.97 | 99.92 | 13 | 99.89 | 9 | 14 | 8 |
| 48 h - | | | 57.49 | 99.92 | 99.9 | 29 | 99.98 | 7 | 27 | 45 |
| 24 h - | 0 | 6.28 | 99.92 | 100 | 100 | 82 | 100 | 25 | 97 | 99.23 |
| 0 h | 100 | 92.44 | 100 | 100 | 100 | 100 | 100 | 100 | 100 | 100 |

The unique prophylactic property of OZ209 (3-day protection, same as MFQ) was found also for OZ271.

EXAMPLE 8

Chemical Properties of OZ277 Salts

The following tosylate, maleate, hydrochloride, tartarate, and succinate salts of OZ277 were synthesized:

cis-Adamantane-2-spiro-3'-8'-[[[(2'-amino-2'-methylpropyl)amino]carbonyl]methyl]-1',2',4'-trioxaspiro[4.5]decane p-tosylate cis-Adamantane-2-spiro-3'-8'-[[[(2'-amino-2'-methylpropyl)amino]carbonyl]methyl]-1',2',4'-trioxaspiro[4.5]decane hydrogen maleate cis-Adamantane-2-spiro-3'-8'-[[[(2'-amino-2'-methylpropyl)amino]carbonyl]methyl]-1',2',4'-trioxaspiro[4.5]decane hydrochloride cis-Adamantane-2-spiro-3'-8'-[[[(2'-amino-2'-methylpropyl)amino]carbonyl]methyl]-1',2',4'-trioxaspiro[4.5]decane hydrogen tartarate cis-Adamantane-2-spiro-3'-8'-[[[(2'-amino-2'-methylpropyl)amino]carbonyl]methyl]-1',2',4'-trioxaspiro[4.5]decane hydrogen succinate Their properties are shown in Table 10:

EXAMPLE 9

Preparation of OZ277 Maleate Salt

Raw Materials:

| Description | Quantity | Mole Equivalent |
|---|---|---|
| OZ277 | 60.00 g | 1.00 |
| Maleic acid | 17.40 g | 0.98 |
| Ethanol | 240 ml | |
| Heptane | 780 ml | |

Process:

Charge ethanol (150 ml) at 20–25° C.;
Charge OZ277 (60 gm) at 20–25° C. under stirring;
Stir at 20–25° C. for 10 min to get clear solution;
Add the solution of maleic acid (17.4 g in 90 ml ethanol) drop wise at 20–25° C. under stirring in 1 hr.;
Charge Heptane (720 ml) at 20–25° C. under stirring;
Stir for 4 hr at 20–25° C.;
Filter the solid and wash with heptane (60 ml);
Suck dry the product;
Dry the product under vacuum at 20–25° C.
The resulting product has a weight of 65–70 grams.

TABLE 10

| Selection criteria | Maleate | Tosylate | HCl | Tartarate | Succinate |
|---|---|---|---|---|---|
| Water solubility | 5 mg/mL | 0.4 mg/mL | 2.5 mg/mL | 2 mg/mL | 1.4 mg/mL |
| Crystallinity | Crystalline | Crystalline | Crystalline | More towards amorphous | Crystalline |
| Hygroscopicity | Non-hygroscopic | Non-hygroscopic | Non-hygroscopic | Hygroscopic | Non-hygroscopic |
| Chemical Stability | Stable | Stable | Stable | Comparatively less stable | Stable |
| Physical stability | Stable | Stable | Stable | Stable | Stable |
| Particle size (90% of particles less than) | ~100 μm | ~50 μm | ~230 μm | ~200 μm | ~150 μm |
| Stability in analytical solution (up to 24 hrs) | Stable | Stable | Stable | Stable | Stable |
| Taste | Not bitter | Not bitter | Not bitter | Not bitter | Not bitter |

It should be appreciated that the Spiro and dispiro 1,2,4-trioxolane compositions of this invention may contain trioxolanes within the scope of the formulas described above, or prodrugs or analogues of these compounds or a racemic mixture of either the D or the L form. The invention is also intended to include all biologically active salt forms of the compounds. Also, minor dosage and formulation modifications of the composition and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

All articles cited herein and in the following list are hereby expressly incorporated in their entirety by reference.

Citations de Almeida Barbosa, L.-C. et al., The Design, Synthesis and Biological Evaluation of Some Stable Ozonides With Anti-malarial Activity. *J. Chem. Soc. Perkin Trans. I,* 1996, 1101–1105.

de Almeida Barbosa, L.-C. et al., Synthesis of Some Stable Oozonides With Anti-malarial Activity. *J. Chem. Soc. Perkin Trans. I,* 1992, 3251–3252.

Cammenga, H. K. et al., Basic principles of thermoanalytical techniques and their applications in preparative chemistry. *Angew. Chem. Int. Ed. Engl.* 1995, 34, 1171–1187.

Cumming, J. N. et al., Antimalarial activity of artemisinin (qinghaosu) and related trioxanes: mechanism(s) of action. *Adv. Pharmacol.* 1997. 37, 254–297.

Dhingra, V. K. et al., Current Status of Artemisinin and Its Derivatives As Antimalarial Drugs. *Life Sci.* 2000, 66, 279–300.

Dong, Y.; Vennerstrom, J. L Peroxidic Antimalarials. *Expert Opin. Ther. Patents* 2001, 11, 1753–1760.

Fishwick, J., et al., The Toxicity of Artemisinin and Related Compounds on Neuronal and Glial Cells in Culture. *Chem.-Biol. Interact.* 1995, 96, 263–271.

Griesbaum, K. et al., Diozonides from coozonolyses of suitable O-methyl oximes and ketones. *Tetrahedron* 1997a, 53, 5463–5470.

Griesbaum, K. et al., Ozonolyses of O-alkylated ketoximes in the presence of carbonyl groups: a facile access to ozonides. *Liebigs Ann./Recueil.* 1997b, 1381–1390.

Jefford, C. Peroxidic Antimalarials. *Adv. Drug Res.* 1997, 29, 271–325.

Kashima, C. et al., Ozonolysis of Five-Membered Heterocycles. *J. Het. Chem.* 1987, 24, 637–639.

Meshnick, S. R. et al., Artemisinin and the antimalarial endoperoxides: from herbal remedy to targeted chemotherapy. *Microbiol. Rev.* 1996, 60, 301–315.

Park, B. K. et al., Safety Assessment of Peroxide Antimalarials: Clinical and Chemical Perspectives. *Br. J. Clin. Pharmacol.* 1998, 46, 521–529.

Titulaer, H. A. C., Zuidema, J., and Lugt, C. B. Formulation and pharmacokinetics of artemisinin and its derivatives. *Int. J. Pharmaceut.* 1991, 69, 83–92.

van Agtmael, M. A. et al., Artemisinin Drugs In the Treatment of Malaria: From Medicinal Herb to Registered Medication. *Trends Pharmacol. Sci.* 1999, 20, 199–205.

Vennerstrom, J. L. et al., Synthesis and Antimalarial Activity of Sixteen Dispiro-1,2,4,5-tetraoxane Analogs of WR 148999: Alkyl Substituted 7,8,15,16-Tetraoxadispiro[5.2.5.2]hexadecanes. *J Med. Chem.* 2000, 43, 2753–2758.

Vroman, J. A. et al., Current Progress in the Chemistry, Medicinal Chemistry and Drug Design of Artemisinin Based Antimalarials. *Curr. Pharm. Design* 1999, 5, 101–138.

Wesche, D. L. et al., Neurotoxicity of artemisinin analogs in vitro. *Antimicrob. Agents. Chemother.* 1994, 38, 1813–1819.

White, N. J. Clinical pharmacokinetics and pharmacodynamics of artemisinin and derivatives. *Trans. R. Soc. Trop. Med. Hyg.* 1994, 88, 41–43.

What is claimed is:

1. A Spiro or dispiro 1,2,4-trioxolane having the following structure:

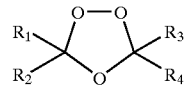

wherein $R_1$, $R_2$, $R_3$, and $R_4$ are the same or different, and are selected from the group consisting of substituted or unsubstituted linear or branched alkyl, aryl, and alkaryl groups and substituted or unsubstituted alicyclic groups that are optionally interrupted by one or more oxygen, sulfur or nitrogen atoms, and substituted or unsubstituted aromatic or heterocyclic groups, whereby none of $R_1$, $R_2$, $R_3$, or $R_4$ can be hydrogen; and further providing that $R_1$ and $R_2$ taken together and/or $R_3$ and $R_4$ taken together optionally form a substituted or unsubstituted alicyclic group which is optionally interrupted by one or more oxygen, sulfur or nitrogen atoms, wherein $R_1$ and $R_2$ taken together is spiroadamantane and $R_3$ and $R_4$ taken together is a spirocyclohexyl ring that is functionalized or substituted at the 4-position.

2. A Spiro or dispiro 1,2,4-trioxolane according to claim 1 wherein the 1,2,4-trioxolane is selected from the group consisting of: OZ05, OZ11, OZ25, OZ27, OZ61, OZ71, OZ78, OZ127, OZ145, OZ156, O163, OZ175, OZ177, OZ179, OZ181, OZ189, OZ205, OZ207, OZ209, OZ210, OZ219, OZ227, OZ229, OZ235, OZ255, OZ256, OZ257, OZ263, OZ264, OZ265, OZ266, OZ267, OZ268, OZ269, OZ270, OZ277, OZ349, OZ351, OZ354, OZ357, OZ359, and OZ368.

3. A pharmaceutical composition comprises a trioxolane as presented in claim 1 wherein the trioxolane is a salt selected from the group consisting of acetate, adipate, alginate, citrate, aspartate, benzoate, benzene sulfonate, bisulfate, butyrate, camphorate, camphor sulfonate, digluconate, glycerophosphate, hemisulfate, heptanoate, hexanoate, fumarate, hydrochloride, hydrobromide, hydroiodide, isethionate, lactate, maleate, methane sulfonate, nicotinate, 2-naphthalene sulfonate, oxalate, palmitoate, pectinate, persulfate, 3-phenyipropionate, picrate, pivalate, propionate, succinate, tartrate, thiocyanate, phosphate, glutamate, bicarbonate, p-toluene sulfonate and undecanoate.

4. The composition of claim 3 wherein the trixolane is selected from the group consisting of cis-adamantane-2-spiro-3'-8'-[[[(2'-amino-2'-methylpropyl)amino]carbonyl]methyl]-1',2',4'-trioxaspiro[4.5]decane p-tosylate; cis-adamantane-2-spiro-3'-8'-[[[(2'-amino-2'-methylpropyl)

amino]carbonyl]methyl]-1',2',4'-trioxaspiro[4.5]decane hydrogen maleate; cis-adamantane-2-spiro-3'-8'-[[[(2'-amino-2'-methylpropyl)amino]carbonyl]methyl]-1',2',4'-trioxaspiro[4.5]decane hydrochloride; cis-adamantane-2-spiro-3'-8'-[[[(2'-amino-2'-methylpropyl)amino]carbonyl]methyl]-1',2',4'-trioxaspiro[4.5]decane hydrogen tartarate; and cis-adamantane-2-spiro-3'-8'-[[[(2'-amino-2'-methylpropyl)amino]carbonyl]methyl]-1',2',4'-trioxaspiro[4.5]decane hydrogen succinate.

5. A method of manufacturing a composition for prophylaxis mid treatment of malaria comprising: mixing a malaria propylaxis or malaria treatment-effective amount of a spiro or dispiro 1,2,4-trioxolane, its prodrugs and optical isomers thereof, with a pharmaceutically acceptable carrier, said trioxolane being sterically hindered on at least one side of the trioxolane heterocycle.

6. A spiro or dispiro 1,2,4-trioxolane having the following structure:

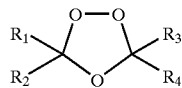

wherein $R_1$ and $R_2$ taken together is spiroadamantane and $R_3$ and $R_4$ taken together is a spirocyclohexyl ring that is functionalized or substituted at the 4-position with an alkyl bridge, whereby said spirocyclohexyl ring is optionally interrupted by one or more oxygen, sulfur, or nitrogen atoms.

7. The spiro or dispiro 1,2,4-trioxolafle of claim 6 wherein the alkyl bridge is methyl or ethyl.

8. The Spiro or dispiro 1,2,4-trioxolane of claim 6 wherein the alkyl bridge is functionalized with a substituent selected from the group consisting of a linear or branched alkyl, ketone, acid, alcohol, amine, amide, sulfonamide, guanidine, ether, ester, oxime, urea, oxime ether, sulfone, lactone, carbamate, semicarbazone, phenyl, heterocycle, and alicyclic group.

9. The spiro or dispiro 1,2,4-trioxolane of claim 6 wherein the alkyl bridge is functiorialized with a substituent that is a weak base.

10. The spiro or dispiro 1,2,4-trioxolane of claim 9 wherein the weak base comprises an amide.

11. The spiro or dispiro 1,2,4-trioxolane of claim 6 wherein the alkyl bridge is methyl.

12. A method of synthesizing a dispiro 1,2,4-triloxolafle comprising: treating a trioxolane having the following structure:

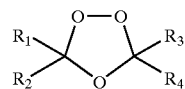

wherein $R_1$ and $R_2$ taken together is spiroadamantane, and $R_3$ and $R_4$ taken together is a spirocyclohexyl ring that is substituted or functionalized at the 4-position with a substituent selected from the group consisting of a ketone, an aldehyde, an ester, and a phthalimide with a reagent selected from the group consisting of a reducing agent, a nucleophile, and a mixture of the same, to form a compound trioxolane having the following structure:

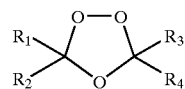

wherein $R_1$ and $R_2$ taken together is spiroadamantane, and $R_3$ and $R_4$ taken together is a spirocyclohexyl ring that is substituted or functionalized at the 4-position with a substituent selected from the group consisting of lactone, alcohol, oxime ether, hydrazone, ketal, acetal, amine, and acid.

* * * * *